United States Patent
Tanaka

(10) Patent No.: US 8,444,572 B2
(45) Date of Patent: May 21, 2013

(54) CAPSULE MEDICAL DEVICE AND BODY-TISSUE OBTAINING METHOD

(75) Inventor: Shinsuke Tanaka, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1146 days.

(21) Appl. No.: 12/324,380

(22) Filed: Nov. 26, 2008

(65) Prior Publication Data

US 2009/0143697 A1 Jun. 4, 2009

(30) Foreign Application Priority Data

Nov. 29, 2007 (JP) ................................. 2007-309381

(51) Int. Cl.
*A61B 19/00* (2006.01)
*A61B 10/00* (2006.01)
*A61B 1/00* (2006.01)

(52) U.S. Cl.
USPC ............................ 600/564; 600/565; 600/101

(58) Field of Classification Search
USPC ......... 600/101, 117, 118, 160, 562, 564–568; 128/899, 903
See application file for complete search history.

(56) References Cited

U.S. PATENT DOCUMENTS

| | | | |
|---|---|---|---|
| 2,881,756 A | 4/1959 | Crosby et al. | |
| 3,289,669 A * | 12/1966 | Dwyer et al. | 600/565 |
| 2001/0051766 A1 | 12/2001 | Gazdzinski | |

FOREIGN PATENT DOCUMENTS

| | | |
|---|---|---|
| DE | 10 2006 014 885 A1 | 10/2007 |
| GB | 1040332 | 8/1966 |
| JP | 2005-342513 | 12/2001 |
| JP | 2003-275170 A | 9/2003 |
| JP | 2003-325438 | 11/2003 |
| JP | 2007-537817 A | 12/2007 |
| JP | 2008-501466 A | 1/2008 |
| WO | WO 00/44285 * | 8/2000 |
| WO | WO 2005 112460 A2 | 11/2005 |
| WO | WO 2005/120325 A2 | 12/2005 |

OTHER PUBLICATIONS

Japanese Office Action dated Jul. 3, 2012 received from the Japanese Patent Office from corresponding Japanese Patent Application No. 2007-309381, together with an English language abstract.

* cited by examiner

*Primary Examiner* — Max Hindenburg
*Assistant Examiner* — Jonathan M Foreman
(74) *Attorney, Agent, or Firm* — Scully, Scott, Murphy & Presser, P.C.

(57) ABSTRACT

A capsule medical device includes a capsule-shaped casing that can be introduced into an in-vivo region of a subject; and a rotation driving unit that generates torque along a circumferential direction of the capsule-shaped casing. The capsule medical device also includes a cutting-obtaining unit that rotates along the circumferential direction of the capsule-shaped casing due to the torque to cut out and obtain a mass of body tissue from the in-vivo region of the subject.

7 Claims, 23 Drawing Sheets

(PHASE A5)

(PHASE D1)    (PHASE D2)

(PHASE E1)   (PHASE E2)

(PHASE E3) (PHASE E4)

(PHASE E5)

(PHASE F1)

(PHASE F2)

CAPSULE MEDICAL DEVICE AND BODY-TISSUE OBTAINING METHOD

CROSS-REFERENCE TO RELATED APPLICATIONS

This application is based upon and claims the benefit of priority from Japanese Patent Application No. 2007-309381, filed Nov. 29, 2007, the entire contents of which are incorporated herein by reference.

BACKGROUND OF THE INVENTION

1. Field of the Invention

The present invention relates to a capsule medical device and a body-tissue obtaining method, for obtaining a mass of body tissue of a region to be examined in a biopsy such as a pathological diagnosis.

2. Description of the Related Art

Conventionally, a capsule medical device which is introduced inside organs of a subject to capture images inside organs (sometimes referred to below as "in-vivo images") has been developed. The capsule medical device has an imaging function and a wireless-transmission function inside a capsule-shaped casing. The capsule medical device is swallowed from a mouth of a subject such as a patient. The capsule medical device successively captures in-vivo images of the subject while moving through a body cavity due to peristalsis and the like, and wirelessly transmits the in-vivo images to a receiving device arranged outside the subject successively as each of the in-vivo images is captured. The capsule medical device introduced into the subject is naturally excreted outside the subject with a bodily waste and the like.

Further, as an example of the conventional capsule medical device, there has been developed a capsule medical device which has an obtaining function for obtaining a cell or a body tissue of the subject. For example, as disclosed in Japanese Patent Application Laid-Open No. 2003-325438, there has been developed a capsule medical device which includes a brush which rotates due to an external rotating magnetic field generated. The brush is rotated when reaching the in-vivo region to be examined so as to obtain the cells such as mucosa cells. Further, there has been developed a capsule medical device which includes forceps which unfold or fold due to the external rotating magnetic field. The forceps are unfolded and folded when reaching the in-vivo region to be examined so as to obtain the body tissue. Further, there has been developed a capsule medical device (an in-vivo robot) which includes forceps which are extended or withdrawn from the capsule-shaped casing (an outer covering of the capsule) due to force for moving forward or backward generated by a driving device. The forceps are extended and withdrawn so as to obtain the body tissue (see Japanese Patent Application Laid-Open No. 2005-342513).

SUMMARY OF THE INVENTION

A capsule medical device according to an aspect of the present invention includes a capsule-shaped casing that can be introduced into an in-vivo region of a subject; a rotation driving unit that generates torque along a circumferential direction of the capsule-shaped casing; and a cutting-obtaining unit that rotates along the circumferential direction of the capsule-shaped casing due to the torque to cut out and obtain a mass of body tissue from the in-vivo region of the subject.

A body-tissue obtaining method according to another aspect of the present invention includes introducing a capsule medical device into a body of a subject; determining whether the capsule medical device has reached the in-vivo region to be examined of the subject; cutting out and obtaining a mass of body tissue from the region to be examined by rotating a cutting-obtaining unit provided in the capsule medical device along a circumferential direction of a casing of the capsule medical device; storing the mass of body tissue obtained in a storage unit inside the capsule medical device; and taking the mass of body tissue stored in the storage unit of the capsule medical device which has excreted from the subject.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule medical device and a body-tissue obtaining method according to the present invention are described in detail with reference to accompanying drawings. The invention, however, do not is not limited to the embodiments.

Figure 1:
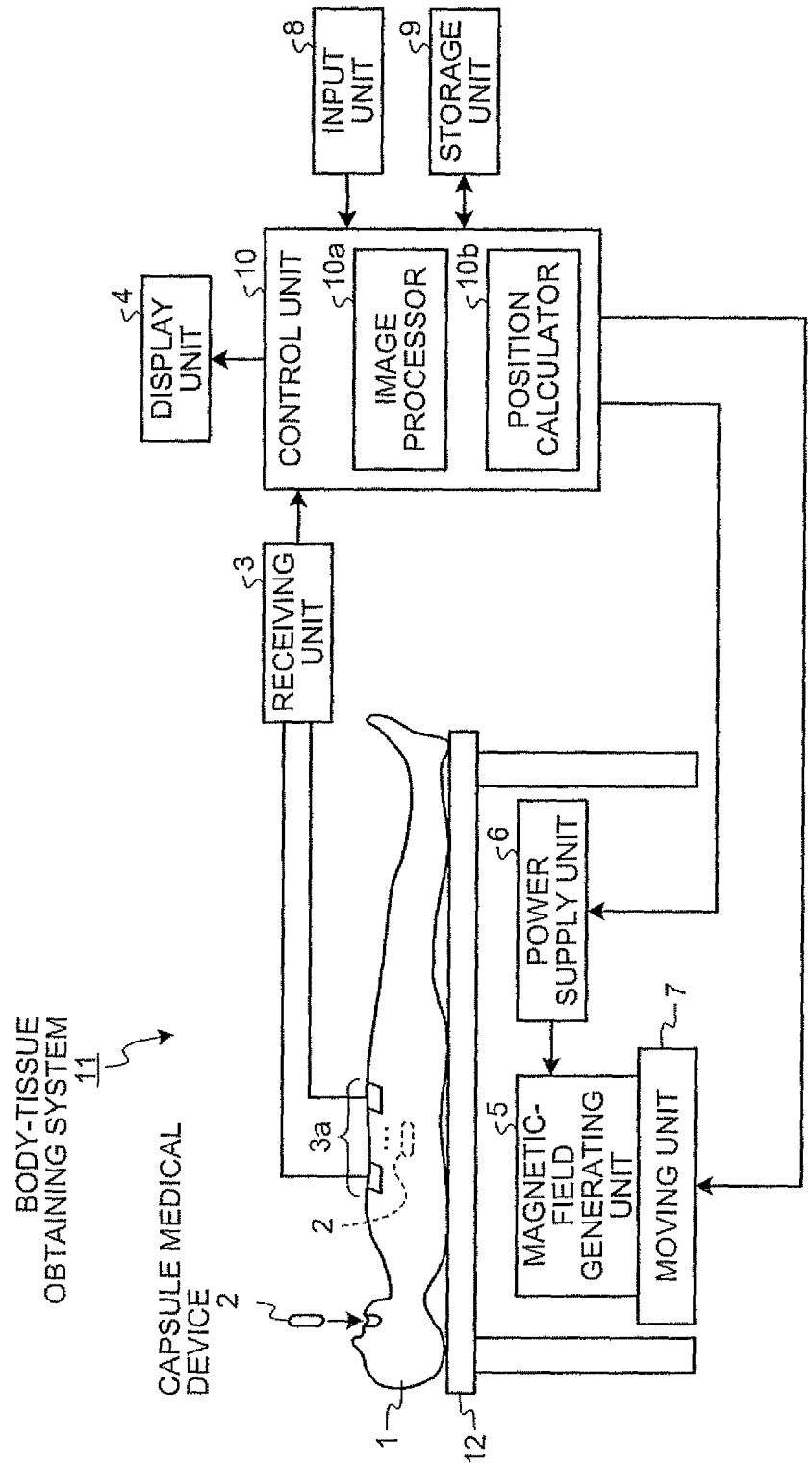
FIG. 1 is a block diagram showing schematically an example configuration of a body-tissue obtaining system according to a first embodiment of the present invention.

FIG. 1 is a block diagram showing schematically an example configuration of a body-tissue obtaining system according to a first embodiment of the present invention. In the body-tissue obtaining system 11 according to the first embodiment, a capsule medical device is introduced into a subject, and the introduced capsule medical device obtains a mass of the body tissue from a desired in-vivo region of the subject. Specifically, as shown in FIG. 1, the body-tissue obtaining system 11 includes a capsule medical device 2 which is introduced into a subject 1 such as a patient to obtain the mass of body tissue inside the subject 1, a receiving unit 3 which receives information transmitted from the capsule medical device 2 via antennas 3a, and a display unit which displays in-vivo images and the like of the subject 1 captured by the capsule medical device 2. Further, the body-tissue obtaining system 11 includes a magnetic-field generating unit 5 which generates a magnetic field for controlling a movement of the capsule medical device 2 inside the subject 1, a power supply unit 6 which supplies power for the magnetic-field generating unit 5, a moving unit 7 which moves the magnetic-field generating unit 5, an input unit 8 which receives inputs of various information, a storage unit 9 which stores therein various information such as the in-vivo images of the subject 1, and a control unit 10 which controls each component of the body-tissue obtaining system 11.

The capsule medical device 2 is of a size which can be introduced into the subject 1, and has a tissue-mass obtaining function for obtaining a mass of body tissue from an in-vivo region of the subject 1. Further, the capsule medical device 2 has an imaging function and a wireless-transmission function inside the capsule-shaped casing. The capsule medical device 2 is introduced into the subject 1 by an oral intake or the like, and successively captures in-vivo images of the subject 1 while moving through digestive organs of the subject 1 due to peristalsis and the like. Every time an in-vivo images is captured, the capsule medical device 2 wirelessly transmits the acquired in-vivo images to an outside of the subject 1 (specifically, the antennas 3a of the receiving unit 3). Further, when reaching the desired in-vivo region inside the subject 1 (e.g., the in-vivo region where the body tissue thereof is to be examined by biopsy such as a pathological diagnosis) the capsule medical device 2 cuts out and obtains the mass of body tissue from the in-vivo region. Storing therein the mass of body tissue, the capsule medical device 2 moves through the digestive organs of the subject 1 until naturally excreted outside the subject 1 at last. The mass of body tissue obtained by the capsule medical device 2 is taken from the inside of the capsule-shaped casing, and used as a sample for the biopsy such as the pathological diagnosis.

The receiving unit 3 is connected to the plural antennas 3a arranged on a body surface of the subject 1. The receiving unit 3 receives wireless-transmission signals from the capsule medical device 2 via the plural antennas 3a, and acquires the image signal included in the received wireless-transmission signals. Specifically, the receiving unit 3 sequentially compares reception electric intensity of the received wireless-transmission signals with each other for each of the plural receiving antennas 3a, and selects the antenna having the highest reception electric intensity from the plural antennas 3a. The receiving unit 3 performs a demodulation process or the like on the wireless-transmission signal which is received from the capsule medical device 2 via the selected antenna, and obtains the image signal included in the wireless-transmission signal. The receiving unit 3 transmits the obtained image signal to the control unit 10. The image signal obtained (demodulated) by the receiving unit 3 includes the in-vivo images captured by the above-described capsule medical device 2 inside the subject 1.

The antennas 3a receive the wireless-transmission signal from the capsule medical device 2 introduced into the subject 1. The antennas 3a are dispersedly arranged on the body surface of the subject 1 inside which the capsule medical device 2 is introduced. One of the antennas 3a at least receives the wireless-transmission signal from the capsule medical device 2 positioned inside the subject 1 (e.g., in digestive organs such as a esophagus, a stomach, a small intestine, and a large intestine), and transmits the received wireless-transmission signal to the receiving unit 3.

The display unit 4 is realized by a display such as a CRT display and an LCD display. The display unit 4 displays thereon various information according to the instructions by the control unit 10. Specifically, the display unit 4 displays a series of in-vivo images of the subject 1 captured by the capsule medical device 2, patient information and examination information of the subject 1 which is input from the input unit 8, current position information of the capsule medical device 2 inside the subject 1, and the like.

Figure 2:
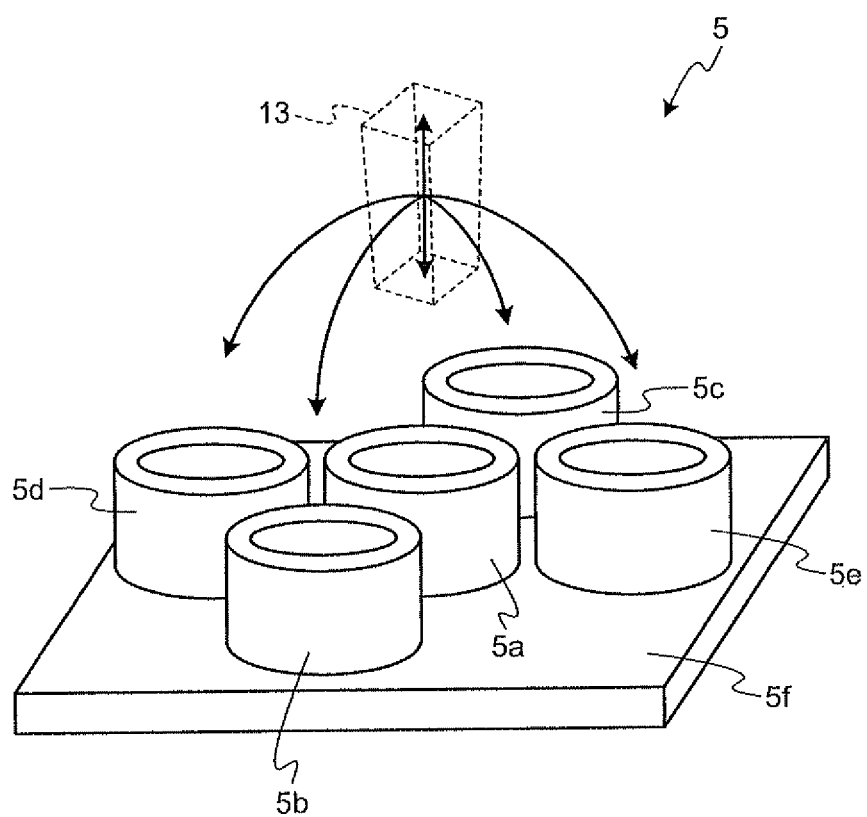
FIG. 2 is a schematic diagram of an example configuration of a magnetic field generating unit.

The magnetic-field generating unit 5 is realized by plural electrical magnets. The magnetic field generation unit 5 generates a magnetic field to be applied to the capsule medical device 2 inside the subject 1 lying on a bed 12. Specifically, as shown in FIG. 2, the magnetic-field generating unit 5 includes electrical magnets 5a to 5e arranged on a plane surface of a table 5f. The electric magnets 5a to 5e are electromagnetic coils which generate the magnetic field when electricity is supplied from a power supply unit 6. The electrical magnet 5a is arranged approximately at the center of the table 5f, and surrounded by the rest of electrical magnets 5b to 5e. The electrical magnets 5b, 5c are arranged at symmetric positions to the electrical magnet 5a while the electrical magnets 5d, 5e are arranged at symmetric positions to the electrical magnet 5a to be separated from the electrical magnets 5b, 5c by 90 degrees around the electrical magnet 5a. The electrical magnets 5a to 5e generate a rotating magnetic field and a gradient magnetic field in a three-dimensional space 13 around a central axis of the coiled electrical magnet 5a.

The electrical magnets 5a to 5e are arranged on the same plane (i.e., the surface of the table 5f). Thus the electrical magnets 5a to 5e on the table 5f generate the rotating magnetic field in the three-dimensional space 13, and increase or decrease force to pull the magnet in the three-dimensional space 13 (e.g., a magnet 24 described later inside the capsule medical device 2) toward the electrical magnet 5a (magnetic attractive force) or force to push the magnet away from the electrical magnet 5a (magnetic repulsive force). The magnetic attractive force or the magnetic repulsive force is magnetic force of the gradient magnetic field generated by the electrical magnets 5a to 5e. The magnetic force forcibly pushes the above-described capsule medical device 2 toward the in-vivo region of the subject 1.

The power supply unit 6 supplies power for the magnetic-field generating unit 5 to generate the magnetic field (rotating magnetic field or gradient magnetic field) to be applied to the capsule medical device 2 inside the subject 1. Specifically, the power supply unit 6 supplies alternate current for the electrical magnets 5a to 5e of the magnetic-field generating unit 5 under a control by the control unit 10, and the magnetic-field generating unit 5 generates the rotating magnetic field and the gradient magnetic field. The rotating magnetic field and the gradient magnetic field of the above-described magnetic-field generating unit 5 are controlled by the alternate current supplied from the power supply unit 6 (amount of electricity from the power supply unit 6).

The moving unit 7 moves the magnetic-field generating unit 5 relative to the subject 1 so that the rotating magnetic field and the gradient magnetic field are applied to the capsule medical device 2 inside the subject 1. Specifically, an XY plane surface is set as being substantially parallel to the lying surface of the bed 12 where the subject 1 lies. The moving unit 7 moves the magnetic-field generating unit 5 to coordinates of position on the XY plane surface under a control by the control unit 10. The moving unit 7 moves the magnetic-field generating unit 5 to a position where the capsule medical device 2 inside the subject 1 is inside the three-dimensional space 13 described above (see FIG. 2).

The input unit 8 is realized by an input device such as a keyboard and a mouse. The input unit 8 allows a user such as a doctor and a nurse to input various information to the control unit 10. The various information which is input via the input unit 8 is, for example, instruction information for instructing the control unit 10, patient information of the subject, examination information of the subject, and the like. The patient information of the subject is information such as patient name, patient ID, date of birth, gender, and age, for identifying the subject. The examination information of the subject is information such as examination ID, and examination date, for identifying a biopsy to be operated with the body tissue obtained from the in-vivo region by the capsule medical device 2 introduced into the subject.

The storage unit 9 is realized by a storage medium such as a RAM, an EFPROM, a flash memory, and a hard disk, which can store rewritable information. The storage unit 9 stores various information to be stored according to the instruction from the control unit 10, and transmits various information to be read out from the stored information according to the instruction from the control unit 10. The storage unit 9 stores, for example, the series of in-vivo images of the subject 1, the patient information and the examination information of the subject 1, and the current position information of the capsule medical device 2 inside the subject 1.

The control unit 10 controls each component of the body-tissue obtaining system 11 (the capsule medical device 2, the receiving unit 3, the display unit 4, the magnetic-field generating unit 5, the power supply unit 6, the moving unit 7, the input unit 8, and the storage unit 9), and controls an input and an output among the components. Specifically, the control unit 10 controls each operation of the receiving unit 3, the display unit 4, the moving unit 7, and the storage unit 9 described above based on the instruction information which is input from the input unit 8, and controls the electricity amount supplied from the power supply unit 6 for the magnetic-field generating unit 5. The control unit 10 controls the electricity amount from the power supply unit 6 to control a magnetic-field orientation and a magnetic-field intensity. The control unit 10 controls the magnetic-field generating unit 5 to guide the capsule medical device 2 inside the subject 1.

Further, the control unit 10 includes an image processor 10a which generates in-vivo images of the subject 1, and a position calculator 10b which calculates a position of the capsule medical device 2 inside the subject 1. The image processor 10a acquires the image signal, which is demodulated based on the wireless-transmission signal from the capsule medical device 2, from the receiving unit 3. The image processor 10a performs a predetermined image processing on the acquired image signal to generate (reconstruct) image information corresponding to the image signal, i.e., the in-vivo image of the subject 1. The series of in-vivo images generated by the image processor 10a are displayed on the display unit 4 and stored in the storage unit 9 as described above.

The position calculator 10b acquires the reception electric intensity of each antenna (for example, the highest three of the reception electric intensity of the antennas 3a) from the receiving unit 3 that is detected when the receiving unit 3 receives the wireless-transmission signals successively transmitted from the capsule medical device 2 via the antennas 3*a*. Based on the acquired reception electric intensity and the position information of each antenna of the antennas 3*a*, the position calculator 10*b* calculates the current position of the capsule medical device 2 inside the subject 1 with a triangular method or the like. The control unit 10 associates the current position information calculated by the position calculator 10*b* with the in-vivo image of the subject 1 that is captured by the capsule medical device 2 at the current position. The in-vivo image of the subject 1 and the current position information of the capsule medical device 2 associated by the control unit 10 are displayed on the display unit 4 and stored in the storage unit 9.

Figure 3:
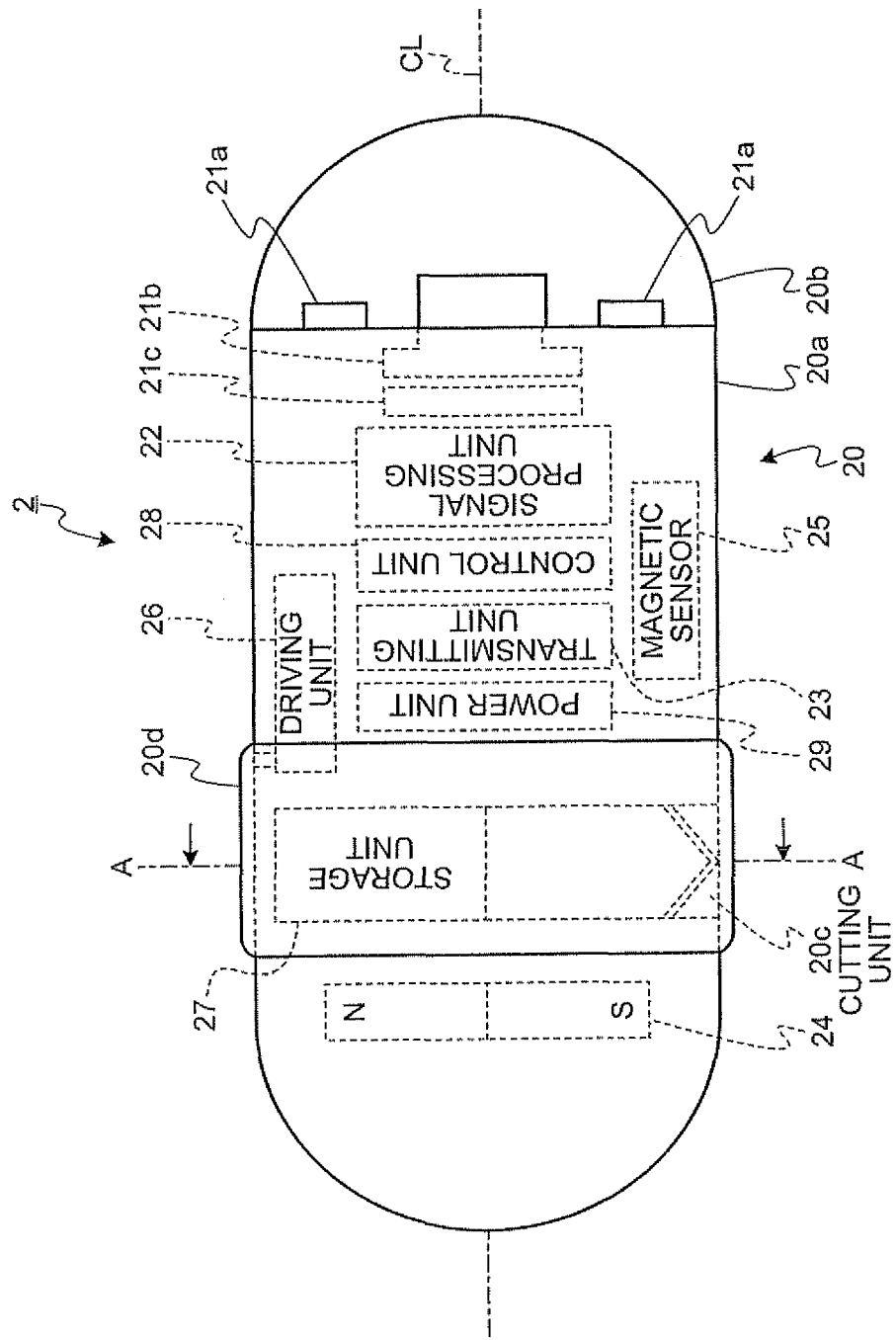
FIG. 3 is a schematic diagram of an example configuration of a capsule medical device according to the first embodiment of the present invention.
Figure 4:
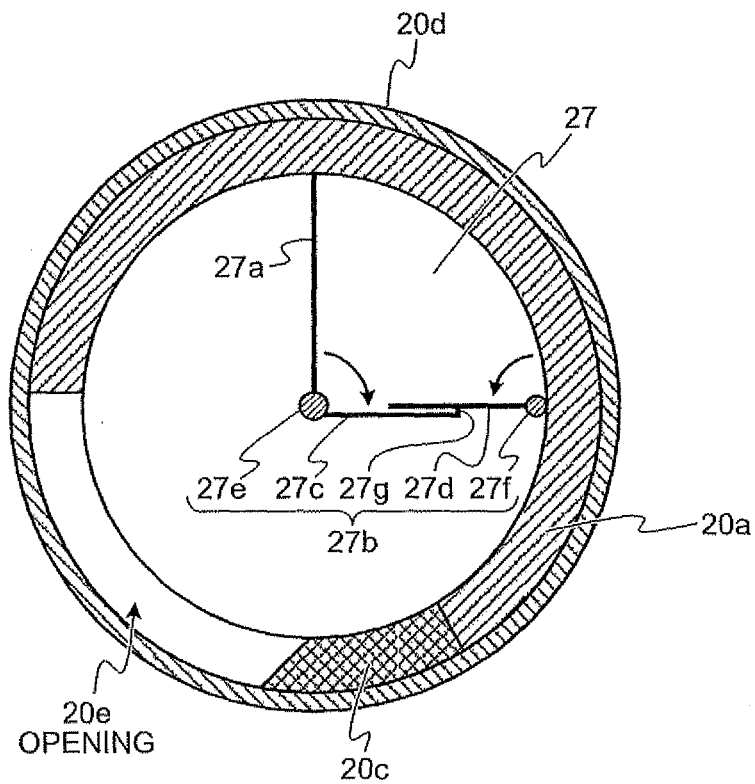
FIG. 4 is a schematic cross-sectional view taken along line A-A of the capsule medical device shown in FIG. 3.
Figure 5:
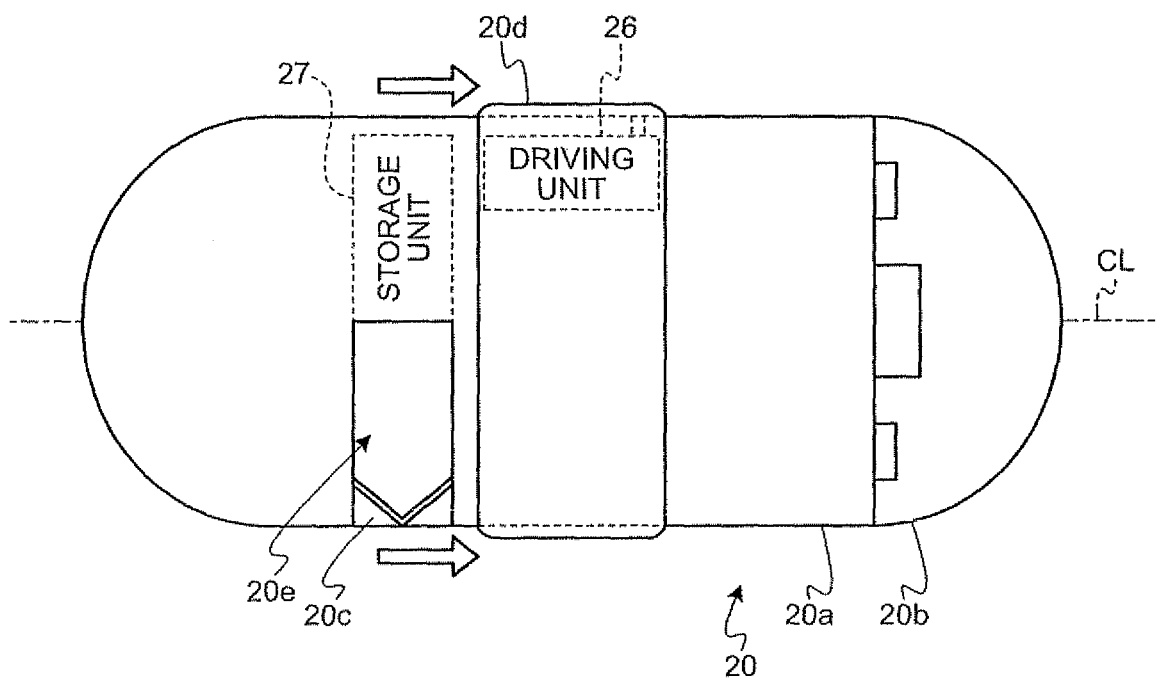
FIG. 5 is a schematic diagram illustrating a state where a cutting unit is exposed as an outer covering of the capsule medical device according to the first embodiment shown in FIG. 3 slides.

A configuration of the above-described capsule medical device 2 is described in detail. FIG. 3 is a schematic diagram of an example configuration of the capsule medical device according to the first embodiment of the present invention. FIG. 4 is a schematic cross-sectional view taken along line A-A of the capsule medical device 2 shown in FIG. 3. FIG. 5 is a schematic diagram illustrating a state where a cutting unit is exposed as an outer covering of the capsule medical device according to the first embodiment shown in FIG. 3 slides. As shown in FIGS. 3 to 5, the capsule medical device 2 according to the first embodiment includes a capsule-shaped casing 20 formed by a cylindrical casing 20*a* and a dome-shaped casing 20*b*, a cutting unit 20*c* which cuts out the mass of body tissue from the in-vivo region of the subject 1, an outer covering 20*d* which covers the cutting unit 20*c*. The capsule medical device 2 includes an illuminating unit 21*a* which illuminates an object, an optical system 21*b* which forms an optical image of the object, an imaging unit 21*c* which captures an image of the object, a signal processing unit 22 which generates an image signal including the image captured by the imaging unit 21*c*, and a transmitting unit 23 which wirelessly transmits the image signal to an outside. Further, the capsule medical device 2 includes a magnet 24 which rotates the capsule-shaped casing 20 due to the external rotating magnetic field, a magnetic sensor which detects the external magnetic field, a driving unit 26 which slides the outer covering 20*d* relative to the capsule-shaped casing 20, a storage unit 27 which stores the mass of body tissue, a control unit 28 which controls each component of the capsule medical device 2, and a power unit 29 which is realized by a battery or the like.

The capsule-shaped casing 20 is of a size which can be introduced into the subject 1. The capsule-shaped casing 20 is formed as another end (open end) of the cylindrical casing 20*a* whose one end is dome-shaped is sealed by the dome-shaped casing 20*b*. The dome-shaped casing 20*b* is an optical dome which is transparent to light within a predetermined wavelength band (e.g., visible light). The cylindrical casing 20*a* is a substantially opaque casing having an opening 20*e* thereon. The cutting unit 20*c* is arranged on an edge of the opening 20*e*. The storage unit 27 is arranged in a space inside the cylindrical casing 20*a* communicating with the opening 20*e*. The outer covering 20*d* which covers the cutting unit 20*c* and the opening 20*e* is arranged on an outer wall of the cylindrical casing 20*a*, and the outer covering 20*d* can slide. In the capsule-shaped casing 20 formed by the cylindrical casing 20*a* and the dome-shaped casing 20*b*, the dome-shaped casing 20*b* includes the illuminating unit 21*a*, the optical system 21*b*, and the imaging unit 21*c* while the cylindrical casing 20*a* includes the signal processing unit 22, the transmitting unit 23, the magnet 24, the magnetic sensor 25, the driving unit 26, the control unit 28, and the power unit 29.

The cutting unit 20*c* cuts out and obtains the mass of body tissue from the in-vivo region of the subject 1. Thus, the cutting unit provides a cutting-obtaining function. Specifically, the cutting unit 20*c* is a blade having, for example, a V-shaped edge, and is fixated on an edge of the opening 20*e* with the edge of the cutting unit 20*c* facing in the circumferential direction of the cylindrical casing 20*a*. The cutting unit 20*c* rotates along the circumferential direction of the capsule-shaped casing 20 with the capsule-shaped casing 20 (specifically, the cylindrical casing 20*a*) due to force generated by the magnet 24 which is described later, to thereby cut out and obtain the mass of body tissue from the in-vivo region of the subject 1. The mass of body tissue cut out and obtained by the cutting unit 20*c* is taken in the capsule-shaped casing 20 via the opening 20*e*.

The outer covering 20*d* covers the cutting unit 20*c* except when the cutting unit 20*c* cuts out and obtains the mass of body tissue from the in-vivo region of the subject 1. Specifically, the outer covering 20*d* is a ring-shaped member which can slide in a direction of a central shaft CL (i.e., a longitudinal direction of the capsule-shaped casing 20) along an outer wall surface of the capsule-shaped casing 20, and which is connected with the driving unit 26 via a shaft. The central shaft CL is set along the longitudinal direction of the capsule-shaped casing 20 as shown in FIGS. 3 and 5. The driving unit 26 has the outer covering 20*d* reciprocate in the direction of the central shaft CL under a control by the control unit 28 to switch to a state where the cutting unit 20*c* is exposed to the in-vivo region of the subject 1, or a state where the cutting unit 20*c* is covered. The outer covering 20*d* covers the cutting unit 20*c* except when the cutting unit 20*c* cuts out and obtains the mass of body tissue from the in-vivo region of the subject 1 so that the cutting unit 20*c* does not accidentally hits the in-vivo region of the subject 1. The outer covering 20*d* works as a cap covering the opening 20*e* of the cylindrical as well as the cutting unit 20*c* so that the mass of body tissue does not drop out of the capsule-shaped casing 20 via the opening 20*e*.

The magnet 24 works as a rotation driving unit which generates torque along the circumferential direction of the capsule-shaped casing 20 due to the external rotating magnetic field. Specifically, the magnet 24 is realized by a permanent magnet, a electrical magnet, or a magnetic body, and the magnet 24 is fixated inside the cylindrical casing 20*a*, and the magnet 24 is magnetized in a direction vertical to the longitudinal direction along the central shaft CL of the capsule-shaped casing 20, i.e., in a radial direction of the capsule-shaped casing 20. The magnet 24 forces the capsule-shaped casing 20 into the in-vivo region of the subject 1 due to the above-described gradient magnetic field generated by the magnetic-field generating unit 5, and rotates the cutting unit 20*c* and the capsule-shaped casing 20 along the circumferential direction of the capsule-shaped casing 20 due to the above-described rotating magnetic field generated by the magnetic-field generating unit 5. In this case, with the cutting unit 20*c* rotating with the capsule-shaped casing 20 along the circumferential direction, the torque along the circumferential direction of the capsule-shaped casing 20 generated by the magnet 24 is converted into cutting force to cut out the mass of body tissue from the in-vivo region.

The illuminating unit 21*a* is realized by a light-emitting device such as an LED. The illuminating unit 21*a* illuminates an object (specifically, an inside of organs of the subject 1) through the dome-shaped casing 20*b*. The optical system 21*b* is realized by a condensing lens and a lens frame, or the like. The optical system 21*b* condenses reflected light of the object illuminated by the illuminating unit 21*a* and forms an optical image of the object on a light-receiving surface of the imaging unit 21*c*. The imaging unit 21*c* is realized by a solid-state image sensing device such as a CCD type and a CMOS type. The imaging unit 21*c* captures the optical image of the object formed by the optical system 21b, i.e., the in-vivo image of the subject 1. The signal processing unit 22 acquires a signal converted photoelectrically by the imaging unit 21c, and performs a predetermined signal processing on the acquired signal to generate an image signal including the in-vivo image of the subject 1.

The transmitting unit 23 acquires the image signal generated by the signal processing unit 22, and performs a predetermined modulation process and the like on the acquired image signal to generate a wireless-transmission signal including the image signal. The transmitting unit 23 transmits the generated wireless-transmission signal to an outside. The wireless-transmission signal generated by the transmitting unit 23 is received by the receiving unit 3 via the antennas 3a.

The magnetic sensor 25 monitors an outside to check whether the external magnetic field is present, constantly or at regular intervals under a control by the control unit 28. The magnetic sensor 25 detects the external magnetic field when the external magnetic field (the rotating magnetic field or the gradient magnetic field) is applied to the capsule medical device 2 from the magnetic-field generating unit 5. The magnetic sensor 25 notifies the control unit 28 of the detection result of the external magnetic field.

The control unit 28 controls the illuminating unit 21a, the imaging unit 21c, the signal processing unit 22, the transmitting unit 23, the magnetic sensor 25, and the driving unit 26. Specifically, the control unit 28 controls the illuminating unit 21a and the imaging unit 21c so that the imaging unit 21c captures the image of the object (i.e., the in-vivo image) illuminated by the illuminating unit 21a, and controls the signal processing unit 22 and the transmitting unit 23 so that the image signal including the in-vivo image of the subject 1 captured by the imaging unit 21c is wirelessly transmitted. Further, when the detection signal indicating that the external magnetic field is detected is acquired from the magnetic sensor 25, the control unit 28 controls the driving unit 26 to move the outer covering 20d along the central shaft CL so that the cutting unit 20c is exposed to the in-vivo region of the subject 1. On the other hand, when the detection signal is not acquired from the magnetic sensor 25 for a predetermined time, the control unit 28 controls the driving unit 26 to cover the cutting unit 20c and the opening 20e.

The power unit 29 is realized by a switching circuit and a button-shaped battery, or the like. With the switching circuit switched to an ON state, the power unit 29 supplies power for the illuminating unit 21a, the imaging unit 21c, the signal processing unit 22, the transmitting unit 23, the magnetic sensor 25, the driving unit 26, and the control unit 28 described above.

The storage unit 27 stores the mass of body tissue which is cut out and obtained by the above-described cutting unit 20c. As shown in FIGS. 3 to 5, the storage unit 27 is arranged near the opening 20e of the cylindrical casing 20a inside the capsule-shaped casing 20. The storage unit 27 is arranged inside the cylindrical casing 20a and separated from built-in components of the capsule medical device 2 (specifically, electrical components of the imaging unit 21c, the control unit 28, and the like; the power unit 29 such as the battery; the magnet 24; and the like). The storage unit 27 is formed with a wall part 27a and an opening-closing part 27b. The storage unit 27 stores the mass of body tissue in a space which is surrounded by the wall part 27a, the opening-closing part 27b, and a portion of the cylindrical casing 20a.

The opening-closing part 27b opens inward, and includes lid parts 27c, 27d, and hinge parts 27e, 27f which support the lid parts 27c, 27d in a manner such that the lid parts 27c, 27d can be opened and closed, and a sealing member 27g which securely seals up the closed lid parts 27c, 27d. Specifically, the lid part 27c is rotatably supported by the hinge part 27e, and the lid part 27c can be opened and closed inward the hinge part 27e, a supporting point in the storage unit 27. The hinge parts 27e, 27f include torsion springs (not shown), respectively, and keep the lid parts 27c, 27d closed (see FIG. 4) by urging force of the torsion springs. The sealing member 27g is arranged on a surface of the lid part 27c opposing to the lid part 27d in a closed state to water-tightly seal up the closed lid parts 27c, 27d.

A spring constant of the torsion springs of the hinge parts 27e, 27f is adjusted to keep the lid parts 27c, 27d closed as shown in FIG. 4, and have the lid parts 27c, 27d opened with a weight of the mass of body tissue when the mass of body tissue which is cut out and obtained by the above-described cutting unit 20c is placed onto the lid parts 27c, 27d.

In the body-tissue obtaining system 11 shown in FIG. 1, the capsule medical device 2 configured as above is introduced into the subject 1 (introducing step), captures the series of in-vivo images of the subject 1 while moving through the digestive organs of the subject 1 due to the peristalsis and the like, and wirelessly transmits the series of captured in-vivo images of the subject 1 to the outside. On the other hand, the control unit 10 successively acquires the image signal from the receiving unit 3, and displays on the display unit 4 the in-vivo image of the subject 1 generated by the image processor 10a and the current position information of the capsule medical device 2 calculated by the position calculator 10b. The user such as the doctor and the nurse checks the in-vivo image and the current position information displayed on the display unit 4 to determine whether the capsule medical device 2 inside the subject 1 reaches the in-vivo region to be examined (determining step).

When the capsule medical device 2 reaches the in-vivo region to be examined, the user refers to the in-vivo image and the current position information displayed on the display unit 4, and controls the magnetic-field generating unit 5 and the moving unit 7 via the input unit 8. The moving unit 7 moves the magnetic-field generating unit 5 to a proper position in correspondence with the current position of the capsule medical device 2. The magnetic-field generating unit 5 generates the rotating magnetic field and the gradient magnetic field at the current position of the capsule medical device 2. The capsule medical device 2 inside the subject 1 rotates the cutting unit 20c along the circumferential direction of the capsule-shaped casing 20 due to the rotating magnetic field and the gradient magnetic field, and cuts out and obtains the mass of body tissue from the in-vivo region of the subject 1 (cutting-obtaining step). The mass of body tissue is stored in the storage unit 27 of the capsule medical device 2 (storing step).

The control unit 10 controls the magnetic-field generating unit to stop generating the rotating magnetic field and the gradient magnetic field. As a result, the capsule medical device inside the subject 1 is no longer affected by the rotating magnetic field and the gradient magnetic field described above, and moves through the digestive organs due to the peristalsis and the like until naturally excreted outside the subject 1 at last. The mass of body tissue stored in the storage unit 27 of the capsule medical device 2 is taken by the doctor, the nurse, or the like (retrieving step), and used for the biopsy such as the pathological diagnosis.

Figure 6:
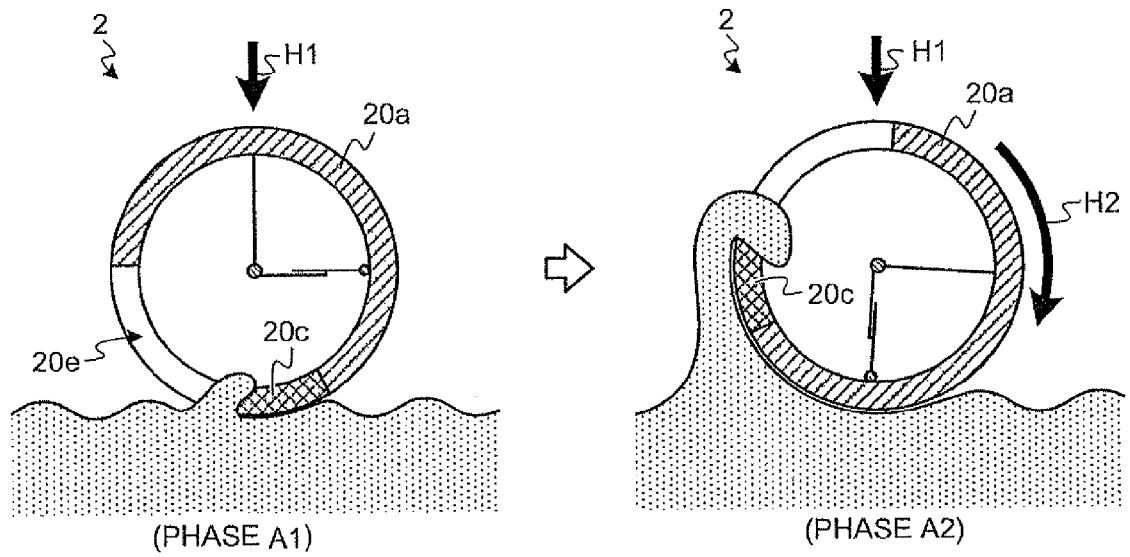
FIG. 6 is a schematic diagram illustrating phases where a portion of an in-vivo region is captured by the cutting unit of the capsule medical device according to the first embodiment.
Figure 7:
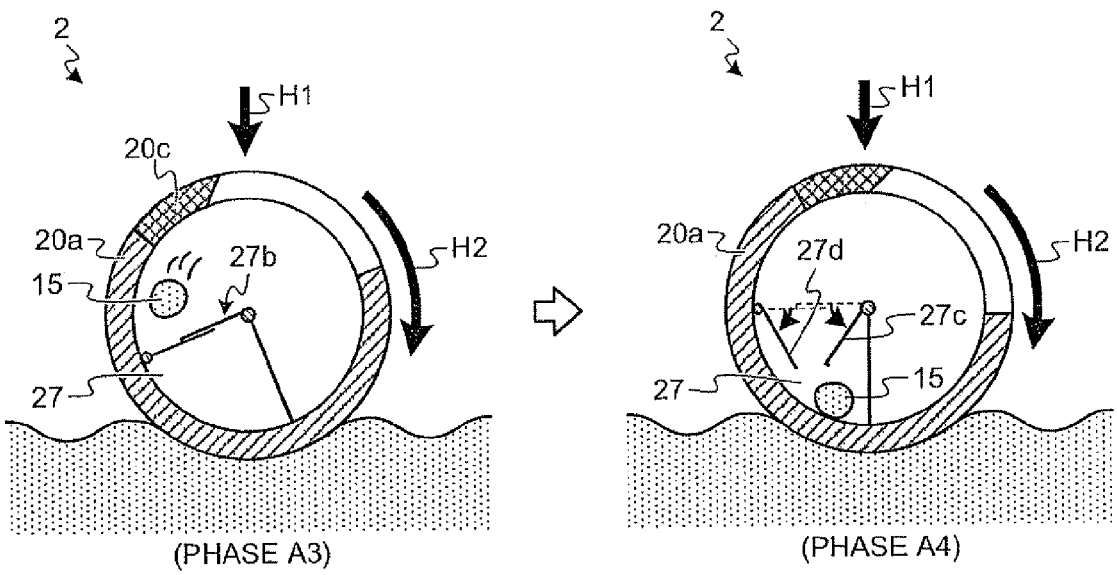
FIG. 7 is a schematic diagram illustrating phases where a mass of body tissue is cut out and obtained from the in-vivo region by the cutting unit of the capsule medical device according to the first embodiment.
Figure 8:
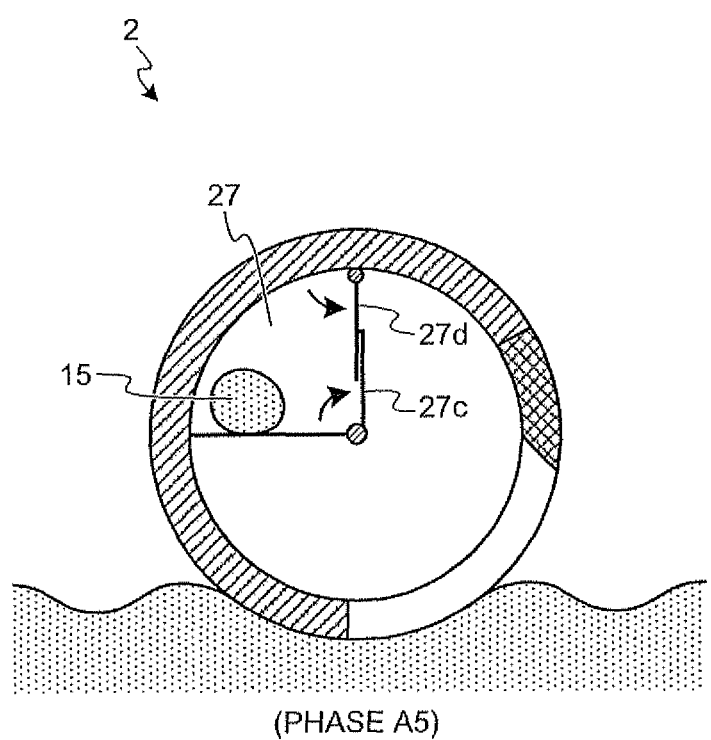
FIG. 8 is a schematic diagram illustrating a phase where the mass of body tissue is stored in a storage unit of the capsule medical device according to the first embodiment.

An operation of the capsule medical device for cutting out and obtaining the mass of body tissue from the in-vivo region of the subject 1 is described. FIG. 6 is a schematic diagram illustrating phases where a portion of the in-vivo region is taken by the cutting unit 20c of the capsule medical device 2 according to the first embodiment. FIG. 7 is a schematic diagram illustrating phases where the mass of body tissue is cut out and obtained from the in-vivo region by the cutting unit 20c of the capsule medical device 2 according to the first embodiment. FIG. 8 is a schematic diagram illustrating a phase where the mass of body tissue is stored in a storage unit of the capsule medical device according to the first embodiment.

When the capsule medical device 2 inside the subject 1 reaches the in-vivo region to be examined (e.g., a lesion or the like inside the digestive organs such as the stomach, the small intestine, and the large intestine), the magnetic-field generating unit 5 described above applies a gradient magnetic field H1 and a rotating magnetic field H2 to the capsule medical device 2. In the capsule medical device 2, when the magnetic sensor 25 detects the gradient magnetic field H1 and the rotating magnetic field H2 generated by the magnetic-field generating unit 5, the control unit 28 controls the driving unit 26 to move the outer covering 20d at the timing when the gradient magnetic field and the rotating magnetic field are detected by the magnetic sensor 25 so that the cutting unit 20c is exposed to the in-vivo region of the subject 1.

The capsule medical device 2 in the above state forces the cylindrical casing 20a into the in-vivo region of the subject 1 due to the function of the magnet 24 guided by the gradient magnetic field H1 (see FIG. 3). As shown in FIG. 6, the gradient magnetic field H1 forces the cutting unit 20c with the cylindrical casing 20a into the in-vivo region of the subject 1. As a result, the cutting unit 20c is absorbed a little into the in-vivo region, and a portion of the in-vivo region is taken into the cylindrical casing 20a through the opening 20e (phase A1).

The capsule medical device 2 rotates along the circumferential direction of the capsule-shaped casing 20 due to function of the magnet 24 influenced by the rotating magnetic field H2. As shown in FIG. 6, the cutting unit 20c takes a portion of the in-vivo region of the subject 1, and rotates with the cylindrical casing 20a along the circumferential direction of the capsule-shaped casing 20 due to the rotating magnetic field H2. As a result, the portion of in-vivo region is taken into the inside of the cylindrical casing 20a (phase A2).

Then, the capsule medical device 2 keeps rotating along the circumferential direction of the capsule-shaped casing 20 due to function of the magnet 24 influenced by the rotating magnetic field H2. The cutting unit 20c maintains inertia for the capsule medical device 2 to remain rotating along the circumferential direction. The cutting unit 20c converts the torque generated by the magnet 24 described above into the cutting force, and strengthens the cutting force to cut out and obtain a mass of body tissue 15 from the portion of in-vivo region taken as described into the inside of the cylindrical casing 20a as shown in FIG. 7 (phase A3).

Further, the capsule medical device 2 keeps rotating along the circumferential direction of the capsule-shaped casing 20 due to function of the magnet 24 influenced by the rotating magnetic field H2. As shown in FIG. 7, the mass of body tissue 15 which is cut out and obtained by the cutting unit 20c falls down toward the storage unit 27, pushes and open the lid parts 27c, 27d with the weight of the mass of body tissue 15, and enters the inside of the storage unit 27 (phase A4).

Then, the lid parts 27c, 27d are closed as shown in FIG. 8. As a result, the storage unit 27 stores the mass of body tissue 15, and prevents the mass of body tissue 15 from dropping out (phase A5). After that, the capsule medical device 2 having the mass of body tissue 15 stored in the storage unit 27 is no longer affected by the gradient magnetic field H1 and the rotating magnetic field H2, and is naturally excreted outside the subject 1 due to the peristalsis and the like. After the capsule medical device 2 is naturally excreted outside the subject 1, the mass of body tissue 15 in the storage unit 27 is taken by the doctor, the nurse, or the like, and used for the biopsy such as the pathological diagnosis.

In the capsule medical device 2, the external gradient magnetic field forces the capsule-shaped casing 20 into the in-vivo region, and the external rotating magnetic field rotates the cutting unit 20c along the circumferential direction of the capsule-shaped casing 20. Thus, the capsule medical device 2 can maintain rotation inertia for the cutting unit 20c to remain rotating along the circumferential direction of the capsule-shaped casing 20, and can convert the torque along the circumferential direction generated by the magnet 24 rotating along the circumferential direction of the capsule-shaped casing 20 into cutting force of the cutting unit 20c. Thus, the cutting force of the cutting unit 20c can be properly strengthened even in a small space such as the small intestine and the large intestine. The cutting force of the cutting unit 20c strengthened as described above is much stronger than that of the forceps and the like of the conventional capsule medical device where a straight-line stroke of the forceps to be extended and withdrawn from the capsule-shaped casing is limited in a small space due to a size of the capsule-shaped casing. Thus, the cutting force is made strong enough to securely cut out and obtain a mass of body tissue (the mass of body tissue 15) from the in-vivo region of the subject 1.

The mass of body tissue 15 which is cut out and obtained by the capsule medical device is large enough to be used as a sample for the biopsy. The biopsy such as the pathological diagnosis using the mass of body tissue 15 can enhance accuracy of the biopsy, and provide abundant medical information which is hard to obtain with a small amount of the body tissue such as a cross-sectional view of the body tissue in the in-vivo region to be examined.

The capsule medical device 2 described above has the capsule-shaped casing 20 rotated along the circumferential direction less than one revolution, and the cutting unit 20c rotates along the circumferential direction with the capsule-shaped casing 20 rotating less than one revolution in order to obtain the cutting force of the cutting unit 20c to securely cut out and obtain the mass of body tissue 15 from the in-vivo region. Further, the number of revolutions of the cutting unit 20c may be increased to further strengthen the cutting force of the cutting unit 20c. Specifically, in the capsule medical device 2, the capsule-shaped casing 20 keeps rotating up to one or more revolutions along the circumferential direction of the capsule-shaped casing 20 due to the external rotating magnetic-field, and the number of revolutions of the cutting unit 20c rotating along the circumferential direction of the capsule-shaped casing 20 is increased to one or more. Thus, an amount of movement of the cutting unit 20c cutting out and obtaining the mass of body tissue can be increased up to infinity (equal to or longer than a length of the circumference along the circumferential direction of the capsule-shaped casing 20) along the circumferential direction of the capsule-shaped casing 20. As a result, the capsule medical device 2 can further strengthen the cutting force of the cutting unit 20c compared with the case where the number of revolutions of the capsule-shaped casing 20 is less than one, whereby the mass of body tissue 15 can be even more securely cut out and obtained from the in-vivo region.

As described above, according to the first embodiment of the present invention, the cutting unit is fixated on the capsule-shaped casing with the edge of the cutting unit arranged in the circumferential direction of the capsule-shaped casing 20. The rotation driving unit arranged inside the capsule-shaped casing generates the torque along the circumferential direction of the capsule-shaped casing. The cutting unit rotates with the capsule-shaped casing along the circumferential direction of the capsule-shaped casing due to the generated torque. The cutting unit rotating along the circumferential direction cuts out and obtains the mass of body tissue from the in-vivo region of the subject. Thus, the rotation inertia of the cutting unit can be maintained, and the torque of the capsule-shaped casing along the circumferential direction can be converted into the cutting force of the cutting unit. Thus, the cutting force of the cutting unit can be properly strengthened, for example, even in the small space inside the body such as is the case with the small intestine and the large intestine. As a result, the cutting force can be much stronger than that of the forceps and the like in the conventional capsule medical device where the straight-line stroke of the forceps to be extended and withdrawn from the capsule-shaped casing is limited in a small space due to a size of the capsule-shaped casing. Thus, the capsule medical device and the body-tissue obtaining method can securely cut out and obtain the mass of body tissue being of size needed for the biopsy from the desired in-vivo region of the subject.

Further, as the rotation driving unit which generates the torque along the circumferential direction of the capsule-shaped casing, the magnet magnetized in the radial direction of the capsule-shaped casing is arranged inside the capsule-shaped casing so as to rotate the capsule-shaped casing with the magnet due to the external rotating magnetic field and rotate the cutting unit with the capsule-shaped casing along the circumferential direction. Thus, the power source for rotating the cutting unit along the circumferential direction is not necessarily arranged in the capsule-shaped casing, whereby the capsule medical device can be further downsized, and power consumption of the capsule medical device can be reduced.

The external gradient magnetic field forces the capsule-shaped casing with the magnet into the in-vivo region of the subject, whereby the cutting unit can be forced into the in-vivo region without increasing the power consumption of the capsule medical device, and the portion of in-vivo region can be easily taken into the capsule-shaped casing by the cutting unit. As a result, the mass of body tissue can be easily cut out and obtained from the captured portion of in-vivo region by the cutting unit.

A first modification of the first embodiment of the present invention is described. In the first embodiment described above, the cutting unit 20c rotates along the circumferential direction of the capsule-shaped casing 20 due to the external rotating magnetic field. In the first modification of the first embodiment, however, the cutting unit is arranged on an exterior which can be rotated along the circumferential direction of the capsule-shaped casing, and the cutting unit rotates with the exterior driving force (torque) of a motor to cut out and obtain the mass of body tissue from the in-vivo region.

Figure 9:
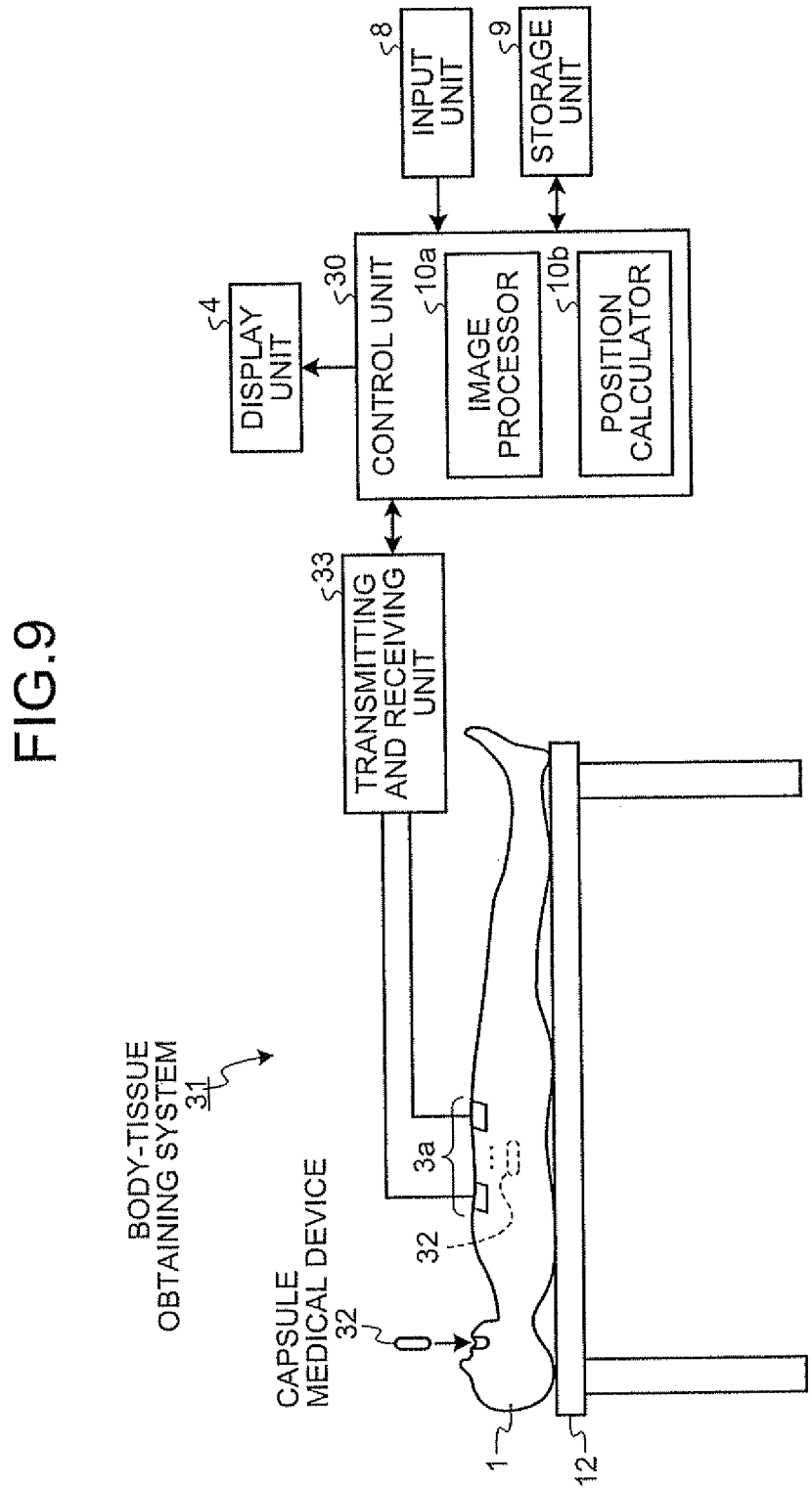
FIG. 9 is a block diagram of an example configuration of a body-tissue obtaining system according to a first modification of the first embodiment of the present invention.

FIG. 9 is a block diagram of an example configuration of a body-tissue obtaining system according to the first modification of the first embodiment of the present invention. As shown in FIG. 9, a body-tissue obtaining system 31 according to the first modification includes a capsule medical device 32 instead of the capsule medical device 2 of the body-tissue obtaining system 11 according to the first embodiment described above, a transmitting and receiving unit 33 instead of the receiving unit 3, and a control unit 30 instead of the control unit 10. Further, the body-tissue obtaining system 31 does not include the magnetic-field generating unit 5, the power supply unit 6, and the moving unit 7. The body-tissue obtaining system 31 includes components identical with those of the first embodiment other than those described above. Same numerals denote identical components.

The capsule medical device 32 is introduced into the subject 1 similarly to the capsule medical device 2 according to the first embodiment described above. The capsule medical device 32 successively captures the in-vivo images of the subject 1 while moving through the digestive organs of the subject 1 due to the peristalsis and the like, and wirelessly transmits the image signal including the acquired in-vivo images to an outside of the subject 1 (specifically, the antenna 3a of the transmitting and receiving unit 33) successively as each of the in-vivo images is captured. Further, the capsule medical device 32 receives a control signal from the control unit 30 for controlling the capsule medical device 32 that is wirelessly transmitted from the transmitting and receiving unit 33 when reaching the desired in-vivo region inside the subject 1, and operates according to the received control signal. As a result, the mass of body tissue is cut out and obtained from the in-vivo region. The capsule medical device 32 having the obtained mass of body tissue stored in the capsule-shaped casing moves through the digestive organs of the subject 1 until naturally excreted outside the subject 1 at last. The configuration of the capsule medical device 32 is described in detail later.

The transmitting and receiving unit 33 is connected with the plural antennas 3a arranged on the body surface of the subject 1. The transmitting and receiving unit 33 transmits the wireless-transmission signal to the capsule medical device 32 inside the subject 1 via one of the antennas 3a. Specifically, the transmitting and receiving unit 33 acquires the control signal for controlling the capsule medical device 32 from the control unit 30, and performs a demodulation process and the like on the acquired control signal to generate the wireless transmission signal including the control signal. The transmitting and receiving unit 33 transmits the generated wireless-transmission signal to the capsule medical device 32 inside the subject 1 via the antenna 3a. Other functions of the transmitting and receiving unit 33 are identical with those of the receiving unit 3 of the body-tissue obtaining system 11 according to the first embodiment described above.

The control unit 30 does not include the magnetic-field generating unit 5, the power supply unit 6, and the moving unit 7. Instead, the control unit 30 makes the transmitting and receiving unit 33 wirelessly transmit the control signal to the capsule medical device 32 inside the subject 1, and controls the capsule medical device 32 inside the subject 1 according to the control signal. Specifically, when the capsule medical device 32 inside the subject 1 reaches the desired in-vivo region, the control unit 30 generates the control signal for the capsule medical device 32 inside the subject 1 based on the instruction information which is input from the input unit 8, and the control unit 30 transmits the generated control signal to the transmitting and receiving unit 33. Then, the control unit 30 controls the transmitting and receiving unit 33 to wirelessly transmit the control signal. The control signal generated by the control unit 30 instructs the capsule medical device 32 inside the subject 1 to cut out and obtain the mass of body tissue. Other functions of the control unit 30 are identical with those of the control unit 10 of the body-tissue obtaining system 11 according to the first embodiment except the control functions of the magnetic-field generating unit 5, the power supply unit 6, and the moving unit 7 described above.

Figure 10:
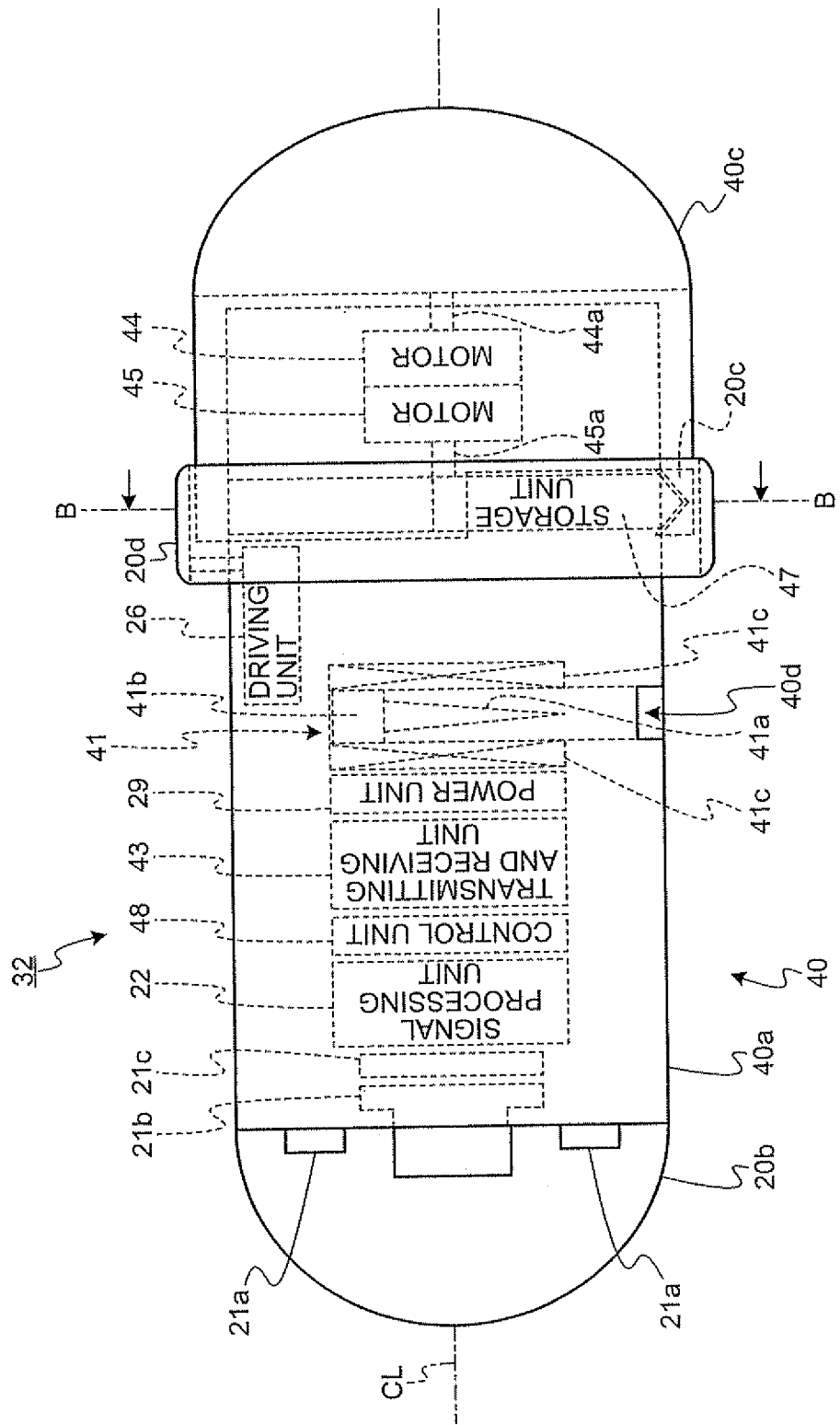
FIG. 10 is a schematic diagram of an example configuration of a capsule medical device according to a first modification of the first embodiment of the present invention.
Figure 11:
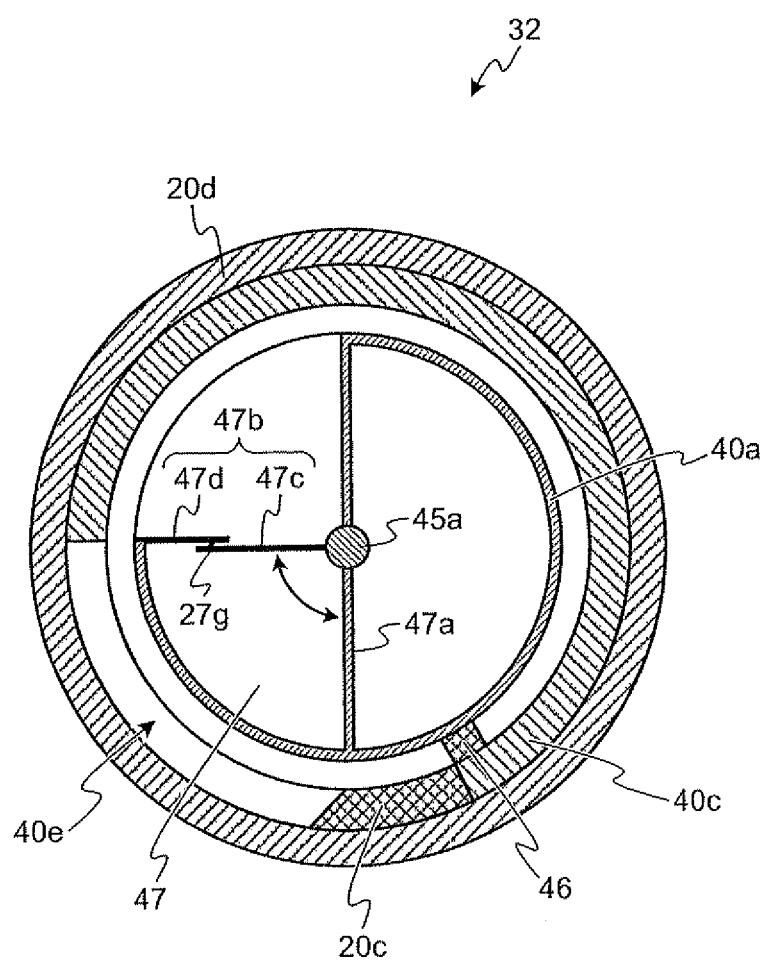
FIG. 11 is a schematic cross-sectional view taken along line B-B of a capsule medical device shown in FIG. 10.
Figure 12:
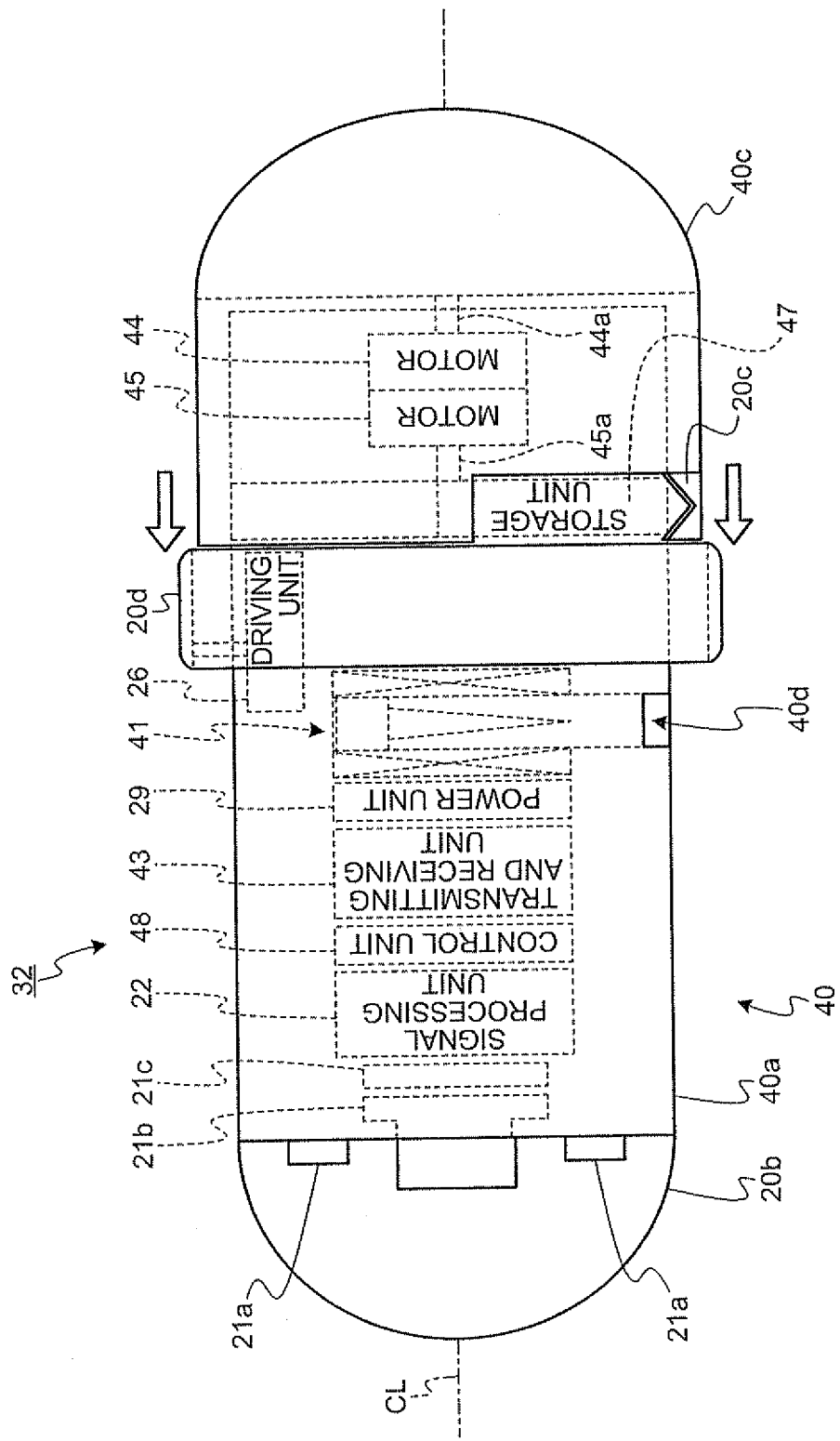
FIG. 12 is a schematic diagram illustrating a state where the cutting unit is exposed as the outer covering of the capsule medical device shown in FIG. 10 slides.

The configuration of the capsule medical device 32 according to the first modification is described in detail. FIG. 10 is a schematic diagram of an example configuration of the capsule medical device 32 according to the first modification of the first embodiment of the present invention. FIG. 11 is a schematic cross-sectional view taken along line B-B of the capsule medical device 32 shown in FIG. 10. FIG. 12 is a schematic diagram showing a state where the cutting unit is exposed as the outer covering of the capsule medical device 32 shown in FIG. 10 slides. As shown in FIGS. 10 to 12, the capsule medical device 32 according to the first modification includes a capsule-shaped casing 40 instead of the capsule-shaped casing 20 of the capsule medical device 2 according to the first embodiment described above, a transmitting and receiving unit 43 instead of the transmitting unit 23, a storage unit 47 instead of the storage unit 27, and a control unit 48 instead of the control unit 28. The capsule medical device 32 does not include the magnet 24 and the magnetic sensor 25 described above. Further, the capsule medical device 32 includes an exterior 40c which can be rotated along the circumferential direction of the capsule-shaped casing 40, a fixation unit 41 for temporarily fixing the capsule-shaped casing 40 on the in-vivo region, a motor 44 for rotating an exterior 40c along a circumferential direction of the capsule-shaped casing 40, and a motor 45 for driving an opening and closing of the storage unit 47. In the capsule medical device 32 according to the first embodiment, the cutting unit 20c is fixated on an edge of the exterior 40c with a blade of the cutting unit 20c facing in the circumferential direction of the capsule-shaped casing 40, and the outer covering 20d covers the cutting unit 20c fixated on the exterior 40c. Other components are identical with those of the first embodiment and same numerals are attached to identical components.

The capsule-shaped casing 40 is a capsule-shaped casing being of a size which can be introduced into the subject 1. The capsule-shaped casing 40 includes a cylindrical casing 40a instead of the cylindrical casing 20a of the capsule medical device 2 according to the first embodiment described above. The capsule-shaped casing 40 is formed as one end of the cylindrical casing 40a is sealed by a dome-shaped casing 20b and the exterior 40c is arranged on another end. The cylindrical casing 40a is substantially opaque casing. A concave part which communicates with the storage unit 47 described later is formed on a portion of the cylindrical casing 40a. The concave part of the cylindrical casing 40a is formed as a quarter of a circle is lacking, for example, as shown in a cross-sectional view of the cylindrical casing 40a shown in FIG. 11. The cylindrical casing 40a further has an opening 40d where a needle 41a of the fixation unit 41 described later is extended or withdrawn. Inside the capsule-shaped casing 40 formed by the cylindrical casing 40a and the dome-shaped casing 20b, the illuminating unit 21a, the optical system 21b, and the imaging unit 21c are arranged in the dome-shaped casing 20b while the signal processing unit 22, the transmitting and receiving unit 43, the driving unit 46, the fixation unit 41, the motors 44, 45, the control unit 48, and the power unit 29 are arranged in the cylindrical casing 40a.

The exterior 40c has a bottomed structure where a dome-shaped part is formed in an end of a cylindrical part. The exterior 40c is arranged rotatably on the cylindrical casing 40a and covers the end of the cylindrical casing 40a (the end on a side opposing to the dome-shaped casing 20b). A lacking part which is rectangular-shaped and cut out (lacking part 40a) is formed in a portion of the open end of the exterior 40c. The cutting unit 20c is fixated on an edge of the lacking part 40e. Further, the cutting unit 20c has the edge of the cutting unit facing along the circumferential direction of the capsule-shaped casing 40, i.e., the circumferential direction of the exterior 40c as described above. The exterior 40c rotates with the cutting unit 20c along the circumferential direction of the capsule-shaped casing 40 due to driving force (torque) of the motor 44 and opens or closes the concave part (a part communicating with the storage unit 47) of the cylindrical casing 40a described above.

The exterior 40c includes a stopper 46 on an inner wall surface near the cutting unit 20c as shown in FIG. 11. The stopper 46 is integrally formed with the inner wall of the exterior 40c. The stopper 46 slides on an outer wall of the cylindrical casing 40a, and rotates with the exterior 40c along the circumferential direction. The stopper 46 prevents the mass of body tissue which is cut out and obtained by the cutting unit 20c from entering the space between the cylindrical casing 40a and the exterior 40c.

The motor 44 functions as a rotation driving unit which generates torque along the circumferential direction of the capsule-shaped casing 40. Specifically, the motor 44 includes a rotation shaft 44a which is set parallel to the central shaft CL along the longitudinal direction of the capsule-shaped casing 40, and is connected with the exterior 40c via the rotation shaft 44a. The motor 44 is driven under the control by the control unit 48, and rotates with the exterior 40c along the circumferential direction of the capsule-shaped casing 40. The torque along the circumferential direction generated by the motor 44 is converted into the cutting force via the cutting unit 20c rotating with the exterior 40c along the circumferential direction.

The motor 45 is a driving source which generates driving force for driving the opening and the closing of the storage unit 47. Specifically, the motor 45 includes, for example, a rotation shaft 45a parallel to the central shaft CL, and is connected with the storage unit 47 (specifically, a lid part 47c of an opening-closing part 47b shown in FIG. 11) via the rotation shaft 45a. The motor 45 drives the opening and the closing of the lid part 47c of the storage unit 47 under the control by the control unit 48.

The fixation unit 41 is a system for fixating the capsule-shaped casing 40 on the in-vivo region when the exterior 40c described above rotates along the circumferential direction. Specifically, the fixation unit 41 includes a needle 41a which punctures the in-vivo region of the subject 1, a base 41b made of a magnetic material, and a solenoid 41c. The needle 41a is arranged in the cylindrical casing 40a in a manner such that the needle 41a can be extended and withdrawn from the opening 40d. A base end of the of the needle 41a (an end opposing to a pointed tip end) is fixated on the base 41b. The base 41b, reacting to the magnetic field generated by the solenoid 41c, is reciprocated along the radial direction of the capsule-shaped casing 40. Thus, the needle 41a is extended out of the capsule-shaped casing 40 from the opening 40d to puncture the in-vivo region of the subject 1. As a result, the fixation unit 41 can fixate the capsule-shaped casing 40 on the in-vivo region of the subject 1. On the other hand, the needle 41a is withdrawn to be stored in the capsule-shaped casing 40 due to the reciprocating of the base 41b. As a result, the fixation unit no longer fixates the capsule-shaped casing 40 on the in-vivo region as the needle 41a no longer punctures the in-vivo region. The transmitting and receiving unit 43 receives the wireless transmission signal transmitted via the antenna 3a described above from the transmitting and receiving unit 33 arranged outside, and performs the predetermined demodulation process or the like on the received wireless-transmission signal to obtain (demodulate) the control signal included in the wireless-transmission signal. The demodulated control signal is generated by the above-described control unit 30 arranged outside, and instructs the capsule medical device 32 to cut out and obtain the mass of body tissue. Other functions of the transmitting and receiving unit are identical with those of the transmitting unit 23 of the capsule medical device 2 according to the first embodiment described above.

The control unit 48 acquires the control signal generated by the above-described control unit 30 arranged outside from the transmitting and receiving unit 43, and controls each operation for cutting out and obtaining the mass of body tissue from the in-vivo region of the subject 1 based on the acquired control signal. Specifically, the control unit 48 controls the driving of the driving unit 26, the fixation unit 41, and the motor 44 based on the control signal. Due to the control by the control unit 48, the driving unit 26 moves the outer covering 20d in a direction along the central shaft CL so that the edge of the exterior 40c and the cutting unit 20c are exposed to the in-vivo region of the subject 1. Then, the fixation unit 41 has the needle 41a puncture the in-vivo region of the subject 1 to fixate the capsule-shaped casing 40 on the in-vivo region, and the motor 44 rotates the exterior 40c and the cutting unit 20c along the circumferential direction of the capsule-shaped casing 40. Further, the control unit 48 controls the motor 45 a predetermined time period after the motor 44 starts to be controlled, and the motor 45 opens and closes the opening-closing part 47b of the storage unit 47 under the control by the control unit 48.

The control unit 48 controls each driving of the driving unit 26, the fixation unit 41, and the motor 44 a predetermined time after the control signal is acquired from the transmitting and receiving unit 43. Due to the control by the control unit 48, the motor 44 stops being driven so that the exterior 40c and the cutting unit 20c are no longer rotated, and the fixation unit 41 withdraws the needle 41a into the capsule-shaped casing 40 so that the capsule-shaped casing 40 is no longer fixated on the in-vivo region, and the driving unit 26 moves the outer covering 20d in the direction along the central shaft CL so that the edge of the exterior 40c and the cutting unit 20c are covered by the outer covering. Other functions of the control unit 48 are identical with those of the control unit 28 of the capsule medical device 2 according to the first embodiment described above.

The storage unit 47 stores the mass of body tissue which is cut out and obtained by the cutting unit 20c described above. As shown in FIGS. 10 to 12, the storage unit 47 is arranged in the concave part of the capsule-shaped casing 40. The storage unit 47 is arranged inside the cylindrical casing 40a and separated from the built-in components of the capsule medical device 32 (specifically, electrical components such as the imaging unit 21c and the control unit 48, the power unit 29 such as the battery, the fixation unit 41, and the like). The storage unit 47 is formed by a wall part 47a and an opening-closing part 47b. The storage unit 47 stores the mass of body tissue in a space surrounded by the wall part 47a, the opening-closing part 47b, and a portion of the cylindrical casing 40a.

The opening-closing part 47b opens inward and includes a lid part 47c, a wall part 47d, and a sealing member 27g which securely seals up the closed lid part 47c and the wall part 47d. Specifically, the lid part 47c is supported by the rotation shaft 45a of the motor 45, and closes or opens inward in the storage unit 47 due to the driving force of the motor 45 with the rotation shaft 45a being a supporting point. The wall part 47d is fixated on the cylindrical casing 40a. The wall part 47d and the lid part 47c together close the storage unit 47. The sealing member 27g is arranged on a surface of the lid part 47c which is on a side opposing to the wall part 47d in a closed state. The sealing member 27g water-tightly seals up the lid part 47c and the wall part 47d in the closed state.

In the body-tissue obtaining system 31 shown in FIG. 9, the capsule medical device 32 having the configuration above is introduced into the subject 1, moves through the digestive organs of the subject due to the peristalsis and the like, and reaches the in-vivo region to be examined. Then, the user controls the input unit 8 to instruct the capsule medical device 32 inside the subject 1 to cut out and obtain the mass of body tissue, and at the same time, the user refers to the in-vivo image and the current position information displayed on the display unit 4. The control unit 30 generates the control signal for the capsule medical device 32 based on the instruction information which is input from the input unit 8. The transmitting and receiving unit 33 wirelessly transmits the control signal from the control unit 30 to the capsule medical device 32 inside the subject via the antenna 3a.

The capsule medical device 32 inside the subject 1 operates according to the control signal, and cuts out and obtains the mass of body tissue from the in-vivo region of the subject 1. The mass of body tissue is stored in the storage unit 47 of the capsule medical device 32. Then, the capsule medical device 32 inside the subject a moves through the digestive organs due to the peristalsis and the like until naturally excreted outside the subject 1 at last. The mass of body tissue stored in the storage unit 47 of the capsule medical device 32 is taken by the doctor, the nurse, or the like, and used for the biopsy such as the pathological diagnosis.

Figure 13:
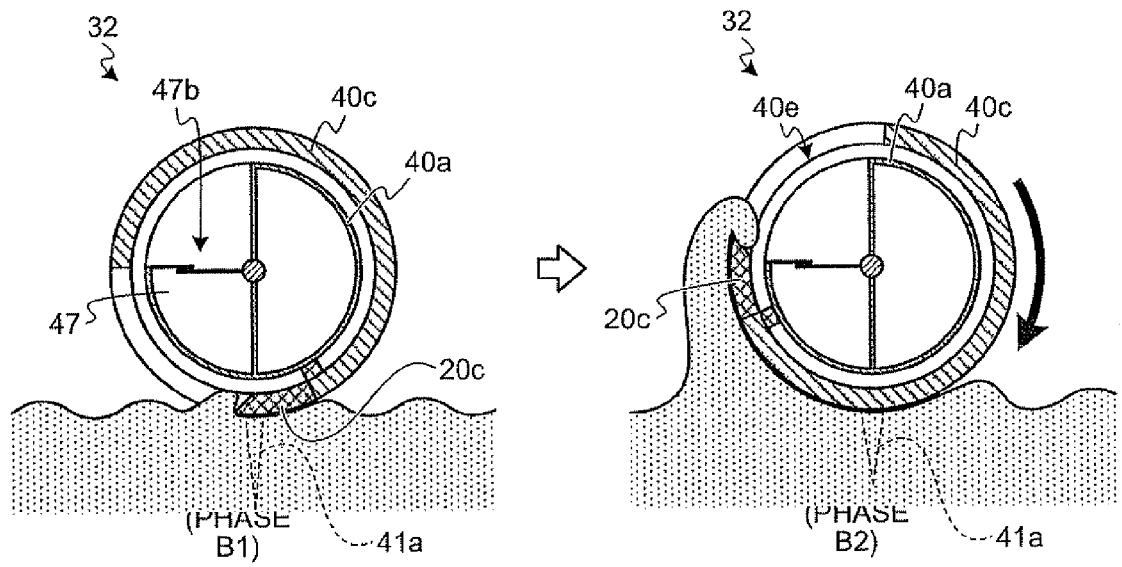
FIG. 13 is a schematic diagram illustrating phases where the cutting unit of the capsule medical device according to the first modification of the first embodiment takes a portion of the in-vivo region.
Figure 14:
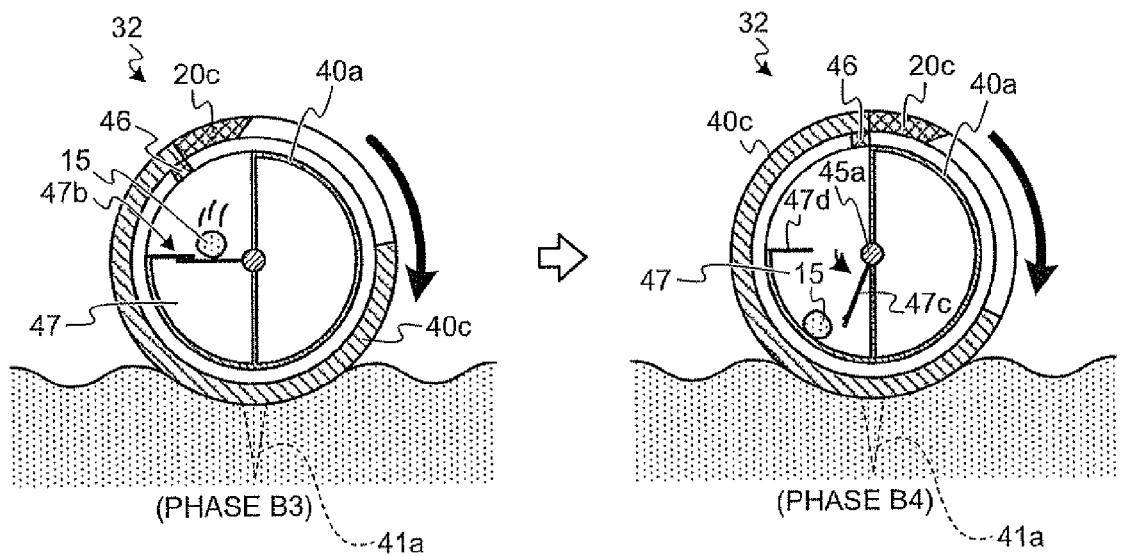
FIG. 14 is a schematic diagram illustrating phases where the cutting unit of the capsule medical device according to the first modification of the first embodiment cuts out and obtains a mass of the body tissue from the in-vivo region.

The operation of the capsule medical device 32 for cutting out and obtaining the mass of body tissue from the in-vivo region of the subject 1 is described, FIG. 13 is a schematic diagram illustrating phases where the portion of the in-vivo region is taken by the cutting unit 20c of the capsule medical device 32 according to the first modification of the first embodiment. FIG. 14 is a schematic diagram illustrating phases where the mass of body tissue is cut out and obtained from the in-vivo region by the cutting unit 20c of the capsule medical device 32 according to the first modification of the first embodiment.

The capsule medical device 32 inside the subject 1 acquires the control signal from the control unit 30 arranged outside when the capsule medical device 32 reaches the in-vivo region to be examined. Based on the acquired control signal, the capsule medical device 32 performs a series of operations for cutting out and obtaining the mass of body tissue. The capsule medical device 32 moves the outer covering 20d by the driving force of the driving unit 26 so that the edge of the exterior 40c and the cutting unit 20c are exposed to the in-vivo region of the subject 1. Further, the capsule medical device 32 punctures the in-vivo region of the subject 1 with the needle 41a. Then, the capsule medical device 32 forces the cutting unit 20c into the in-vivo region of the subject 1 and fixates the cylindrical casing 40a on the in-vivo region with the needle 41a (phase B1).

In the capsule medical device 32, the cylindrical casing 40a remains being fixated on the in-vivo region of the subject 1 while the exterior 40c is rotated along the circumferential direction of the capsule-shaped casing 40 (a direction along the arrow shown in FIG. 13) due to the torque along the circumferential direction generated by the above-described motor 44. As shown in FIG. 13, the cutting unit 20c takes the portion of the in-vivo region of the subject 1, and rotates with the exterior 40c along the circumferential direction of the capsule-shaped casing 40 due to the torque along the circumferential direction. As a result, the portion of the in-vivo region is taken into the lacking part 40e of the exterior 40c (phase B2).

The capsule medical device 32 remains rotating the exterior 40c. The cutting unit 20c maintains the inertia to rotate along the circumferential direction of the capsule-shaped casing 40, and converts the torque along the circumferential direction generated by the motor 44 into the cutting force. Thus, the cutting force is strengthened, and as shown in FIG. 14, the mass of body tissue 15 is cut out and obtained from the portion of the in-vivo region captured into the lacking part 40e as described (phase B3). The stopper 46 slides on the outer wall surface of the cylindrical casing 40a, and rotates with the exterior 40c along the circumferential direction so as to prevent the mass of body tissue from entering the space between the outer wall surface of the cylindrical casing 40a and the inner wall surface of the exterior 40c. The function of the stopper 46 prevents the mass of body tissue 15 from being sandwiched between the outer wall surface of the cylindrical casing 40a and the inner wall surface of the exterior 40c. The mass of body tissue falls toward the opening-closing part 47b of the storage unit 47.

The capsule medical device 32 then drives the above-described motor 45 while remaining rotating the exterior 40c. The storage unit 47 rotates the lid part 47c with the rotation shaft 45a inward by the driving force of the motor 45, whereby the storage unit 47 switches to a opened state. The mass of body tissue 15 enters the storage unit 47, which is in the open state (phase B4). The storage unit 47 storing therein the mass of body tissue 15 rotates the lid part 47c toward the wall part 47d by the driving force of the motor 45, whereby the storage unit 47 switches to a closed state. As a result, the storage unit 47 can store the mass of body tissue 15 with the mass of body tissue 15 prevented from dropping out.

The capsule medical device 32 having the mass of body tissue 15 stored in the storage unit 47 withdraws the needle 41a into the cylindrical casing 40a so that the capsule medical device 32 is no longer fixated on the in-vivo region. The capsule medical device 32 ceases to rotate the exterior 40c, and covers the edge of the exterior 40c, and the cutting unit 20c with the outer covering 20d. The capsule medical device 32 in the state above moves through the digestive organs due to the peristalsis and the like until naturally excreted outside the subject 1 at last. After the capsule medical device 32 is naturally excreted outside the subject 1, the mass of body tissue 15 inside the storage unit 47 is taken by the doctor, the nurse, and the like, and used for the biopsy such as the pathological diagnosis.

When the capsule medical device 32 cuts out and obtains the mass of body tissue from the in-vivo region of the subject 1 with the cutting unit 20c, the needle 41a punctures the in-vivo region to fixate the capsule-shaped casing 40 on the in-vivo region, and the cutting unit 20c is rotated along the circumferential direction of the capsule-shaped casing 40 by the torque of the motor 44 along the circumferential direction. Thus, the capsule medical device 32 maintains the rotation inertia for the cutting unit 20c to remain rotating along the circumferential direction of the capsule-shaped casing 40, and converts the torque along the circumferential direction generated by the motor 44 into the cutting force of the cutting unit 20c. Thus, the cutting force of the cutting unit 20c can be properly strengthened even in a small space such as the small intestine and the large intestine. The cutting force which is strengthened as above is much stronger than that of the forceps and the like of the conventional capsule medical device where the straight-line stroke of the forceps to be extended and withdrawn from the capsule-shaped casing is limited in a small space due to the size of the capsule-shaped casing. The cutting force is strong enough to be able to cut out and obtain the mass of body tissue (the mass of body tissue 15) from the in-vivo region of the subject 1.

The mass of body tissue cut out and obtained by the capsule medical device 32 is of a size which is large enough to be used as a sample of the biopsy similarly to that of the first embodiment described above. The biopsy such as the pathological diagnosis using the mass of body tissue 15 can enhance accuracy of the biopsy, and provide abundant medical information which is hard to obtain with a small amount of the body tissue such as a cross-sectional view of the body tissue in the in-vivo region to be examined.

The capsule medical device 32 described above has the exterior 40c rotated less than one revolution, and the cutting unit 20c rotates along the circumferential direction with the exterior 40c rotating less than one revolution in order to obtain the cutting force of the cutting unit 20c to securely cut out and obtain the mass of body tissue 15 from the in-vivo region. Further, the number of revolutions of the cutting unit 20c may be increased to further strengthen the cutting force of the cutting unit 20c. Specifically, the capsule medical device 32 keeps rotating up to one or more revolutions along the circumferential direction of the exterior 40c due to the torque of the motor 44 (driving force), and the number of revolutions of the cutting unit 20c rotating along the circumferential direction can be increased to one or more. Thus, an amount of movement of the cutting unit 20c cutting out and obtaining the mass of body tissue can be increased up to infinity (equal to or longer than a length of the circumference along the circumferential direction of the capsule-shaped casing 40) along the circumferential direction of the capsule-shaped casing 40. As a result, the capsule medical device 32 can further strengthen the cutting force of the cutting unit 20c compared with the case where the number of revolutions of the capsule-shaped casing 40 is less than one, whereby the mass of body tissue 15 can be even more securely cut out and obtained from the in-vivo region.

As described above, in the first modification of the first embodiment of the present invention, the cutting unit is fixated on the exterior of the capsule-shaped casing with the blade of the cutting unit facing in the circumferential direction of the capsule-shaped casing, the rotation driving unit arranged inside the capsule-shaped casing generates the torque along the circumferential direction of the capsule-shaped casing, the torque rotates the cutting unit together with the exterior along the circumferential direction of the capsule-shaped casing, and the mass of body tissue is cut out and obtained from the in-vivo region of the subject by the cutting unit rotating along the circumferential direction. Other configurations are identical with those of the first embodiment. Thus, similarly to the first embodiment described above, the rotation inertia of the cutting unit can be maintained, and the torque along the circumferential direction can be converted into the cutting force of the cutting unit. Thus, the cutting force of the cutting unit can be properly strengthened even in the small space such as the small intestine and the large intestine. As a result, the capsule medical device and the body-tissue obtaining method which can provide the advantage similarly to that of the first embodiment described above can be realized.

Further, the capsule-shaped casing is fixated on the in-vivo region as the needle extended out of the capsule-shaped casing punctures the in-vivo region, whereby the external gradient magnetic field is no longer required (i.e., the magnetic-field generating unit is no longer required), and the heavy magnet is no longer required to be arranged inside the capsule-shaped casing. As a result, the capsule-shaped casing can be further downsized, the capsule-shaped casing can be easily fixated on the in-vivo region with a simple configuration, and the operation for relatively rotating the exterior and the cutting unit to the capsule-shaped casing can be easily realized.

A second modification of the first embodiment of the present invention is described. In the first embodiment described above, the cutting unit 20c, which is a blade, is used for cutting out and obtaining the mass of body tissue from the in-vivo region. In the second modification of the first embodiment, however, a hollow needle whose pointed tip end and base end are communicated with each other via a communicating hole is used for cutting out and obtaining the mass of body tissue from the in-vivo region.

Figure 15:
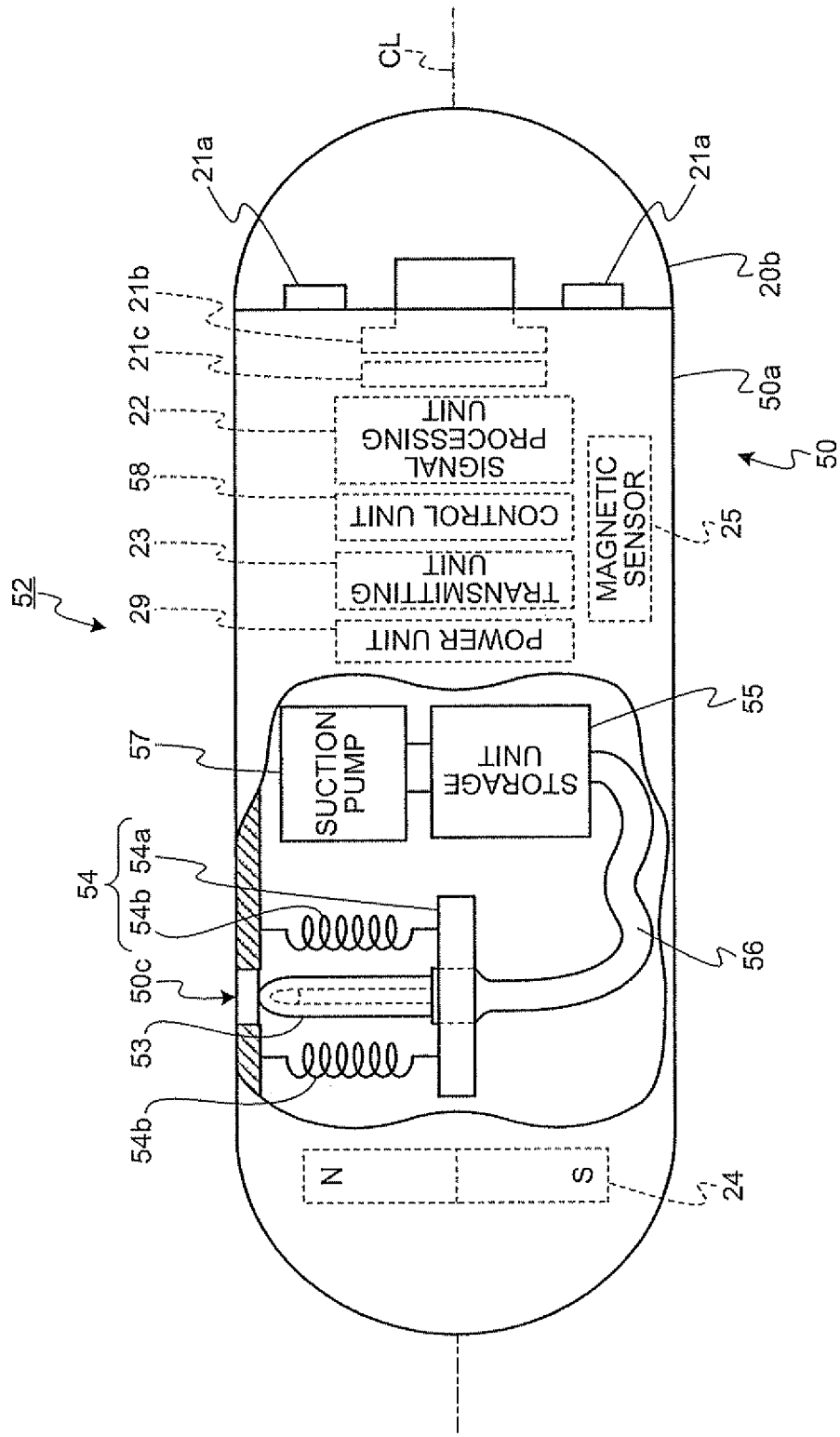
FIG. 15 is a schematic diagram of an example configuration of a capsule medical device according to a second modification of the first embodiment.
Figure 16:
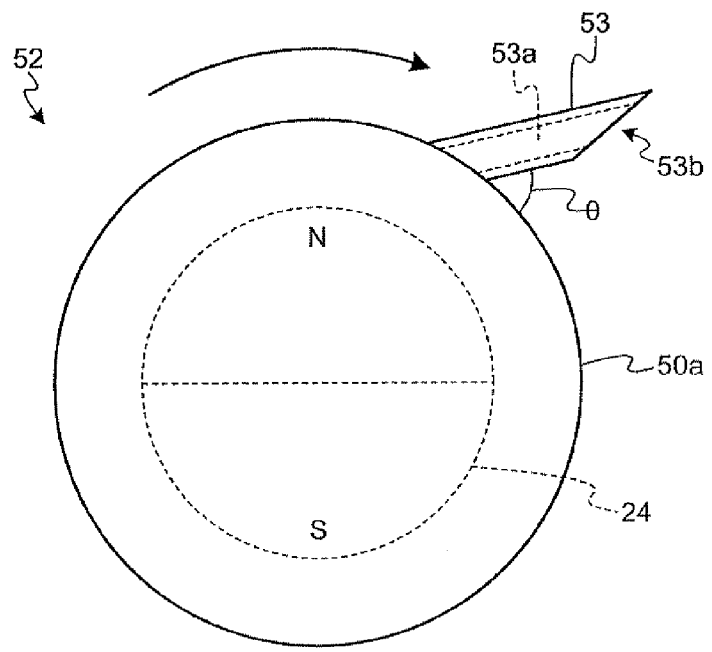
FIG. 16 is a schematic diagram of a capsule medical device taken along a longitudinal direction of a capsule-shaped casing.

FIG. 15 is a schematic diagram of an example configuration of a capsule medical device according to the second modification of the first embodiment of the present invention. FIG. 16 is a schematic diagram of the capsule medical device taken along a longitudinal direction of a capsule-shaped casing. FIG. 15 shows the capsule medical device a part of which is broken so that an inner configuration of the capsule medical device according to the second modification can be easily described. FIG. 16 shows the capsule medical device whose hollow needle extends outside to cut out and obtain the mass of body tissue.

As shown in FIGS. 15 and 16, a capsule medical device 52 according to the second modification of the first embodiment includes a capsule-shaped casing 50 instead of the capsule-shaped casing 20 of the capsule medical device 2 according to the first embodiment described above, a hollow needle 53 instead of the cutting unit 20c, a storage unit 55 instead of the storage unit 27, and a control unit 58 instead of the control unit 28. The capsule medical device 52 does not include the outer covering 20d and the driving unit 26 described above. Further, the capsule medical device includes an extending-withdrawing system 54 which extends and withdraws the hollow needle 53 from the capsule-shaped casing 50, a tube 56 through which the hollow needle 53 and the storage unit 55 are communicated with each other, and a suction pump 57 which sucks out the mass of body tissue, which is cut out and obtained by the hollow needle 53, into the storage unit 55. A body-tissue obtaining system according to the second modification of the first embodiment includes the capsule medical device 52 instead of the capsule medical device 2 of the body-tissue obtaining system 11 (see FIG. 1) according to the first embodiment described above. Other configurations are identical with those of the first embodiment, and same numerals denote the identical components.

The capsule-shaped casing 50 is of a size which can be introduced into the subject 1. The capsule-shaped casing 50 includes a cylindrical casing 50a instead of the cylindrical casing 20a of the capsule medical device 2 according to the first embodiment described above. The capsule-shaped casing 50 is formed as one end (open end) of the cylindrical casing 50a whose another end is dome-shaped is sealed by the dome-shaped casing 20b. The cylindrical casing 50a is substantially opaque. An opening 50c from which the hollow needle 53 is extended and withdrawn (extending-withdrawing) is formed on a portion of the cylindrical casing 50a. In the capsule-shaped casing 50 formed by the cylindrical casing 50a and the dome-shaped casing 20b, the dome-shaped casing 20b includes the illuminating unit 21a, the optical system 21, and the imaging unit 21c while the cylindrical casing 50a includes the signal processing unit 22, the transmitting unit 23, the magnet 24, the magnetic sensor 25, the hollow needle 53, the extending-withdrawing system 54, the storage unit 55, the tube 56, the suction pump 57, the control unit 58, and the power unit 29.

The hollow needle 53 works as a cutting-obtaining function, and cuts out and obtains the mass of body tissue from the in-vivo region of the subject 1. Specifically, the hollow needle 53 includes a communicating hole 53a through which the pointed tip end and the base end are communicated with each other, and the hollow needle 53 is extended and withdrawn from the opening 50c of the capsule-shaped casing 50 under the operation of the extending-withdrawing system 54. The hollow needle 53 makes an acute angle θ with respect to a rotational direction (a direction along the arrow shown in FIG. 16) of the capsule-shaped casing 50 rotating due to the torque of the magnet 24 described above. The hollow needle 53 is extended with a tilted surface 53b of the tip end facing in the rotational direction. When the tilted surface 53b of the hollow needle 53 faces in the rotational direction of the capsule-shaped casing 50, a normal direction of the tilted surface 53b makes an acute angle with respect to the rotational direction of the capsule-shaped casing 50. The hollow needle 53 extended out of the capsule-shaped casing 50 rotates with the cylindrical casing 50a along the circumferential direction of the capsule-shaped casing 50 to cut out the mass of body tissue from the in-vivo region and obtain the same by capturing the same into the communicating hole 53a.

The extending-withdrawing system 54 extends or withdraws (extending-withdrawing) the hollow needle 53 from the opening 50c of the capsule-shaped casing 50. Specifically, the extending-withdrawing system 54 includes a supporting unit 54a which supports the base end of the hollow needle 53, and an SMA coil 54b which generates driving force for extending and withdrawing the hollow needle 53. The SMA coil 54b is made of a shape-memory alloy which has a predetermined shape-memory function and a predetermined electrical resistance. One end of the SMA coil 54b is fixated on the inner wall of the cylindrical casing 50a while another end is fixated on the supporting unit 54a. The SMA coil 54b is made long enough to store the hollow needle in the cylindrical casing 50a under a temperature lower than a predetermined temperature (the predetermined temperature is, for example, a temperature similar to that inside the subject). On the other hand, under a temperature higher than the predetermined temperature, i.e., under a temperature much higher than the temperature inside the subject, the SMA coil 54b shrinks to move the supporting unit 54a closer to the inner wall surface of the cylindrical casing 50a. Thus, the SMA coil 54b moves the supporting unit 54a closer to the inner wall surface of the cylindrical casing 50a by the driving force, and extends the hollow needle 53 out of the cylindrical casing 50a. Then, the SMA coil 54b moves the supporting unit 54a away from the inner-wall surface of the cylindrical casing 50a to withdraw (store) the hollow needle 53 into the cylindrical casing 50a.

The storage unit 55 stores the mass of body tissue which is cut out and obtained by the hollow needle 53, and is arranged inside the cylindrical casing 50a as shown in FIG. 15. An inside of the storage unit 55 is separated from the built-in components of the capsule medical device 52 (specifically, the electrical components such as the imaging unit 21c and the control unit 58, the power unit 29 such as the battery, the magnet, the extending-withdrawing system 54, and the like). The storage unit 55 is communicated with the suction pump 57 via a predetermined communicating pipe, and communicated with the hollow needle 53 via the tube 56. The storage unit 55 takes and stores the mass of body tissue which is sucked out into the hollow needle 53 by sucking force of the suction pump 57.

The tube 56 is made flexible. One end of the tube 56 is connected with the base end of the hollow needle 53 while another end is connected with the storage unit 55. The communicating hole 53a of the hollow needle 53 and the storage unit 55 are communicated with each other via the tube 56. The suction pump 57 sucks out the mass of body tissue inside the hollow needle 53 into the storage unit 55 by applying a negative pressure to the inside of the storage unit 55.

When the control unit 58 acquires the detection signal indicating that the external magnetic field is detected from the magnetic sensor 25, the control unit 58 controls the extending-withdrawing system 54 to extend the hollow needle 53 out of the capsule-shaped casing 50. Specifically, the control unit 58 supplies an electric current for the SMA coil 54b at the timing when the control unit 58 acquires the detection signal from the magnetic sensor 25, so that the SMA coil 54b shrinks to extend the hollow needle 53 out of the capsule-shaped casing 50. The control unit 58 controls the suction pump 57 to suck out the mass of body tissue from the inside of the hollow needle 53 into the storage unit 55. On the other hand, a predetermined time period after the control unit 58 acquires the detection signal from the magnetic sensor 25, the control unit 58 ceases to supply the electric current for the SMA coil 54b so that the SMA coil 54b returns back to a regular shape to withdraw the hollow needle 53 into the capsule-shaped casing 50. The control unit 58 stops driving the suction pump 57. The functions of the control unit 58 other than the function to control the driving unit 26 described above are identical with those of the control unit 28 of the capsule medical device 2 according to the first embodiment.

In the body-tissue obtaining system according to the second modification, the capsule medical device 52 configured as above is introduced into the subject 1, moves through the digestive organs of the subject 1 due to the peristalsis and the like, and reaches the in-vivo region to be examined. Similarly to the first embodiment described above, the user controls the magnetic-field generating unit 5 and the moving unit 7 via the input unit 8 while referring to the in-vivo image and the current position information displayed on the display unit 4.

The capsule medical device 52 inside the subject 1 extends the hollow needle 53 out of the capsule-shaped casing 50 at the timing when the rotating magnetic field and the gradient magnetic field are applied by the magnetic-field generating unit 5. The capsule medical device 52 rotates the hollow needle 53 along the circumferential direction of the capsule-shaped casing 50 by the function of the rotating magnetic field and the gradient magnetic field to cut out and obtain the mass of body tissue from the in-vivo region of the subject 1. The mass of body tissue is stored in the storage unit 55 of the capsule medical device 52. When the capsule medical device 52 having obtained the mass of body tissue is no longer affected by the rotating magnetic field and the gradient magnetic field, the capsule medical device 52 moves through the digestive organs due to the peristalsis and the like until naturally excreted outside the subject 1 at last. The mass of body tissue stored in the storage unit 55 of the capsule medical device 52 is retrieved by the doctor, the nurse, or the like, and used for the biopsy such as the pathological diagnosis.

Figure 17:
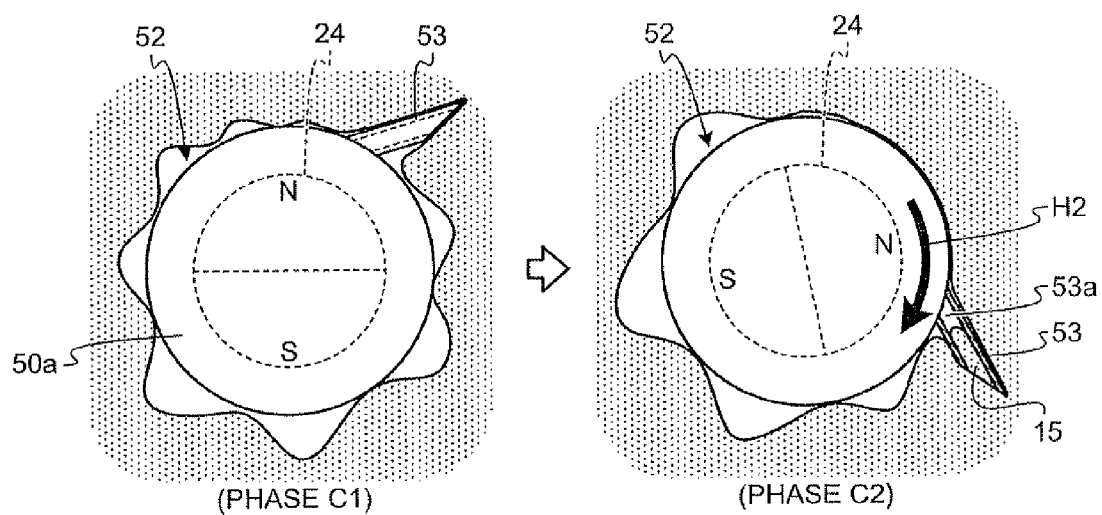
FIG. 17 is a schematic diagram illustrating phases where a hollow needle of the capsule medical device according to the second modification of the first embodiment cuts out and obtains a mass of the body tissue from a portion of the in-vivo region.

The operation of the capsule medical device 52 for cutting out and obtaining the mass of body tissue from the in-vivo region of the subject 1 is described. FIG. 17 is a schematic diagram illustrating phases where the mass of body tissue is cut out and obtained from a portion of the in-vivo region by the hollow needle 53 of the capsule medical device 52 according to the second modification of the first embodiment.

When the capsule medical device 52 inside the subject 1 reaches the in-vivo region to be examined, the magnetic-field generating unit 5 described above applies the rotating magnetic field to the capsule medical device 52. In the capsule medical device 52, the magnetic sensor 25 detects the rotating magnetic field generated by the magnetic-field generating unit 5. At the timing when the rotating magnetic field is detected by the magnetic sensor 25, the control unit 58 controls the extending-withdrawing system to extend the hollow needle 53 to puncture the in-vivo region (phase C1).

The capsule medical device 52 rotates along the circumferential direction of the capsule-shaped casing 50 due to the function of the magnet 24 influenced by the rotating magnetic field H2 (see FIG. 15). The hollow needle 53 maintains inertia to remain rotating along the circumferential direction of the capsule-shaped casing 50, and converts the torque generated by the magnet 24 described above into the cutting force to thereby strengthen the cutting force. The hollow needle 53 cuts out the mass of body tissue 15 from the in-vivo region, and takes the mass of body tissue 15 into the communicating hole 53a (phase C2). The mass of body tissue 15 in the hollow needle 53 is sucked out by the sucking force of the suction pump 57 described above into the storage unit 55. Thus, the cutting out and the obtaining of the mass of body tissue is completed. The storage unit 55 stores the mass of body tissue and prevents the mass of body tissue from dropping out.

When the capsule medical device 52 having the mass of body tissue 15 stored in the storage unit 55 is no longer influenced by the rotating magnetic field, the capsule medical device 52 withdraws the hollow needle 53 into the capsule-shaped casing 50, and stops driving of the suction pump 57. The capsule medical device 52 is naturally excreted outside the subject 1 due to the peristalsis and the like. After the capsule medical device 52 is naturally excreted outside the subject 1, the mass of body tissue in the storage unit 55 is taken by the doctor, the nurse, or the like, and used for the biopsy such as the pathological diagnosis.

When the capsule medical device 52 cuts out and obtains the mass of body tissue from the in-vivo region of the subject 1 by the hollow needle 53, the capsule medical device 52 rotates the hollow needle 53 along the circumferential direction of the capsule-shaped casing 50 due to the external rotating magnetic field. The tilted surface 53b of the tip end of the hollow needle 53 faces in the rotational direction (i.e., circumferential direction) of the capsule-shaped casing 50. The capsule medical device 52 can maintain the rotation inertia of the hollow needle 53 to remain rotating along the circumferential direction of the capsule-shaped casing 50, and can convert the torque along the circumferential direction generated by the magnet 24 influenced by the external rotating magnetic field into the cutting force of the hollow needle 53. Thus, the cutting force of the hollow needle 53 can be properly strengthened even in a small space such as the small intestine, the large intestine, and the like. The cutting force of the hollow needle 53 strengthened as above is much stronger than that of the forceps and the like of the conventional capsule medical device where the straight-line stroke of the forceps to be extended or withdrawn from the capsule-shaped casing is limited in a small space due to the size of the capsule-shaped casing. The cutting force of the hollow needle 53 is strong enough to securely cut out and obtain the mass of body tissue (the mass of body tissue 15) from the in-vivo region of the subject 1.

The mass of body tissue 15 which is cut out and obtained by the capsule medical device 52 is large enough to be used for the biopsy. The biopsy such as the pathological diagnosis using the mass of body tissue 15 can enhance accuracy of the biopsy and provide abundant medical information which is hard to obtain with a small amount of the body tissue such as a cross-sectional view of the body tissue in the in-vivo region to be examined.

The capsule medical device 52 described above has the capsule-shaped casing 50 rotated along the circumferential direction less than one revolution, and the hollow needle 53 rotates along the circumferential direction with the capsule-shaped casing 50 rotating less than one revolution in order to obtain the cutting force of the cutting unit 20c to securely cut out and obtain the mass of body tissue 15 from the in-vivo region. Further, the number of revolutions of the hollow needle 53 may be increased to further strengthen the cutting force of the hollow needle 53. Specifically, in the capsule medical device 52, the capsule-shaped casing 50 keeps rotating up to one or more revolutions along the circumferential direction of the capsule-shaped casing 50 due to the external rotating magnetic-field, and the number of revolutions of the hollow needle 53 rotating along the circumferential direction of the capsule-shaped casing 50 is increased to one or more. Thus, an amount of movement of the hollow needle 53 cutting out and obtaining the mass of body tissue can be increased up to infinity (equal to or longer than a length of the circumference along the circumferential direction of the capsule-shaped casing 50) along the circumferential direction of the capsule-shaped casing 50. As a result, the capsule medical device 52 can further strengthen the cutting force of the hollow needle 53 compared with the case where the number of revolutions of the capsule-shaped casing 50 is less than one, whereby the mass of body tissue 15 can be even more securely cut out and obtained from the in-vivo region.

As described above, in the second modification of the first embodiment of the present invention, the hollow needle is extended and withdrawn from the capsule-shaped casing in such a manner that the longitudinal direction of the extended hollow needle makes an acute angle with respect to the circumferential direction of the capsule-shaped casing, and that the cutting surface (the tilted surface of the tip end) of the extended hollow needle faces in the circumferential direction of the capsule-shaped casing. Then the extended hollow needle rotates with the capsule-shaped casing along the circumferential direction of the capsule-shaped casing due to the torque along the circumferential direction generated by the rotation driving unit. The hollow needle rotating along the circumferential direction cuts out and obtains the mass of body tissue from the in-vivo region of the subject. Other configurations are substantially identical with those of the first embodiment. Similarly to the first embodiment described above in a substantial way, the rotation inertia of the extended hollow needle is maintained, and the torque along the circumferential direction can be converted into the cutting force of the hollow needle. Thus, the cutting force of the hollow needle can be properly strengthened even in a small space such as the small intestine and the large intestine. As a result, the capsule medical device and the body-tissue obtaining method which can provide as much advantage as those of the first embodiment can be realized.

The inside of the hollow needle and the storage unit are communicated with each other via the tube. The mass of body tissue is sucked out into the hollow needle as the suction pump applies negative pressure to the storage unit. The mass of body tissue which is cut out and obtained by the hollow needle can be easily stored in the storage unit as the mass of body tissue is prevented from dropping out.

A second embodiment of the present invention is described. In the first embodiment and the first modification described above, the cutting unit is fixated on the cutting unit, and the cutting unit is rotated along the circumferential direction together with the capsule-shaped casing to cut out and obtain the mass of body tissue from the in-vivo region. In the second embodiment, however, the cutting unit is rotated along the circumferential direction inside the capsule-shaped casing, and the cutting unit inside the casing further cuts out and obtains the mass of body tissue from a portion of in-vivo region sucked into the capsule-shaped casing from the in-vivo region.

Figure 18:
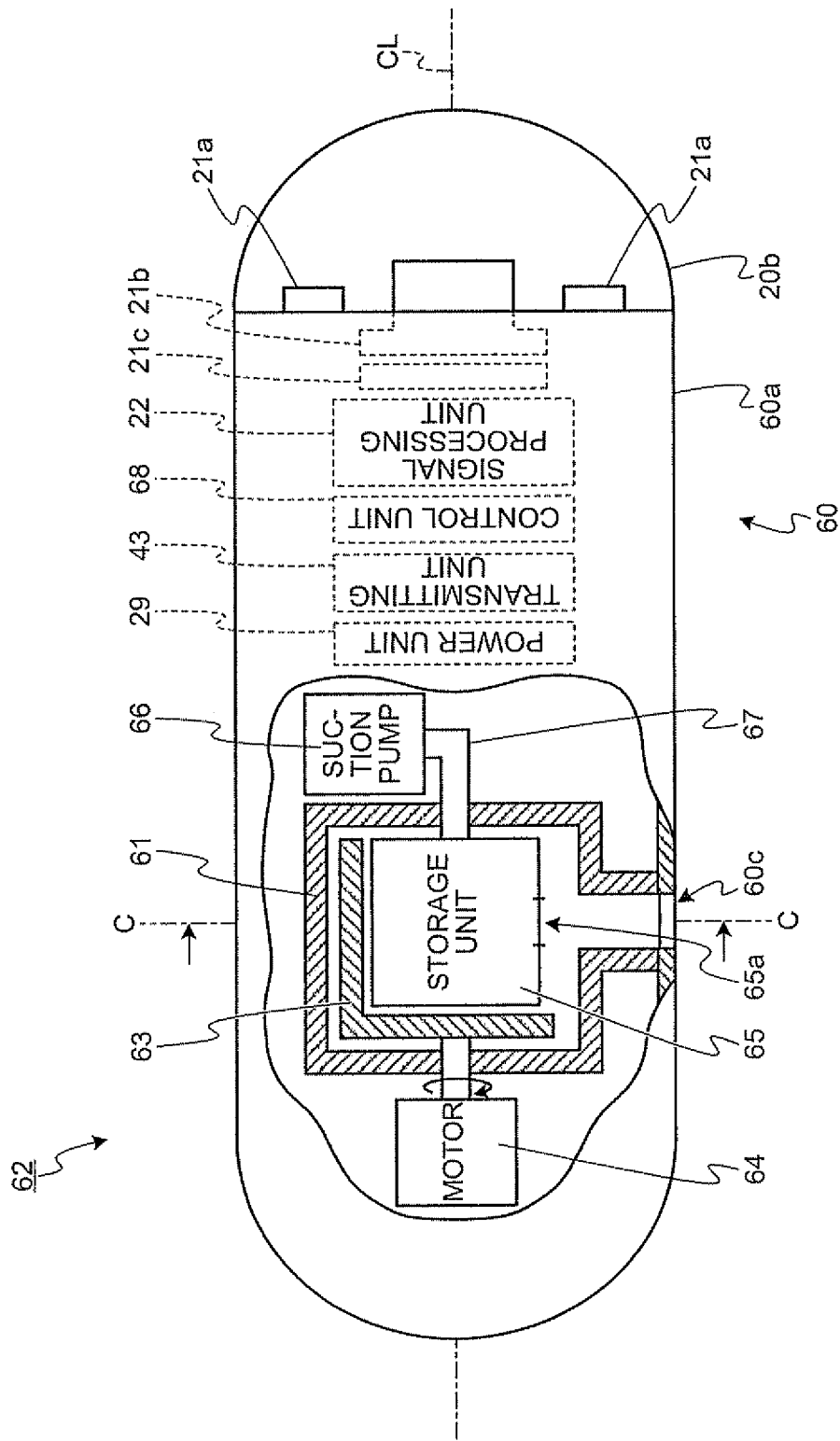
FIG. 18 is an example configuration of a capsule medical device according to a second embodiment of the present invention.
Figure 19:
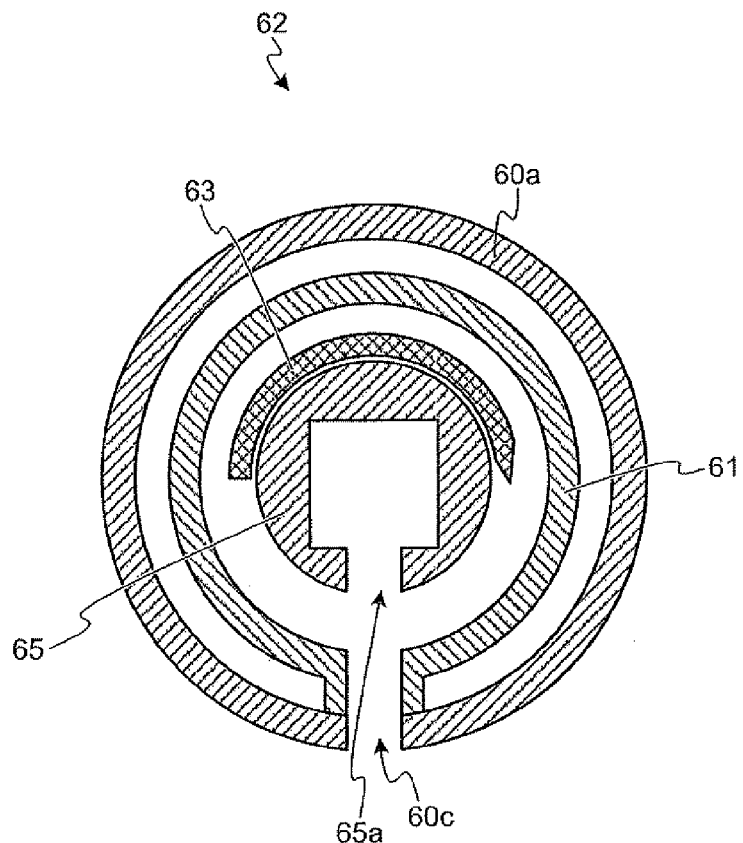
FIG. 19 is a schematic cross-sectional view taken along C-C line of the capsule medical device shown in FIG. 18.

FIG. 18 is a schematic diagram of an example configuration of a capsule medical device according to the second embodiment. FIG. 19 is a schematic cross-sectional view taken along line C-C of the capsule medical device shown in FIG. 18. FIG. 18 shows the capsule medical device according to the second embodiment a portion of which is broken so that the inner configuration of the capsule medical device according to the second embodiment can be described easily.

As shown in FIGS. 18 and 19, a capsule medical device 62 according to the second embodiment includes a capsule-shaped casing 60 instead of the capsule-shaped casing 40 of the capsule medical device 32 according to the first modification of the first embodiment described above, a cutting unit 63 instead of the cutting unit 20c, a motor 64 which rotates the cutting unit 63 instead of the motor 44 which rotates the exterior 40c, a storage unit 65 instead of the storage unit 47, and a control unit 68 instead of the control unit 48. The capsule medical device 62 does not include the driving unit 26, the exterior 40c, the fixation unit 41, and the motor 45 described above. Further, the capsule medical device 62 includes a separator 61 which separates the storage unit 65 from the electrical components and the like, and a suction pump 66 which is communicated with the storage unit 65 via a communicating pipe 67. The body-tissue obtaining system according to the second embodiment includes a capsule medical device 62 instead of the capsule medical device 32 of the body-tissue obtaining system 31 (see FIG. 9) according to the first modification of the first embodiment described above. Other configurations are identical with those of the first modification of the first embodiment, and same numerals denote the identical components.

The capsule-shaped casing 60 is of size which can be swallowed inside the subject 1. The capsule-shaped casing 60 includes a cylindrical casing 60a instead of the cylindrical casing 40a of the capsule medical device 32 according to the first modification of the first embodiment described above. In the capsule-shaped casing 60 is formed as one end (open end) of the cylindrical casing 60a whose another end is dome-shaped is sealed by the dome-shaped casing 20b. The cylindrical casing 60a is substantially opaque. An opening 60c through which the mass of body tissue is taken (sucked) is formed on a portion of the cylindrical casing 60a. In the capsule-shaped casing 60 formed by the cylindrical casing 60a and the dome-shaped casing 20b, the dome-shaped casing 20b includes the illuminating unit 21a, the optical system 21b, and the imaging unit 21c while the cylindrical casing 60a includes the signal processing unit 22, the transmitting and receiving unit 43, the separator 61, the cutting unit 63, the motor 64, the suction pump 66 which is communicated with the storage unit 65 via the communicating pipe 67, the control unit 68, and the power unit 29.

The separator 61 has a structure for separating the storage unit 65 from the built-in components of the capsule medical device 62 (specifically, the electrical components such as the imaging unit 21c and the control unit 68, the power unit 29, and the like). The separator 61 has a box-shaped structure which is communicated with an outside of the casing via the opening 60c of the capsule-shaped casing 60, and contains the cutting unit 63 and the storage unit 65. A through-hole through which a rotation shaft of the motor 64 passes and a through-hole through which the communicating pipe 67 passes are formed on a wall of the separator 61.

The cutting unit 63 works as a cutting-obtaining function, and cuts out the mass of body tissue from the in-vivo region of the subject 1. Specifically, the cutting unit 63 is a blade which is curved along a periphery of the storage unit 65, and the cutting unit 63 is arranged in the separator 61, more specifically, near the periphery surface of the storage unit 65 with the edge of the cutting unit facing in the circumferential direction of the capsule-shaped casing. The cutting unit 63 is fixated on the rotation shaft of the motor 64 which passes through the through-hole of the separator 61. The cutting unit 63 rotates along the circumferential direction of the capsule-shaped casing 60 by the driving force (torque along the circumferential direction) of the motor 64 to cut out and obtain the mass of body tissue from a portion of the in-vivo region sucked into the capsule-shaped casing 60. The mass of body tissue which is cut out and obtained by the cutting unit 63 is sucked into the storage unit 65 by the sucking force of the suction pump 66.

The motor 64 works as a rotation driving unit which generates the torque along the circumferential direction of the capsule-shaped casing 60. Specifically, the motor 64 includes a rotation shaft which is set parallel to the central shaft CL along the longitudinal direction of the capsule-shaped casing 60, and is connected with the cutting unit 63 in the separator 61 via the rotation shaft. As shown in FIG. 18, the rotation shaft of the motor 64 passes through the through-hole of the separator 61. As shown in FIG. 18, the motor 64 is driven under the control by the control unit 68, and rotates the cutting unit 63 along the circumferential direction of the capsule-shaped casing 60. The torque along the circumferential direction generated by the motor 64 is converted into the cutting force via the cutting unit 63.

The storage unit 65 stores the mass of body tissue which is cut out and obtained by the cutting unit 63 described above. As shown in FIGS. 18 and 19, the storage unit 65 is arranged in the capsule-shaped casing 60, and contained in the separator 61. The storage unit 65 is communicated with the suction pump 66 via the communicating pipe 67 which passes through the through-hole of the separator 61, and communicated with the separator 61 via the opening 65*a* formed at a position opposing to the opening 60*c* of the capsule-shaped casing 60. The storage unit 65 takes therein the mass of body tissue which is cut out and obtained by the cutting unit 63 by the sucking force of the suction pump 66, and stores the taken mass of body tissue.

The suction pump 66 is communicated with the storage unit 65 via the communicating pipe 67 which passes through the through-hole of the separator 61. The suction pump 66 applies negative pressure to the inside of the storage unit 65 which is communicated with the suction pump 66 via the communicating pipe 67, and applies negative pressure to the inside of the separator 61 via the storage unit 65. The suction pump 66 sucks out a portion of the in-vivo region via the opening 60*c* of the capsule-shaped casing 60, whereby the portion of in-vivo region is taken into the separator 61. The suction pump 66 fixates the capsule-shaped casing 60 on the in-vivo region. Further, the suction pump 66 sucks the mass of body tissue which is cut out and obtained by the cutting unit 63 from the portion of in-vivo region taken contained in the separator 61 into the storage unit 65.

The control unit 68 controls the driving of the motor 64 and the driving of the suction pump 66 based on the control signal from the above-described control unit 30 arranged outside. Under the control by the control unit 68, the motor 64 rotates the cutting unit 63 along the circumferential direction of the capsule-shaped casing 60, and the suction pump 66 sucks out the portion of in-vivo region into the separator 61*r* and the mass of body tissue which is cut out and obtained by the cutting unit 63 into the storage unit 65. The control unit 68 controls the driving of the motor 64 and the driving of the suction pump 66 a predetermined time period after the control unit 68 acquires the control signal from the transmitting and receiving unit 43. Under the control by the control unit 68, the motor 64 stops being driven to stop rotating the cutting unit 63, and the suction pump 66 stop sucking out the mass of body tissue. The functions of the control unit 68 other than the driving of the fixation unit 41, the driving unit 26, and the motors 44, 45 described above are identical with those of the control unit 48 of the capsule medical device 32 according to the first modification of the first embodiment.

In the body-tissue obtaining system according to the second embodiment, the capsule medical device 62 configured as above is introduced into the subject 1, moves through the digestive organs of the subject 1 due to the peristalsis and the like, and reaches the in-vivo region to be examined. The user controls the input unit 8 to instruct the capsule medical device 62 inside the subject 1 to cut out and obtain the mass of body tissue while referring to the in-vivo image and the current position information displayed on the display unit 4.

The capsule medical device 62 inside the subject 1 operates based on the control signal from the above-described control unit 30 arranged outside, and cuts out and obtains the mass of body tissue from the in-vivo region of the subject 1. The mass of body tissue is stored in the storage unit 65 of the capsule medical device 62. The capsule medical device 62 inside the subject 1 moves through the digestive organs due to the peristalsis and the like until naturally excreted outside the subject 1 at last. The mass of body tissue stored in the storage unit 65 of the capsule medical device 62 is taken by the doctor, the nurse, or the like, and used for the biopsy such as the pathological diagnosis.

Figure 20:
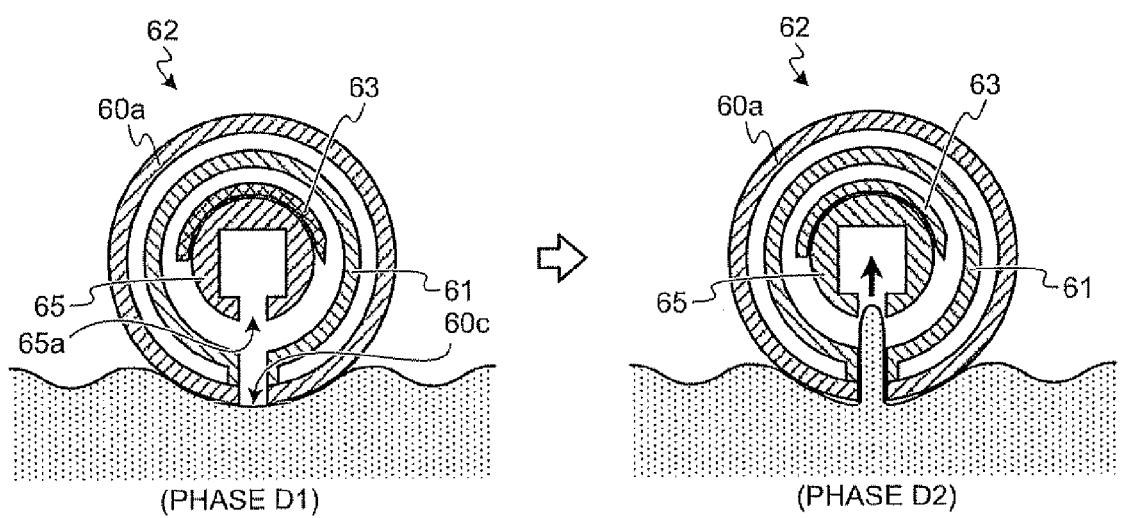
FIG. 20 is a schematic diagram illustrating phases where a portion of the in-vivo region is sucked out into a casing of the capsule medical device according to the second embodiment.
Figure 21:
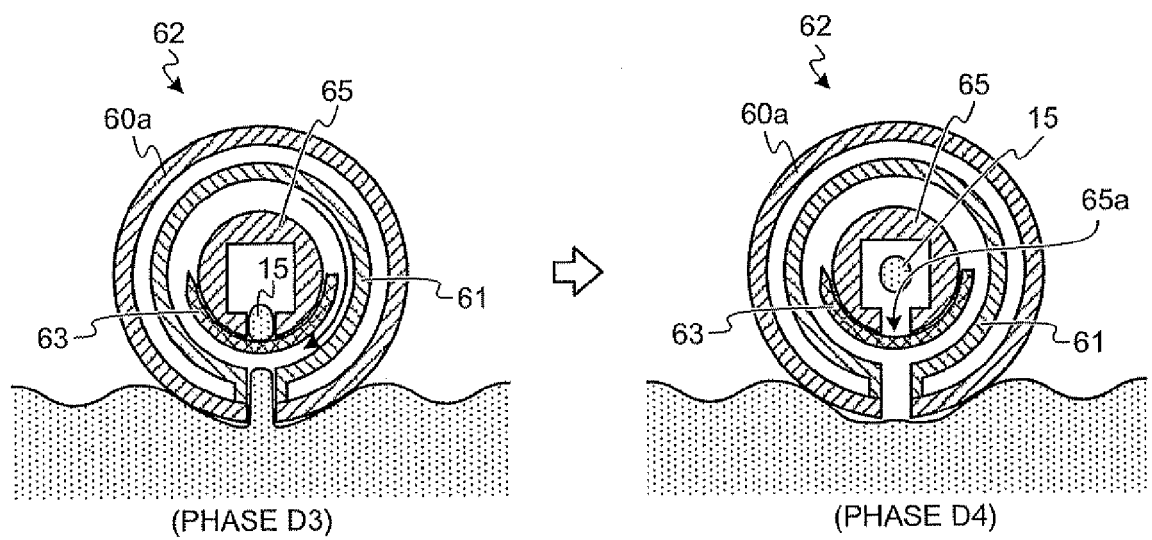
FIG. 21 is a schematic diagram illustrating phases where the cutting unit of the capsule medical device according to the second embodiment cuts out and obtains a mass of the body tissue.

The operation of the capsule medical device 62 for cutting out and obtaining the mass of body tissue from the in-vivo region of the subject 1 is described. FIG. 20 is a schematic diagram illustrating phases where a portion of the in-vivo region is sucked into the casing of the capsule medical device 62 according to the second embodiment. FIG. 21 is a schematic diagram illustrating phases where the mass of body tissue is cut out and obtained from the in-vivo region by the cutting unit 63 of the capsule medical device 62 according to the second embodiment.

When the capsule medical device 62 reaches the in-vivo region to be examined, the capsule medical device 62 inside the subject 1 acquires the control signal from the control unit 30 arranged outside, and performs a series of operations for cutting out and obtaining the mass of body tissue from the in-vivo region based on the acquired control signal. Specifically, as shown in FIG. 20, in the capsule medical device 62, the opening 60*c* of the cylindrical casing 60*a* faces the wall surface of the in-vivo region to be examined (phase D1), the cutting unit 63 rotates along the circumferential direction of the capsule-shaped casing 60 due to the torque along the circumferential direction generated by the motor 64 described above, and the suction pump 66 applies negative pressure to the inside of the storage unit and the separator 61. The capsule medical device 62 sucks out a portion of the in-vivo region into the separator 61 by the sucking force of the suction pump 66 (phase D2). At the phase D2, the capsule medical device 62 is fixated on the in-vivo region by the sucking force of the suction pump 66.

The capsule medical device 62 rotates the cutting unit 63 along the circumferential direction of the capsule-shaped casing (the direction along the arrow shown in FIG. 21) by the torque along the circumferential direction generated by the motor 64 with the portion of in-vivo region sucked into (taken) the separator 61 (i.e., into the capsule-shaped casing 60). The cutting unit 63 maintains the inertia to remain rotating along the circumferential direction of the capsule-shaped casing 60, and converts the torque along the circumferential direction generated by the motor 64 into the cutting force.

Thus the cutting unit 63 strengthens the cutting force, and cuts out and obtains the mass of body tissue 15 from the portion of in-vivo region captured inside the separator 61 described as above, as shown in FIG. 21 (phase D3).

The mass of body tissue 15 which is cut out and obtained by the cutting unit 63 is taken into the storage unit 65 due to the sucking force of the suction pump 66 described above. The storage unit 65 stores therein the mass of body tissue 15. The control unit 68 of the capsule medical device 62 stops the driving of the suction pump 66 described above, and the driving of the motor 64 at the timing when the cutting unit 63 is arranged in the opening 65*a* of the storage unit 65. Under the control by the control unit 68, the cutting unit 63 seals up the opening 65*a* of the storage unit 65, and the closed storage unit 65 stores the mass of body tissue 15, and prevents the same from dropping out (phase D4).

After the capsule medical device 62 having the mass of body tissue 15 stored in the storage unit 65 ceases to be fixated on the in-vivo region, the capsule medical device 62 moves through the digestive organs due to the peristalsis and the like until naturally excreted outside the subject 1 at last. After the capsule medical device is naturally excreted outside the subject 1, the mass of body tissue 15 inside the storage unit 65 is taken by the doctor, the nurse, or the like, and used for the biopsy such as the pathological diagnosis.

When the capsule medical device 62 cuts out and obtains the mass of body tissue from the in-vivo region of the subject 1 by the cutting unit 63, the capsule-shaped casing 60 is fixated on the in-vivo region as the portion of in-vivo region is sucked into the capsule-shaped casing 60 due to the sucking force of the suction pump 66, and the cutting unit 63 rotates along the circumferential direction of the capsule-shaped casing 60 due to the torque along the circumferential direction generated by the motor 64. Thus, the capsule medical device 62 can maintain the rotation inertia of the cutting unit 63 to remain rotating along the circumferential direction of the capsule-shaped casing 60*r* and can convert the torque along the circumferential direction generated by the motor 64 into the cutting force of the cutting unit 63, and the portion of in-vivo region can be fixated in a track of the rotating cutting unit 63. Thus, the cutting force of the cutting unit 63 can be properly strengthened even in a small space such as the small intestine and the large intestine. The cutting force of the cutting unit 63 strengthened as above is much stronger than that of the forceps and the like of the conventional capsule medical device where the straight-line stroke of the forceps to be extended and withdrawn is limited in a small space due to the size of the capsule-shaped casing. The cutting force is made strong enough to securely cut out and obtain the mass of body tissue (the mass of body tissue 15) from the in-vivo region of the subject 1.

The mass of body tissue 15 which is cut out and obtained by the capsule medical device 62 is large enough as a sample for the biopsy, similarly to the first modification of the first embodiment. The biopsy such as the pathological diagnosis using the mass of body tissue 15 can enhance accuracy of the biopsy, and provide abundant medical information which is hard to obtain with a small amount of the body tissue such as a cross-sectional view of the body tissue in the in-vivo region to be examined.

The capsule medical device 62 described above has the cutting unit 63 rotated along the circumferential direction less than one revolution before the cutting unit 63 finishes cutting out and obtaining the mass of body tissue 15, and the cutting unit 63 rotating less than one revolution obtains the cutting force to securely cut out and obtain the mass of body tissue 15 from the in-vivo region. Further, the number of revolutions of the cutting unit 63 may be increased to further strengthen the cutting force of the cutting unit 63. Specifically, the capsule medical device 62 can start driving the motor 64 before the cutting and obtaining of the mass of body tissue, and keeps driving the motor 64 to increase the number of revolutions of the cutting unit 63 rotating along the circumferential direction to one or more. Thus, an amount of movement of the cutting unit 63 cutting out and obtaining the mass of body tissue can be increased up to infinity (equal to or longer than a length of the circumference along the circumferential direction of the capsule-shaped casing 60) along the circumferential direction of the capsule-shaped casing 60. As a result, the capsule medical device 62 can further strengthen the cutting force of the cutting unit 63 compared with the case where the number of revolutions is less than one, whereby the mass of body tissue 15 can be even more securely cut out and obtained from the in-vivo region.

As described above, in the second embodiment of the present invention, the cutting unit is rotatably arranged in the capsule-shaped casing with the edge of the cutting unit facing in the circumferential direction of the capsule-shaped casing, and the suction pump which sucks the portion of in-vivo region to keep the in-vivo region in the trace of the rotating cutting unit is arranged. The cutting unit rotates along the circumferential direction of the capsule-shaped casing due to the torque along the circumferential direction generated by the rotation driving unit, and the cutting unit rotating along the circumferential direction cuts out and obtains the mass of body tissue from the sucked portion of in-vivo region. Other configurations are substantially identical with those of the first modification of the first embodiment. Similarly to the first modification of the first embodiment described above, the rotation inertia of the cutting unit can be maintained, and the torque along the circumferential direction can be converted into the cutting force. The capsule-shaped casing can be fixated on the in-vivo region due to the sucking force of the suction pump, and the mass of body tissue which is large enough can be taken into the capsule-shaped casing from the in-vivo region. As a result, the capsule medical device and the body-tissue obtaining method which can provide as much advantage as those of the first modification of the first embodiment described above, and which can easily cutout and obtain the larger amount of the mass of body tissue can be realized.

The cutting unit inside the capsule-shaped casing cuts out and obtains the mass of body tissue from the portion of in-vivo region sucked into the capsule-shaped casing, and the cutting unit is not exposed to the outside of the capsule-shaped casing, whereby the mass of body tissue can be more securely cut out and obtained from the in-vivo region of the subject.

A third embodiment of the present invention is described. In the second embodiment described above, the portion of in-vivo region is taken into the capsule-shaped casing due to the sucking force of the suction pump 66. In the third embodiment, however, the portion of in-vivo region is taken into the capsule-shaped casing by a hook rotating along the circumferential direction of the capsule-shaped casing 60.

Figure 22:
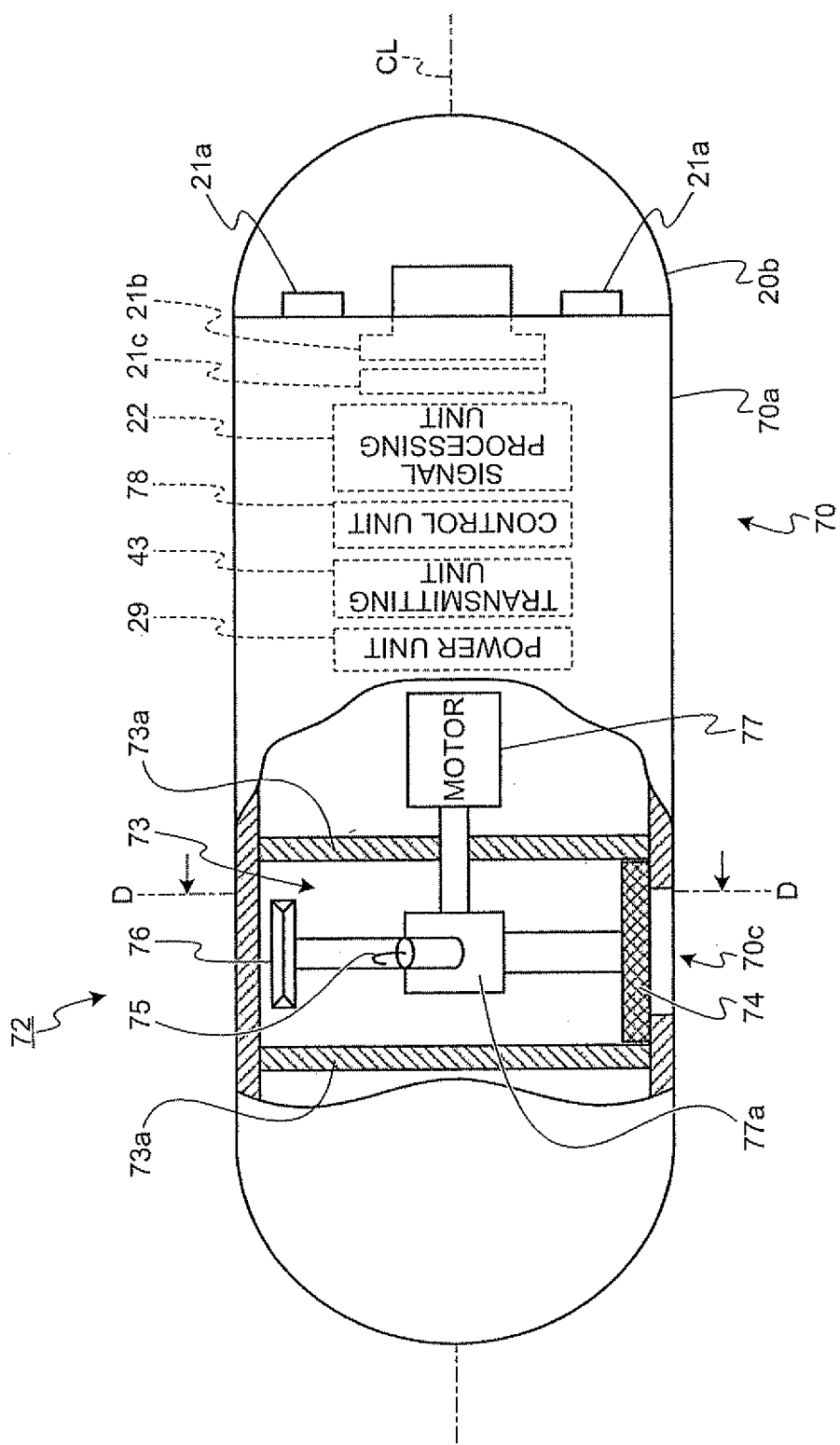
FIG. 22 is a schematic diagram of an example configuration of a capsule medical device according to a third embodiment of the present invention.
Figure 23:
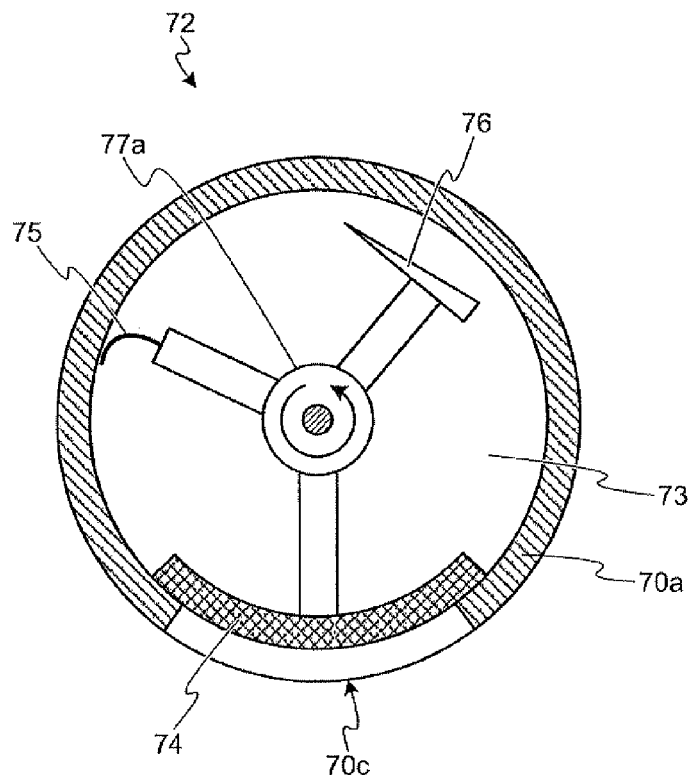
FIG. 23 is a schematic cross-sectional view taken along D-D line of the capsule medical device shown in FIG. 22.

FIG. 22 is a schematic diagram of an example configuration of a capsule medical device according to the third embodiment of the present invention. FIG. 23 is a schematic cross-sectional view taken along line D-D of the capsule medical device shown in FIG. 22. FIG. 22 also shows the capsule medical device according to the third embodiment so that the inner configuration of the capsule medical device can be easily described.

As shown in FIGS. 22 and 23, the capsule medical device 72 according to the third embodiment includes a capsule-shaped casing 70 instead of the capsule-shaped casing 60 of the capsule medical device 62 according to the second embodiment described above, a storage unit 63 instead of the storage unit 65, a motor 77 instead of the motor 64, and a control unit 78 instead of the control unit 68. Further, the capsule medical device 72 includes a hook 75 which takes the portion of in-vivo region into the capsule-shaped casing 70 instead of the suction pump 66 of the capsule medical device 62 according to the second embodiment described above, and a cutting unit 76 which cuts out and obtains the mass of body tissue from the portion of in-vivo region captured by the hook 75 instead of the cutting unit 63. The hook 75 and the cutting unit 76 are supported by a rotation supporting unit 77a which is connected with a rotation shaft of the motor 77. The rotation supporting unit 77a further supports the lid part 74. A body-tissue obtaining system according to the third embodiment includes the capsule medical device 72 instead of the capsule medical device 62 of the body-tissue obtaining system according to the second embodiment described above. Other configurations are identical with those of the second embodiment, and same numerals denote the identical components.

The capsule-shaped casing 70 is of a size which can be introduced into the subject 1. The capsule-shaped casing 70 includes a cylindrical casing 70a instead of the cylindrical casing 60a of the capsule medical device 62 according to the second embodiment described above. The capsule-shaped casing 70 is formed as one end (open end) of the cylindrical casing 70a whose another end is dome-shaped is sealed by the dome-shaped casing 20b. The cylindrical casing 70a is substantially opaque. An opening 70c through which the mass of body tissue is taken (taken) is formed on a portion of the cylindrical casing 70a. In the capsule-shaped casing 70 formed by the cylindrical casing 70a and the dome-shaped casing 20b, the dome-shaped casing 20b includes the illuminating unit 21a, the optical system 21, and the imaging unit 21c while the cylindrical casing 70a includes the signal processing unit 22, the transmitting and receiving unit 43, the storage unit 73, the lid part 74, the hook 75, the cutting unit 76, the motor 77, the rotation supporting unit 77a, the control unit 78, and the power unit 29.

The storage unit 73 stores the mass of body tissue which is cut out and obtained by the cutting unit 76. As shown in FIGS. 22 and 23, the storage unit 73 is formed by a portion of the cylindrical casing 70a and a wall part 73a. The inner space of the storage unit 73 is separated by the wall part 73a from the built-in components of the capsule medical device 72 (specifically, the electrical components such as the imaging unit 21c and the control unit 78, the power unit 29, and the like). The wall part 73a of the storage unit 73 has a through-hole through which a rotation shaft of the motor 77 passes. The storage unit 77 is communicated with the outside via the opening 70c, and stores therein the mass of body tissue taken into the opening 70c.

The lid part 74 is supported by the rotation supporting unit 77a. The lid part 74 rotates along the circumferential direction of the capsule-shaped casing 70 due to the driving force of the motor 77 (torque along the circumferential direction) so as to open and close the opening 70c of the capsule-shaped casing 70. Specifically, as shown in FIGS. 22 and 23, the lid part 74 closes the opening 70c when the lid part 74 is arranged near the opening 70c, whereas the lid part 74 opens the opening 70c when the lid part 74 revolves away from the opening 70c.

The hook 75 takes (pulls) the portion of in-vivo region of the subject 1 into the capsule-shaped casing 7. Specifically, the hook 75 is supported by the rotation supporting unit 77a, and rotates along the circumferential direction of the capsule-shaped casing 70 due to the driving force of the motor 77, and pulls the portion of in-vivo region into the capsule-shaped casing 70 (specifically, into the storage unit 73) through the opening 70c of the capsule-shaped casing 70. The hook 75 is arranged behind the lid part 74 in a rotation direction (a direction along the arrow shown in FIG. 23). The cutting unit 76 cuts out and obtains the mass of body tissue from the in-vivo region captured into the capsule-shaped casing 70 by the hook 75. The mass of body tissue cut out and obtained by the cutting unit 76 is usually kept hooked to the hook 75 while stored in the storage unit 73.

The motor 77 works as a rotation driving unit which generates the torque along the circumferential direction of the capsule-shaped casing 70. Specifically, the motor 77 has a rotation shaft which is set parallel to the central shaft CL along the longitudinal direction of the capsule-shaped casing 70. The motor 77 is connected with the rotation supporting unit 77a in the storage unit 73 via the rotation shaft. As shown in FIG. 22, the rotation shaft of the motor 77 passes through the through-hole formed on the wall part 73a of the storage unit 73. The rotation supporting unit 77a supports the lid part 74, the hook 75, and the cutting unit 76 as described above, and rotates along the circumferential direction of the capsule-shaped casing 70 due to the driving force of the motor 77. The motor 77 rotates the lid part 74, the hook 75, and the cutting unit 76 together with the rotation supporting unit 77a along the circumferential direction of the capsule-shaped casing 70.

The control unit 78 controls the driving of the motor 77 to rotate the lid part 74, the hook 75, and the cutting unit 76 with the rotation supporting unit 77a along the circumferential direction of the capsule-shaped casing 70 (the direction along the arrow shown in FIG. 23) based on the above-described control signal from the control unit 30 arranged outside. Under the control by the control unit 78, the lid part 74 opens and closes the opening 70c of the capsule-shaped casing 70, the hook 75 pulls the portion of in-vivo region into the storage unit 73 through the opened opening 70c, and the cutting unit 76 cuts out and obtains the mass of in-vivo region from the portion of in-vivo region pulled into the storage unit 73 by the hook 75. A predetermined time period after the control unit 78 acquires the control signal from the transmitting and receiving unit 43, the control unit 78 stops driving the motor 77 to stop rotating the rotation supporting unit 77a, i.e., stop rotating the lid part 74, the hook 75, and the cutting unit 76. The control unit 78 stops driving the motor 77 by closing the opening 70c with the lid part 74. The functions of the control unit 78 are identical with those of the control unit 68 of the capsule medical device 62 according to the second embodiment except the control of the motor 64 and the suction pump 66 described above.

In the body-tissue obtaining system according to the third embodiment, the capsule medical device 72 configured as above is introduced into the subject 1, moves through the digestive organs of the subject 1 due to the peristalsis and the like, and reaches the in-vivo region to be examined. Similarly to the second embodiment described above, the user controls the input unit 8 to instruct the capsule medical device 72 inside the subject 1 to cut out and obtain the mass of body tissue while referring to the in-vivo image and the current position information displayed on the display unit 4.

The capsule medical device 72 inside the subject 1 operates based on the above-described control signal from the control unit 30 arranged outside, and cuts out and obtains the mass of body tissue from the in-vivo region of the subject 1. The mass of body tissue is stored in the storage unit 73 of the capsule medical device 72. The capsule medical device 72 inside the subject 1 moves through the digestive organs due the peristalsis and the like until naturally excreted outside the subject 1 at last. The mass of body tissue stored in the storage unit 73 of the capsule medical device 72 is retrieved by the doctor, the nurse, or the like, and used for the biopsy such as the pathological diagnosis.

Figure 24:
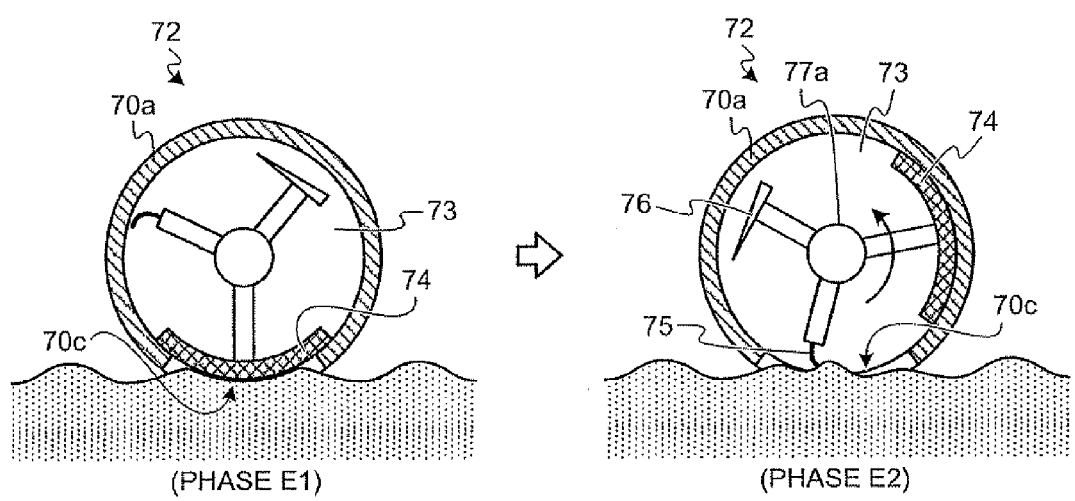
FIG. 24 is a schematic diagram illustrating phases where a hook of the capsule medical device is hooked to a portion of the in-vivo region.
Figure 25:
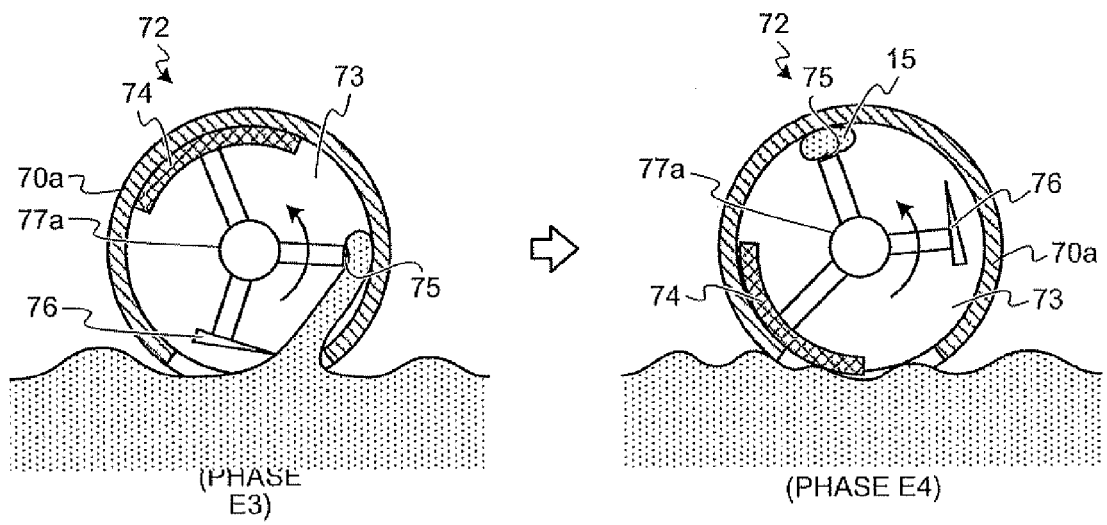
FIG. 25 is a schematic diagram illustrating phases where the cutting unit cuts out and obtains a mass of the body tissue from the portion of in-vivo region which is pulled into the storage unit by the hook.
Figure 26:
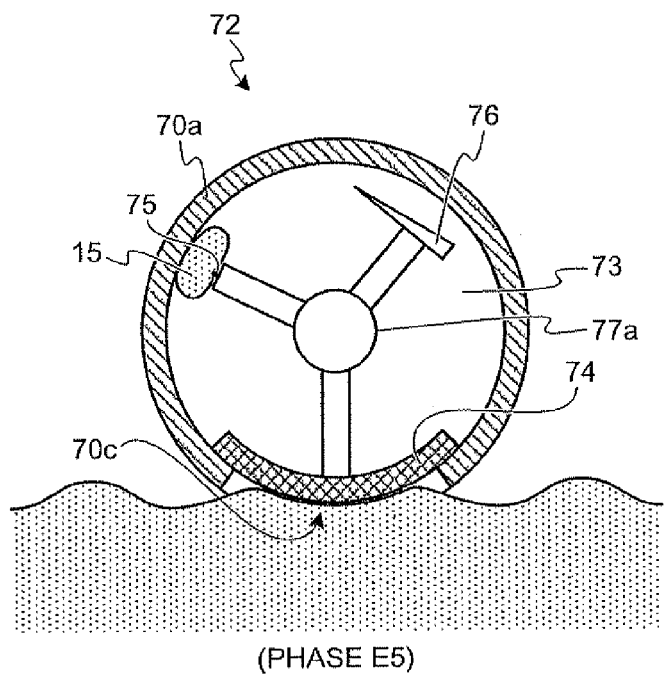
FIG. 26 is a schematic diagram illustrating a phase where the mass of body tissue hooked to the hook is stored in the storage unit.

The operation of the capsule medical device 72 for cutting out and obtaining the mass of body tissue from the in-vivo region of the subject 1 is described. FIG. 24 is a schematic diagram illustrating phases where the portion of in-vivo region is hooked by the hook 75 of the capsule medical device 72 according to the third embodiment. FIG. 25 is a schematic diagram illustrating phases where the mass of body tissue is cut out and obtained by the cutting unit 76 from the portion of in-vivo region pulled into the storage unit 73 by the hook 75. FIG. 26 is a schematic diagram illustrating phases where the mass of body tissue which is kept hooked to the hook 75 is stored in the storage unit 73.

The capsule medical device 72 inside the subject 1 acquires the control signal from the control unit 30 arranged outside when reaching the in-vivo region to be examined. Based on the acquired control signal, the capsule medical device 72 performs a series of operations for cutting out and obtaining the mass of body tissue. Specifically, as shown in FIG. 24, in the capsule medical device 72, the opening 70c of the cylindrical casing 70a faces the wall surface of the in-vivo region to be examined (phase E1), and the rotation supporting unit 77a is rotated with the lid part 74, the hook 75, and the cutting unit 76 along the circumferential direction of the capsule-shaped casing 70 by the torque along the circumferential direction generated by the motor 77 described above. The capsule medical device 72 opens the opening 70c of the cylindrical casing 70a, and has the hook 75 hooked to the in-vivo region near the opened opening 70c (phase E2).

The capsule medical device 72 keeps the hook 75 hooked to the portion of in-vivo region, and keeps rotating the lid part 74, the hook 75, and the cutting unit 76. As shown in FIG. 25, the hook 75 pulls the portion of in-vivo region into the storage unit 73, and the cutting unit 76 forces the blade into a base of the portion of in-vivo region (phase E3). At the state E3, the hook 75 pulls and fixates the portion of in-vivo region so that the portion of in-vivo region can be easily cut out by the cutting unit 76.

The capsule medical device 72 keeps rotating the lid part 74, the hook 75, and the cutting unit 76. The cutting unit 76 cuts out and obtains the mass of body tissue 15 from the portion of in-vivo region pulled into the storage unit 73 by the hook 75. As shown in FIG. 25, the mass of body tissue 15 is hooked to the hook 75 while being stored in the storage unit 73 (phase E4).

The capsule medical device 72 keeps rotating the lid part 74, the hook 75, and the cutting unit 76 until the lid part 74 moves to the position of the opening 70c. The lid part 74 closes the storage unit 73 by closing the opening 70c, and the closed storage unit 73 stores the mass of body tissue 15 hooked to the hook 75 (phase E5). As a result, the storage unit 73 can store the mass of body tissue 15 and prevents the same from dropping out.

The capsule medical device 72 having the mass of body tissue 15 stored in the storage unit 73 moves through the digestive organs due to the peristalsis and the like until naturally excreted outside the subject 1 at last. After the capsule medical device 72 is naturally excreted outside the subject 1, the mass of body tissue 15 in the storage unit 73 is retrieved by the doctor, the nurse, or the like, and used for the biopsy such as the pathological diagnosis.

In the capsule medical device 72, when the cutting unit 76 cuts out and obtains the mass of body tissue from the in-vivo region of the subject 1, the hook 75 pulls the portion of in-vivo region into the capsule-shaped casing 70, and rotates the cutting unit 76 along the circumferential direction of the capsule-shaped casing 70 by the torque along the circumferential direction generated by the motor 77. The capsule medical device 72 maintains the rotation inertia of the cutting unit 76 to remain rotating along the circumferential direction of the capsule-shaped casing 70, and converts the torque along the circumferential direction generated by the motor 77 into the cutting force of the cutting unit 76. The capsule medical device 72 keeps the portion of in-vivo region under tension by the hook 75 to fixated the portion of in-vivo region in the trace of the rotating cutting unit 76. Thus, the cutting force of the cutting unit 76 can be properly strengthened even in a small space such as the small intestine and the large intestine. The cutting force of the cutting unit 76 strengthened as above is much stronger than that of the forceps and the like of the conventional capsule medical device where the straight-line stroke of the forceps to be extended and withdrawn from the capsule-shaped casing is limited in a small space due to the size of the capsule-shaped casing. The cutting force is made strong enough to securely cut out and obtain the mass of body tissue (the mass of body tissue 15) from the in-vivo region of the subject 1.

The mass of body tissue 15 obtained by the capsule medical device 72 is large enough to be used as a sample for the biopsy, similarly to the second embodiment. The biopsy such as the pathological diagnosis using the mass of body tissue 15 can enhance accuracy of the biopsy and provide abundant medical information which is hard to obtain with a small amount of the body tissue such as a cross-sectional view of the body tissue of the in-vivo region to be examined.

The capsule medical device 72 described above has the cutting unit 76 rotated less than one revolution before the cutting unit 76 finishes cutting out and obtaining the mass of body tissue 15, and the cutting unit 76 rotating less than one revolution obtains the cutting force to securely cut out and obtain the mass of body tissue 15 from the in-vivo region. Further, the number of revolutions of the cutting unit 76 may be increased to further strengthen the cutting force of the cutting unit 76. Specifically, the capsule medical device 72 can start driving the motor 77 before the hook 75 pulls the portion of in-vivo region inside, and keeps driving the motor 77 to increase the number of revolutions of the cutting unit 76 along the circumferential direction to one or more. Thus, an amount of movement of the cutting unit 76 cutting out and obtaining the mass of body tissue can be increased up to infinity (equal to or longer than a length of the circumference along the circumferential direction of the capsule-shaped casing 70) along the circumferential direction of the capsule-shaped casing 70. As a result, the capsule medical device 72 can further strengthen the cutting force of the cutting unit 76 compared with the case where the number of revolutions is less than one, whereby the mass of body tissue 15 can be even more securely cut out and obtained from the in-vivo region.

As described above, in the third embodiment of the present invention, the cutting unit is rotatably arranged inside the capsule-shaped casing with the edge of the cutting unit facing in the circumferential direction of the capsule-shaped casing. The hook which rotates along the circumferential direction ahead of the cutting unit and pulls the portion of in-vivo region into the capsule-shaped casing is arranged. The hook and the cutting unit rotate along the circumferential direction of the capsule-shaped casing due to the torque along the circumferential direction generated by the rotation driving unit. The in-vivo region which is pulled into the capsule-shaped casing by the hook rotating along the circumferential direction is cut out and obtained by the cutting unit rotating along the circumferential direction. Other configurations of the third embodiment are approximately identical with those of the second embodiment. Similarly to the second embodiment in a substantial way, the rotation inertia of the cutting unit is maintained, and the torque along the circumferential direction is converted into the cutting force of the cutting unit. The portion of in-vivo region is stretched and fixated by the hook, and the mass of in-vivo region which is large enough is captured into the capsule-shaped casing from the in-vivo region. As a result, the capsule medical device and the body-tissue obtaining method which provide as much advantage as those of the second embodiment, and even more easily realize the cutting unit which cuts out and obtains the mass of body tissue can be realized.

A fourth embodiment of the present invention is described. In the first embodiment described above, the cutting unit 20c cuts out and obtains the mass of body tissue with the edge of the cutting unit facing in the circumferential direction of the capsule-shaped casing 20. In the fourth embodiment, however, the cutting unit is arranged with the edge of the cutting unit facing in the longitudinal direction of the capsule-shaped casing, and rotates along the circumferential direction of the capsule-shaped casing to cut out and obtain the mass of body tissue from the in-vivo region.

Figure 27:
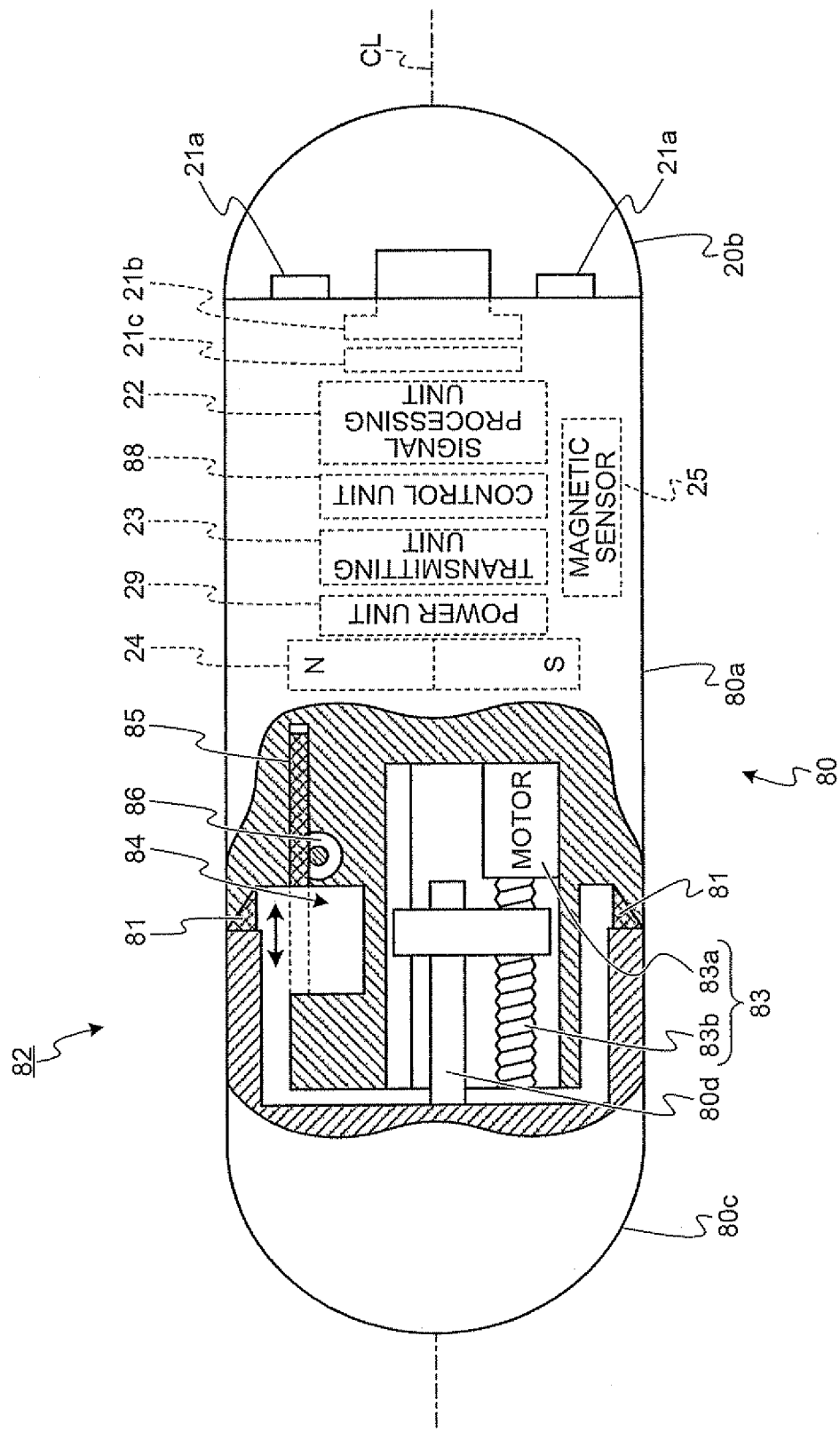
FIG. 27 is a schematic diagram showing an example configuration of a capsule medical device according to a fourth embodiment of the present invention.
Figure 28:
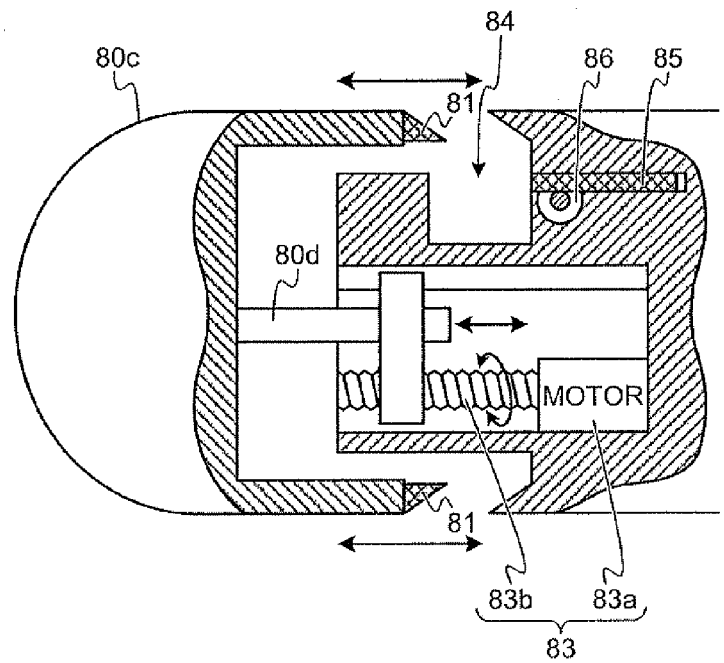
FIG. 28 is a schematic diagram illustrating a state where the cutting unit is exposed as the exterior of the capsule medical device shown in FIG. 27 slides.

FIG. 27 is a schematic diagram of an example configuration of a capsule medical device according to the fourth embodiment of the present invention. FIG. 28 is a schematic diagram showing a state where the cutting unit is exposed as the exterior of the capsule medical device shown in FIG. 27 slides. FIGS. 27 and 28 show the capsule medical device according to the fourth embodiment a part of which is broken so that the inner configuration of the capsule medical device according to the fourth embodiment can be easily described.

As shown in FIGS. 27 and 28, a capsule medical device 82 according to the fourth embodiment includes the capsule-shaped casing 80 instead of the capsule-shaped casing 20 of the capsule medical device 2 according to the first embodiment described above, a cutting unit 81 instead of the cutting unit 20c, an exterior 80c instead of the outer covering 20d, a linear-motion system 83 instead of the driving unit 26, a storage unit 84 instead of the storage unit 27, and a control unit 88 instead of the control unit 28. The capsule medical device 82 includes a lid part 85 which opens and closes the storage unit 84, and a motor 86 which drives the opening and the closing of the lid part 85. A body-tissue obtaining system according to the fourth embodiment includes the capsule medical device 82 instead of the capsule medical device 2 of the body-tissue obtaining system 11 (see FIG. 1) according to the first embodiment described above. Other configurations are identical with those of the first embodiment, and same numerals denote the identical components.

The capsule-shaped casing 80 is of a size which can be introduced into the subject 1. The capsule-shaped casing 80 includes a cylindrical casing 80a instead of the cylindrical casing 20a of the capsule medical device 2 according to the first embodiment described above. The capsule-shaped casing 80 is formed as one end (open end) of the cylindrical casing 80a having the exterior 80c arranged on another end is sealed by the dome-shaped casing 20b. The cylindrical casing 80a is substantially opaque. The storage unit 84 is formed on a portion of the cylindrical casing 80a. In the capsule-shaped casing 80 formed by the cylindrical casing 80a and the dome-shaped casing 20b, the dome-shaped casing 20b includes the illuminating unit 21a, the optical system 21b, and the imaging unit 21c while the cylindrical casing 80a includes the signal processing unit 22, the transmitting unit 23, the magnet 24, the magnetic sensor 25, the linear-motion system 83, the lid part 85, the motor 86, the control unit 88, and the power unit 29.

The exterior 80c has a bottomed structure where a dome-shaped part is formed on one end of a cylindrical part. The exterior 80c is arranged on the cylindrical casing 80a, and covers one end of the cylindrical casing 80a (an end on a side opposing to the dome-shaped casing 20b). The exterior 80c is supported by a rod-shaped supporting unit 80d which is connected with the linear-motion system 83 in a manner such that the exterior 80c can be moved linearly in a longitudinal direction of the capsule-shaped casing 80. The cutting unit 81 is fixated on the open end of the exterior 80c with the edge of the cutting unit facing in the longitudinal direction of the capsule-shaped casing 80. As shown in FIG. 28, when the exterior 80c driven by the linear-motion system 83 described later moves linearly away from the cylindrical casing 80a (in a longitudinal direction of capsule-shaped casing 80), an opening is formed on the capsule-shaped casing 80 and the cutting unit 81 is exposed to an outside. On the other hand, when the exterior 80c driven by the linear-motion system 83 moves close to the cylindrical casing 80a (a longitudinal direction of the capsule-shaped casing), the exterior 80c is engaged with the edge of the cylindrical casing 80a, whereby the opening of the capsule-shaped casing is closed and the cutting unit 81 is stored in the cylindrical casing 80a.

The cutting unit 81 works as the cutting and obtaining function, and cuts out and obtains the mass of body tissue from the in-vivo region of the subject 1. Specifically, the cutting unit 81 is a blade having an edge arranged in a circle, and the cutting unit 81 is fixated on the open end of the exterior 80c with the edge of the cutting unit facing in the longitudinal direction of the capsule-shaped casing 80. The cutting unit 81 rotates along the circumferential direction of the capsule-shaped casing with the exterior 80c due to the torque along the circumferential direction generated by the magnet 24 described above. As a result, the cutting unit 81 cuts out and obtains the mass of body tissue from the in-vivo region of the subject 1. The mass of body tissue which is cut out and obtained by the cutting unit 81 is stored in the storage unit 84.

The linear-motion system 83 moves the exterior 80c linearly in the longitudinal direction of the capsule-shaped casing 80 to move the exterior 80c away from the capsule-shaped casing 80 (specifically, the cylindrical casing 80a), or to connect the exterior 80c with the capsule-shaped casing 80. The linear-motion system 83 is realized by a motor 83a, and a ball screw 83b. The linear-motion system 83 is arranged in the back of the cylindrical casing 80a as shown in FIG. 27. The ball screw 83b is rotatably connected with the motor 83a, and set parallel to the central shaft CL of the capsule-shaped casing 80. Further, the rod-shaped supporting unit 80d which supports the exterior 80c described above is connected with the ball screw 83b. The motor 83a is driven by the control unit 88 to rotate the ball screw 83b so that the exterior 80c moves with the supporting unit 80d linearly in the longitudinal direction of the capsule-shaped casing 80.

The storage unit 84 stores the mass of body tissue which is cut out and obtained by the cutting unit 81 described above. As shown in FIG. 27, the storage unit 84 is arranged in the back of the capsule-shaped casing 80 at a position near the engaged point of the cylindrical casing 80a and the exterior 80c. The storage unit 84 is separated from the built-in components of the capsule medical device 82 (specifically, the electrical components such as the imaging unit 21c and the control unit 88, the power unit 29 such as the battery, the magnet 24, and the like). The storage unit 84 has an opening formed between the cylindrical casing 80*a* and the exterior 80*c*. When the storage unit 84 is not sealed by the lid part 85, the storage unit 84 contains and stores the mass of body tissue which is cut out and obtained by the cutting unit 81. The lid part 85 is contained near the storage unit 84, and the lid part 85 is driven to be extended and withdrawn by the motor 86 controlled by the control unit 88. When the lid part 85 is extended at the opening of the storage unit 84 due to the driving of the motor 86, the lid part 85 seals the storage unit 84.

When the control unit 88 acquires a detection signal indicating that the external magnetic field is detected from the magnetic sensor 25, the control unit 88 controls the motor 83*a* of the linear motion system 83 to move the exterior 80*c* away from the cylindrical casing 80*a* (i.e., to form an opening between the cylindrical casing 80*a* and the exterior 80*c*), so that the cutting unit 81 is exposed. Further, when the capsule-shaped casing 80 and the exterior 80*c* rotate along the circumferential direction due to the torque of the magnet 24 described above, the control unit 88 controls the motor 83*a* of the linear-motion system 83 to connect (engage) the exterior 80*c* with the cylindrical casing 80*a*. As a result, the portion of in-vivo region of the subject 1 is sandwiched by the cylindrical casing 80*a* and the exterior 80*c*, and the cutting unit 81 rotating along the circumferential direction with the exterior 80*c* cuts out and obtains the mass of body tissue from the sandwiched portion of in-vivo region. Then, the control unit 88 controls the motor 86 to move the lid part 85 to the opening of the storage unit 84. As a result, the storage unit 84 storing the mass of body tissue cut out and obtained by the cutting unit 81 is sealed by the lid part 85. Other functions of the control unit 88 are identical with those of the control unit 28 of the capsule medical device 2 according to the first embodiment except the control function of the driving unit 26 described above.

In the body-tissue obtaining system according to the fourth embodiment, the capsule medical device 82 configured as above is introduced into the subject 1, moves through the digestive organs of the subject 1 due to the peristalsis and the like, and reaches the in-vivo region to be examined. The user controls the magnetic-field generating unit 5 and the moving unit 7 via the input unit 8 while referring the in-vivo image and the current position information displayed on the display unit 4*r* similarly to the first embodiment described above.

The capsule medical device 82 inside the subject 1 moves the exterior 80*c* away from the cylindrical casing 80*a* at the timing when the rotating magnetic field and the gradient magnetic field are applied by the magnetic-field generating unit 5 described above so that the cutting unit 81 is exposed. The capsule medical device 82 rotates the cutting unit 81 along the circumferential direction of the capsule-shaped casing 80 due to the function of the rotating magnetic field and the gradient magnetic field, and keeps the portion of in-vivo region sandwiched between the cylindrical casing 80*a* and the exterior 80*c*. The cutting unit 81 cuts out and obtains the mass of body tissue from the sandwiched portion of in-vivo region. The mass of body tissue is stored in the storage unit 84 of the capsule medical device 82. When the capsule medical device 82 having obtained the mass of body tissue ceases to be influenced by the rotating magnetic field and the gradient magnetic field, the capsule medical device 82 moves through the digestive organs due to the peristalsis and the like until naturally excreted outside the subject 1 at last. The mass of body tissue stored in the storage unit 84 of the capsule medical device 82 is retrieved by the doctor, the nurse, or the like, and used for the biopsy such as the pathological diagnosis.

Figure 29:
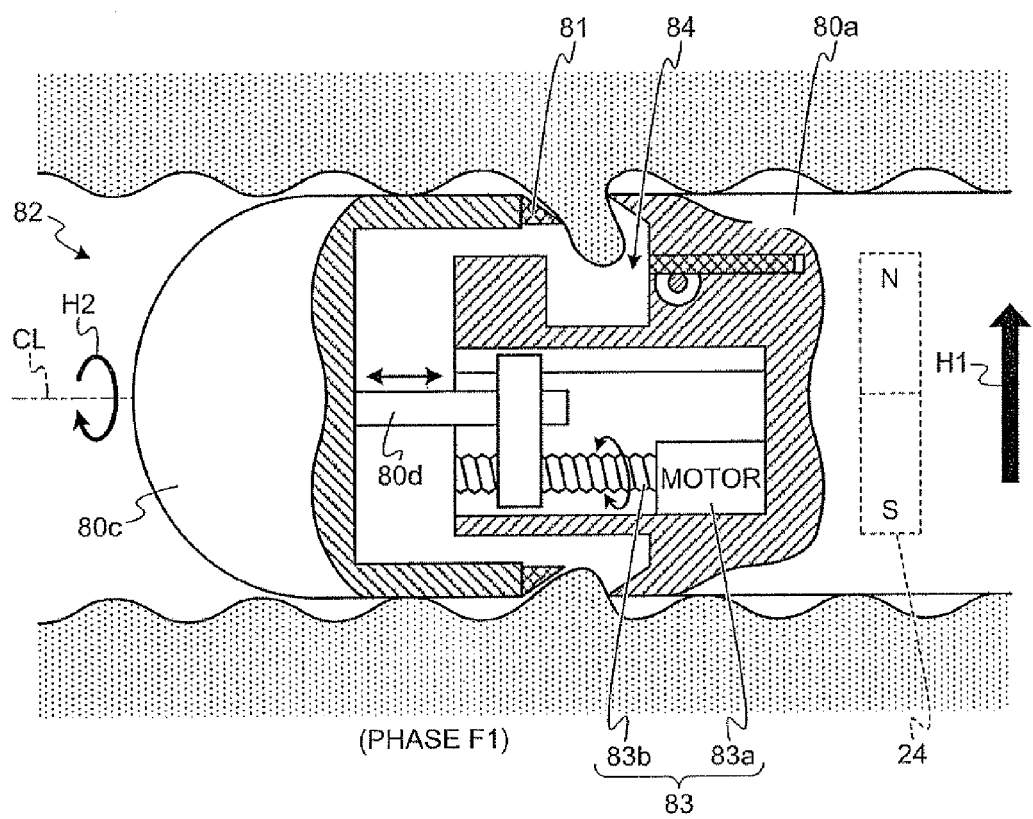
FIG. 29 is a schematic diagram illustrating a phase where the portion of the in-vivo region is sandwiched between a cylindrical casing and the exterior of the capsule medical device according to the fourth embodiment.
Figure 30:
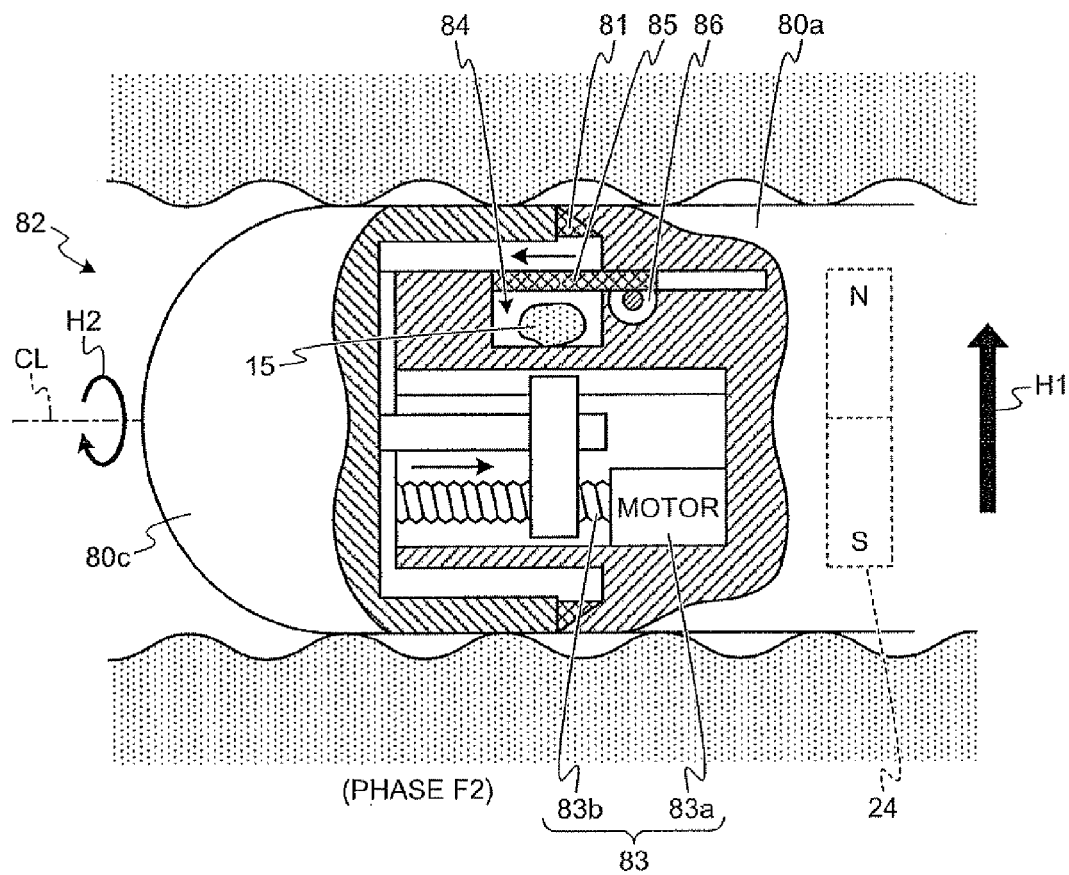
FIG. 30 is a schematic diagram illustrating a phase where the cutting unit of the capsule medical device according to the fourth embodiment cuts out and obtains the mass of body tissue from the portion of in-vivo region.

The operation of the capsule medical device 82 for cutting out and obtaining the mass of body tissue from the in-vivo region of the subject 1 is described. FIG. 29 is a schematic diagram illustrating a phase where the portion of in-vivo region is sandwiched by the cylindrical casing 80*a* and the exterior 80*c* of the capsule medical device 82 according to the fourth embodiment. FIG. 30 is a schematic diagram illustrating a phase where the mass of body tissue is cut out and obtained from the portion of in-vivo region by the cutting unit 81 of the capsule medical device 82 according to the fourth embodiment.

When the capsule medical device 82 inside the subject 1 reaches the in-vivo region to be examined, the magnetic-field generating unit 5 described above applied the gradient magnetic field and the rotating magnetic field to the capsule medical device 82. In the capsule medical device 82, the magnetic sensor 25 detects the rotating magnetic field H2 or the gradient magnetic field H1 generated by the magnetic-field generating unit 5. The control unit 88 drives the motor 83*a* of the linear-motion system 83 at the timing when the rotating magnetic field H2 or the gradient magnetic field is detected by the magnetic sensor 25 to move the exterior 80*c* away from the cylindrical casing 80*a* and form the opening between the cylindrical casing 80*a* and the exterior 80*c*, whereby the cutting unit 81 at the edge of the exterior 80*c* is exposed.

The capsule medical device 82 at the above state forces the cylindrical casing 80*a* and the exterior 80*c* into the in-vivo region due to the function of the magnet 24 influenced by the gradient magnetic field H1 (see FIG. 27), and rotates along the circumferential direction of the capsule-shaped casing 80 due to the function of the magnet 24 influenced by the rotating magnetic field H2. The capsule medical device 82 drives the motor 83*a* of the linear-motion system 83 to move the exterior 80*c* close to the cylindrical casing 80*a*. Thus the portion of in-vivo region is sandwiched between the cylindrical casing 80*a* and the exterior 80*c* (specifically, between the cutting unit 81 fixated on the edge of the exterior 80*c* and the cylindrical casing 80*a*) (phase F1).

The capsule medical device 82 at the phase F1 keeps rotating along the circumferential direction of the capsule-shaped casing 80 due to the torque of the magnet 24 influenced by the rotating magnetic field H2. The cylindrical casing 80*a* and the exterior 80*c* keep the portion of in-vivo region sandwiched and rotate along the circumferential direction. The cutting unit 81 rotating together with the exterior 80*c* along the circumferential direction. The cutting unit 81 maintains the inertia to remain rotating along the circumferential direction of the capsule-shaped casing 80, and converts the torque of the magnet 24 described above into the cutting force to thereby strengthen the cutting force. The cutting unit 81 with the strengthened cutting force cuts out and obtains the mass of body tissue from the portion of in-vivo region sandwiched between the cylindrical casing 80*a* and the exterior 80*c*. The cutting unit 81 is stored inside the cylindrical casing 80*a* as the cylindrical casing 80*a* and the exterior 80*c* are connected (engaged) with each other.

The mass of body tissue 15 which is cut out and obtained by the cutting unit 81 is stored in the storage unit 84 (phase F2). As shown in FIG. 30, the storage unit 84 storing therein the mass of body tissue 15 is sealed by the lid part 85. As a result, the storage unit 84 stores the mass of body tissue 15 and prevents the same from dropping out.

When the capsule medical device 82 having the mass of body tissue 15 stored in the storage unit 84 ceases to be influenced by the gradient magnetic field and the rotating magnetic field, the capsule medical device is naturally excreted outside the subject 1 due to the peristalsis and the like. After the capsule medical device 82 is naturally excreted outside the subject 1, the mass of body tissue 15 stored in the storage unit 84 is taken by the doctor, the nurse, or the like, and used for the biopsy such as the pathological diagnosis.

When the capsule medical device 82 cuts out and obtains the mass of body tissue from the in-vivo region of the subject 1 by the cutting unit 81, the portion of in-vivo region is sandwiched by the cylindrical casing 80*a* and the exterior 80*c* while the cutting unit 81 rotates along the circumferential direction of the capsule-shaped casing 80 due to the external rotating magnetic field. The capsule medical device 82 maintains the rotation inertia of the cutting unit 81 to remain rotating along the circumferential direction, and converts the torque along the circumferential direction generated by the magnet 24 rotating due to the external magnetic field into the cutting force of the cutting unit 81 while the portion of in-vivo region is captured inside and fixated between the cylindrical casing 80*a* and the exterior 80*c*. Thus, the cutting force of the cutting unit 81 can be properly strengthened even in a small space such as the small intestine and the large intestine. The cutting force of the cutting unit 81 strengthened as above is much stronger than that of the forceps and the like of the conventional capsule medical device where the straight-line stroke of the forceps to be extended or withdrawn from the capsule-shaped casing is limited in a small space due to the size of the capsule-shaped casing. The cutting force is made strong enough to securely cut out and obtain the mass of body tissue (the mass of body tissue 15) from the in-vivo region of the subject 1.

The mass of body tissue 15 which is cut out and obtained by the capsule medical device 82 is large enough to be used as a sample for the biopsy. The biopsy such as the pathological diagnosis using the mass of body tissue 15 can enhance accuracy of the biopsy and provide abundant medical information which is hard to obtain with a small amount of the body tissue such as a cross-sectional view or the like of the body tissue of the in-vivo region to be examined.

The capsule medical device 82 described above has the exterior 80*c* rotated less than one revolution along the circumferential direction with the capsule-shaped casing 80*r* and the cutting unit 81 rotates along the circumferential direction with the exterior 80*c* in order to obtain the cutting force to securely cut out and obtain the mass of body tissue 15 from the in-vivo region. The number of revolutions of the cutting unit 81 may be increased to further strengthen the cutting force of the cutting unit 81. Specifically, the capsule medical device 82 keeps rotating the exterior 80*c* one or more revolutions along the circumferential direction due to the external rotating magnetic field to increase the number of revolutions of the cutting unit 81 rotating along the circumferential direction with the exterior 80*c* to one or more. Thus the amount of movement of the cutting unit 81 may be increased up to infinity (equal to or longer than a length of the circumference along the circumferential direction of the capsule-shaped casing 80) along the circumferential direction of the capsule-shaped casing 80. As a result, the capsule medical device 82 can further strengthen the cutting force of the cutting unit 81 compared with the case where the number of revolutions of the exterior 80*c*, i.e., of the capsule-shaped casing 80 is less than one, whereby the mass of body tissue 15 can be even more securely cut out and obtained from the in-vivo region.

As described above, in the fourth embodiment of the present invention, the exterior is arranged on the edge of the capsule-shaped casing in a manner such that the exterior can be linearly moved away from or engaged with the capsule-shaped casing. The cutting unit is fixated on the edge where the exterior is engaged with the capsule-shaped casing with the edge of the cutting unit facing in the longitudinal direction of the capsule-shaped casing. The portion of in-vivo region of the subject is sandwiched between the exterior and the capsule-shaped casing. The blade of the cutting unit is forced into the sandwiched portion of in-vivo region. The cutting unit is rotated along the circumferential direction with the exterior due to the torque along the circumferential direction generated by the rotation driving unit arranged inside the capsule-shaped casing. Thus, the cutting unit rotating along the circumferential direction cuts out and obtains the mass of body tissue from the portion of in-vivo region. Other configurations are substantially identical with those of the first embodiment. Similarly to the first embodiment described above in a substantial way, the rotation inertia of the cutting unit is maintained, and the torque along the circumferential direction is converted into the cutting force of the cutting unit. Further, the mass of body tissue which is large enough is sandwiched and fixated between the exterior and the capsule-shaped casing due to the linear motion (reciprocating motion) of the exterior. As a result, the capsule medical device and the body-tissue obtaining method which can provide as much advantage as the first embodiment described above does, and which can easily achieve the cutting and obtaining of the mass of body tissue by the cutting unit can be realized.

Figure 31:
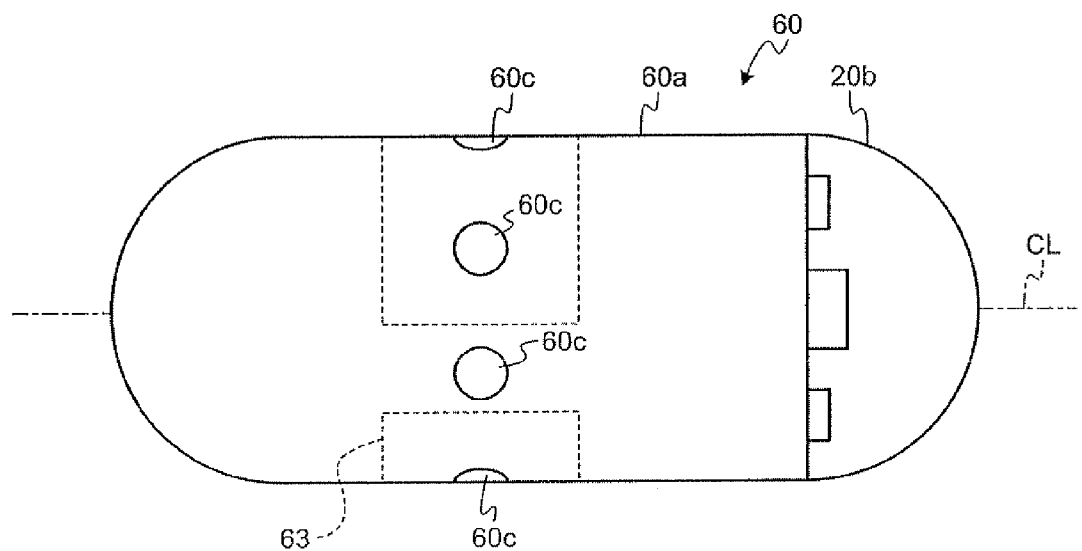
FIG. 31 is a schematic diagram of a first modification of the capsule medical device according to the second embodiment.
Figure 32:
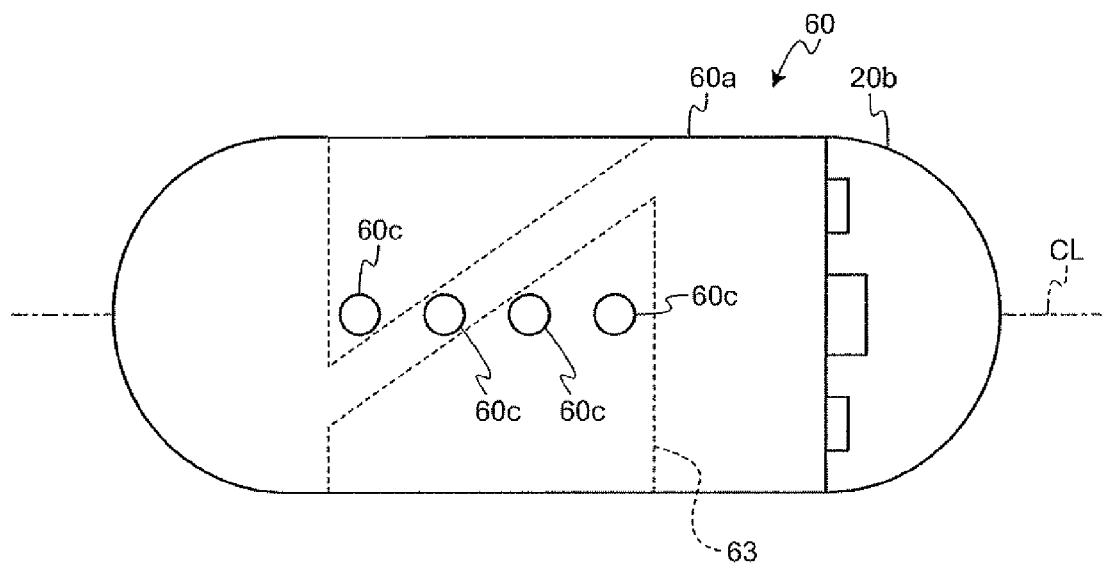
FIG. 32 is a schematic diagram of a second modification of the capsule medical device according to the second embodiment.
Figure 33:
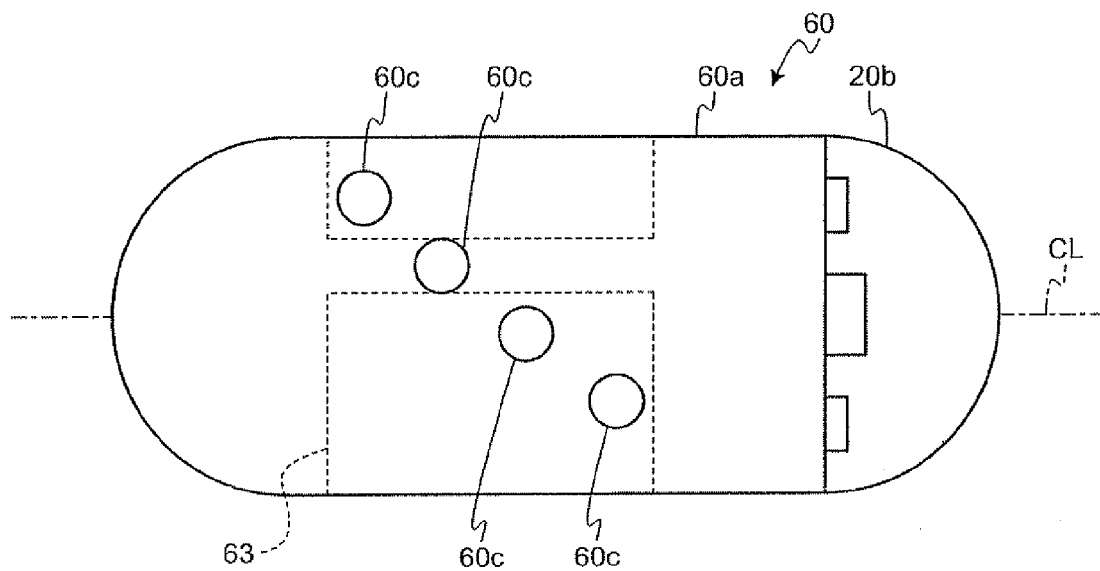
FIG. 33 is a schematic diagram of a third modification of the capsule medical device according to the second embodiment.

In the second embodiment described above, the opening 60*c* through which the portion of in-vivo region is pulled (sucked) into the capsule-shaped casing 60 is formed on a portion of the capsule-shaped casing. Alternatively, the opening 60*c* may be formed on plural portions of the capsule-shaped casing 60. In this case, the opening for sucking the portion of in-vivo region may be selected in turn from the plural openings 60*c* formed on the portions of the capsule-shaped casing 60. Specifically, as shown in FIG. 31, the openings 60*c* may be formed along the circumferential direction of the capsule-shaped casing 60. Further, as shown in FIG. 32, the openings 60*c* may be formed along the longitudinal direction of the capsule-shaped casing 60. Further, as shown in FIG. 33, the openings 60*c* may be formed along a direction tilted to the circumferential direction and to the longitudinal direction of the capsule-shaped casing 60. In any of the cases above, the separator 61 can have the openings formed on the plural portions corresponding to the openings 60*c*. Further, the cutting unit 63 can be curved along the inner circle of the cylindrical casing 60*a* as shown in FIGS. 31 to 33. The cutting unit 63 can rotate along the circumferential direction of the capsule-shaped casing 60*r* and can open one of the opening 60*c* with the other two or more openings 60*c* kept closed. According to the configuration above, the capsule medical device which can easily cut out and obtain the in-vivo region to be examined at the plural points can be realized.

Further, in the second embodiment, the third embodiment and the first modification of the first embodiment, the cutting unit is rotated along the circumferential direction of the capsule-shaped casing due to the driving force (torque) of the motor. Alternatively, the cutting unit may be rotated along the circumferential direction of the capsule-shaped casing due to the toque of the magnet influenced by the external magnetic field as illustrated by the first embodiment described above and the like. In this case, the capsule medical device may perform the series of operations for cutting out and obtaining the mass of body tissue based on the control signal from the control unit 30 arranged outside. Further, as illustrated in the first embodiment and the like, the magnetic sensor may be arranged in the capsule-shaped casing, and the capsule medical device may perform the series of operations for cutting out and obtaining the mass of body tissue based on the detection signal of the magnetic sensor indicating the external magnetic field is detected.

Further, in the first embodiment, the second modification, and the fourth embodiment described above, the magnetic sensor is arranged in the capsule-shaped casing, and the capsule medical device performs the series of operations for cutting out and obtaining the mass of body tissue based on the detection signal of the magnetic sensor indicating that the external magnetic field is detected. Alternatively, as illustrated in the second embodiment and the like described above, the capsule medical device may perform the series of operations for cutting out and obtaining the mass of body tissue based on the control signal of the control unit 30 arranged outside.

Further, in the second embodiment, the third embodiment, and the first modification of the first embodiment, the capsule medical device inside the subject starts the series of the operations for cutting out and obtaining the mass of body tissue based on the controls signal from outside, and stops the series of operations the predetermined time after the control signal is acquired. Alternatively, the control signal for starting the operations to the capsule-shaped may be transmitted to the capsule medical device inside the subject so that the capsule medical device starts the series of operations based on the control signal for starting the operations. Then, the control signal for stopping the operations may be transmitted to the capsule medical device at the desired timing so that the capsule medical device stops the series of operations based on the control signal for stopping the operations.

Further, in the first embodiment described above, the opening-closing part of the storage unit is opened and closed due to the elastic force (urging force) of the spring. Alternatively, as shown in the first modification of the first embodiment described above, the opening-closing part of the storage unit may be driven to be opened and closed due to the driving force of the motor. Further, in the first modification of the first embodiment described above, the opening-closing part of the storage unit is driven to be opened and closed due to the driving force of the motor. Alternatively, the opening-closing part of the storage unit may be opened and closed due to the elastic force (urging force) of the spring.

In the fourth embodiment described above, the exterior 80c is not rotated along the circumferential direction relative to the cylindrical casing 80a while the exterior 80c is linearly moved away from or close to the cylindrical casing 80a. Alternatively, the exterior 80c may be rotated along the circumferential direction relative to the cylindrical casing 80a while the exterior 80c is linearly moved away from or close to the cylindrical casing 80a. In this case, the motor which linearly moves the exterior 80c generates the torque along the circumferential direction, and thus, the magnet rotating along the circumferential direction that is influenced by the external rotating magnetic field is not required to be arranged in the capsule-shaped casing.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical device comprising:
   a capsule-shaped casing that can be introduced into an in-vivo region of a subject;
   a rotation driving unit that generates torque along a circumferential direction of the capsule-shaped casing; and
   a cutting-obtaining unit that rotates along the circumferential direction of the capsule-shaped casing due to the torque to cut out and obtain a mass of body tissue from the in-vivo region of the subject,
   wherein the rotation driving unit is a magnet that rotates the capsule-shaped casing and the cutting-obtaining unit along the circumferential direction of the capsule-shaped casing due to an external rotating magnetic field.

2. The capsule medical device according to claim 1, wherein the cutting-obtaining unit includes a blade.

3. The capsule medical device according to claim 2, wherein the blade is fixated to the capsule-shaped casing, and the rotation driving unit rotates the capsule-shaped casing and the blade along the circumferential direction of the capsule-shaped casing.

4. The capsule medical device according to claim 2, further comprising
   a covering member that is movably arranged on the capsule-shaped casing and covers the blade, and
   a driving unit that moves the covering member, and switches the covering member to a state where the blade is exposed to the in-vivo region of the subject, or a state where the blade is covered.

5. The capsule medical device according to claim 1, wherein the rotation driving unit rotates the blade with the capsule-shaped casing along the circumferential direction of the capsule-shaped casing due to the external rotating magnetic field, and presses the capsule-shaped casing to the in-vivo region of the subject due to an external gradient magnetic field.

6. The capsule medical device according to claim 1, wherein the cutting-obtaining unit rotates one or more revolutions along the circumferential direction of the capsule-shaped casing.

7. A body-tissue obtaining method, comprising:
   introducing a capsule medical device into a body of a subject;
   determining whether the capsule medical device has reached an in-vivo region to be examined of the subject;
   cutting out and obtaining a mass of body tissue from the region to be examined by rotating a cutting-obtaining unit provided in the capsule medical device along a circumferential direction of a casing of the capsule medical device by a magnet provided in the capsule medical device as a rotation driving unit due to an external rotating magnetic field;
   storing the mass of body tissue obtained in a storage unit inside the capsule medical device; and
   taking the mass of body tissue stored in the storage unit of the capsule medical device which has excreted from the subject.

* * * * *